US011850290B2

(12) United States Patent
Lu et al.

(10) Patent No.: US 11,850,290 B2
(45) Date of Patent: *Dec. 26, 2023

(54) MATERIALS AND DEVICES CONTAINING HYDROGEL-ENCAPSULATED CELLS

(71) Applicant: Massachusetts Institute of Technology, Cambridge, MA (US)

(72) Inventors: Timothy Kuan-Ta Lu, Cambridge, MA (US); Xinyue Liu, Cambridge, MA (US); Tzu-Chieh Tang, Boston, MA (US); Eléonore Claire Tham, Cambridge, MA (US); Xuanhe Zhao, Allston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1111 days.

This patent is subject to a terminal disclaimer.

(21) Appl. No.: 16/318,958

(22) PCT Filed: Jul. 20, 2017

(86) PCT No.: PCT/US2017/043094
§ 371 (c)(1),
(2) Date: Jan. 18, 2019

(87) PCT Pub. No.: WO2018/017845
PCT Pub. Date: Jan. 25, 2018

(65) Prior Publication Data
US 2019/0240356 A1    Aug. 8, 2019

Related U.S. Application Data

(60) Provisional application No. 62/365,073, filed on Jul. 21, 2016, provisional application No. 62/457,440, filed on Feb. 10, 2017.

(51) Int. Cl.
| | |
|---|---|
| *A61K 49/00* | (2006.01) |
| *A61B 5/00* | (2006.01) |
| *C12N 11/04* | (2006.01) |
| *C12N 11/10* | (2006.01) |
| *C12N 15/63* | (2006.01) |
| *C12N 15/70* | (2006.01) |
| *C12Q 1/6897* | (2018.01) |

(52) U.S. Cl.
CPC ........ *A61K 49/0097* (2013.01); *A61B 5/6806* (2013.01); *A61B 5/6833* (2013.01); *A61K 49/0073* (2013.01); *C12N 11/04* (2013.01); *C12N 11/10* (2013.01); *C12N 15/63* (2013.01); *C12N 15/70* (2013.01); *C12Q 1/6897* (2013.01)

(58) Field of Classification Search
CPC ........ A61K 47/34; A61K 47/36; C12N 11/04; C12N 2533/74
See application file for complete search history.

(56) References Cited

U.S. PATENT DOCUMENTS

| | | | |
|---|---|---|---|
| 11,148,389 B2 * | 10/2021 | Zhao ....................... | B32B 27/06 |
| 2005/0037054 A1 | 2/2005 | Hamann | |
| 2012/0196770 A1 | 8/2012 | Agresti | |

OTHER PUBLICATIONS

Hernandez et al. 2010; Microcapsules and microcarriers for in situ cell delivery. Advanced Drug Delivery Reviews. 62: 711-730.*
Wright et al. 2015; GeneGuard: A modular plasmid system designed for biosafety. ACS Synth. Biol. 4:307-316.*
Stafford, 2005. Microbial signaling systems: Methods and applications. On the web at ocw.aprende.org/courses/biology/7-349-biological-computing-at-the-crossroads-of-engineering-and-science-spring-2005/assignments/assgn2_kate.pdf. pages 1-7.*
Yuk et al., Skin-inspired hydrogel-elastomer hybrids with robust interfaces and functional microstructures. Nat Commun. Jun. 27, 2016;7:12028. doi: 10.1038/ncomms12028.
PCT/US2017/043094, Oct. 4, 2017, International Search Report and Written Opinion.
Chen et al., Engineering living functional materials. ACS Synth Biol. Jan. 16, 2015;4(1):8-11.
Chen et al., Synthesis and patterning of tunable multiscale materials with engineered cells. Nat Mater. May 2014; 13(5):515-23. doi: 10.1038/nmat3912. Epub Mar. 23, 2014.
Choi et al., Light-guiding hydrogels for cell-based sensing and optogenetic synthesis in vivo. Nat Photonics. 2013;7:987-994.
Feinberg et al., Muscular thin films for building actuators and powering devices. Science 317(5843):1366-1370.
Halldorssen et al., Advantages and challenges of microfluidic cell culture in polydimethylsiloxane devices. Biosens Bioelectron. Jan. 15, 2015;63:218-231. doi: 10.1016/j.bios.2014.07.029. Epub Jul. 19, 2014.
Huh et al., Reconstituting organ-level lung functions on a chip. Science. Jun. 25, 2010;328(5986):1662-8.
Jang et al., Rugged and breathable forms of stretchable electronics with adherent composite substrates for transcutaneous monitoring. Nat Commun. Sep. 3, 2014;5:4779.
Kuhlman et al., Combinatorial transcriptional control of the lactose operon of *Escherichia coli*. Proc Natl Acad Sci U S A. Apr. 3, 2007;104(14):6043-8. doi: 10.1073/pnas.0606717104. Epub Mar. 21, 2007.
Lee et al., Compatibility of mammalian cells on surfaces of poly(dimethylsiloxane). Langmuir. Dec. 21, 2004;20(26):11684-91.
Lee et al., Alginate: properties and biomedical applications. Prog Polym Sci. Jan. 2012;37(1):106-126.
Leveau et al., Predictive and interpretive simulation of green fluorescent protein expression in reporter bacteria. J Bacteriol. Dec. 2001;183(23):6752-62.
Liao et al., Composite three-dimensional woven scaffolds with interpenetrating network hydrogels to create functional synthetic articular cartilage. Adv Funct Mater. Dec. 17, 2013;23(47):5833-5839.

(Continued)

*Primary Examiner* — Suzanne M Noakes
(74) *Attorney, Agent, or Firm* — Wolf, Greenfield & Sacks, P.C.

(57) ABSTRACT

Provided herein, in some embodiments, are hydrogel-elastomer and hydrogel-alginate devices, compositions and associated methods to encapsulate living cells.

18 Claims, 31 Drawing Sheets

(56) References Cited

OTHER PUBLICATIONS

Lin et al., Stretchable Hydrogel Electronics and Devices. Adv Mater. Jun. 2016;28(22):4497-505. doi: 10.1002/adma.201504152. Epub Dec. 7, 2015.
Sun et al., Highly stretchable and tough hydrogels. Nature. Sep. 6, 2012;489(7414):133-6.
Yuk et al., Skin-inspired hydrogel-elastomer hybrids with robust interfaces and functional microstructures. Nat Commun. Jun. 27, 2016;7:12028.
Yuk et al., Tough bonding of hydrogels to diverse non-porous surfaces. Nat Mater. Feb. 2016;15(2):190-6. doi: 10.1038/nmat4463. Epub Nov. 9, 2015.
Yuk et al., Hydraulic hydrogel actuators and robots optically and sonically camouflaged in water. Nat Commun. Feb. 1, 2017;8:14230.
Zhao et al., Active scaffolds for on-demand drug and cell delivery. Proc Natl Acad Sci U S A. Jan. 4, 2011;108(1):67-72. doi: 10.1073/pnas.1007862108. Epub Dec. 13, 2010.
Zhao, Multi-scale multi-mechanism design of tough hydrogels: building dissipation into stretchy networks. Soft Matter. Feb. 7, 2014;10(5):672-87.
Zhong et al., Strong underwater adhesives made by self-assembling multi-protein nanofibres. Nat Nanotechnol. Oct. 2014;9(10):858-66. doi: 10.1038/nnano.2014.199. Epub Sep. 21, 2014.
Anselmo et al., Layer-by-Layer Encapsulation of Probiotics for Delivery to the Microbiome. Adv Mater. Nov. 2016;28(43):9486-9490. doi: 10.1002/adma.201603270. Epub Sep. 12, 2016.
Basu et al., A synthetic multicellular system for programmed pattern formation. Nature. Apr. 28, 2005;434(7037):1130-4.
Belkin, Microbial whole-cell sensing systems of environmental pollutants. Curr Opin Microbiol. Jun. 2003;6(3):206-12.
Billiet et al., A review of trends and limitations in hydrogel-rapid prototyping for tissue engineering. Biomaterials. Sep. 2012;33(26):6020-41. doi: 10.1016/j.biomaterials.2012.04.050. Epub Jun. 7, 2012.
Brocklehurst et al., ZntR is a Zn(II)-responsive MerR-like transcriptional regulator of zntA in *Escherichia coli*. Mol Microbiol. Feb. 1999;31(3):893-902.
Cubitt et al., Understanding, improving and using green fluorescent proteins. Trends Biochem Sci. Nov. 1995;20(11):448-55.
Darnell et al., Performance and biocompatibility of extremely tough alginate/polyacrylamide hydrogels. Biomaterials. Nov. 2013;34(33):8042-8. doi: 10.1016/j.biomaterials.2013.06.061. Epub Jul. 26, 2013.
De Las Heras et al., Stable implantation of orthogonal sensor circuits in Gram-negative bacteria for environmental release. Environ Microbiol. Dec. 2008; 10(12):3305-16. doi: 10.1111/j.1462-2920.2008.01722.x. Epub Aug. 18, 2008.
Dilanji et al., Quorum activation at a distance: spatiotemporal patterns of gene regulation from diffusion of an autoinducer signal. J Am Chem Soc. Mar. 28, 2012;134(12):5618-26. doi: 10.1021/ja211593q. Epub Mar. 16, 2012.
Farzadfard et al., Synthetic biology. Genomically encoded analog memory with precise in vivo DNA writing in living cell populations. Science. Nov. 14, 2014;346(6211):1256272.
Gerber et al., Incorporation of penicillin-producing fungi into living materials to provide chemically active and antibiotic-releasing surfaces. Angew Chem Int Ed Engl. Nov. 5, 2012;51(45):11293-6. doi: 10.1002/anie.201204337. Epub Oct. 9, 2012.

Gong et al., Double-network hydrogels with extremely high mechanical strength. Adv Mater 2003; 15(14): 1155-8.
Gordon et al., Antibiotic interaction and diffusion through alginate and exopolysaccharide of cystic fibrosis-derived Pseudomonas aeruginosa. J Antimicrob Chemother. Nov. 1988;22(5):667- 74.
Kearney et al., Macroscale delivery systems for molecular and cellular payloads. Nat Mater. Nov. 2013;12(11):1004-17.
Knierim et al, Blocked bacteria escape by ATRP grafting of a PMMA shell on PVA microparticles. Macromol Biosci. Apr. 2014;14(4):537-45. doi: 10.1002/mabi.201300398. Epub Nov. 29, 2013.
Kong et al., Regulated programmed lysis of recombinant *Salmonella* in host tissues to release protective antigens and confer biological containment. Proc Natl Acad Sci U S A. Jul. 8, 2008;105(27):9361-6. doi: 10.1073/pnas.0803801105. Epub Jul. 7, 2008.
Lee et al., Hydrogels for tissue engineering. Chem Rev. 2001; 101(7): 1869-80.
Liu et al., Stretchable living materials and devices with hydrogel-elastomer hybrids hosting programmed cells. Proc Natl Acad Sci U S A. Feb. 28, 2017;114(9):2200-2205. doi: 10.1073/pnas.1618307114. Epub Feb. 15, 2017.
Nawroth et al., A tissue-engineered jellyfish with biomimetic propulsion. Nat Biotechnol. Aug. 2012;30(8):792-7.
Robb, Thin silicone membranes—their permeation properties and some applications. Ann N Y Acad Sci. Jan. 1968; 146(1):119-37.
Rovner et al., Recoded organisms engineered to depend on synthetic amino acids. Nature. Feb. 5, 2015;518(7537):89-93. doi: 10.1038/nature14095. Epub Jan. 21, 2015. Erratum in: Nature. Nov. 12, 2015;527(7577):264.
Seliktar, Designing cell-compatible hydrogels for biomedical applications. Science. Jun. 1, 2012;336(6085):1124-8.
Socolovsky et al., Environmental fluid mechanics part I: mass transfer and diffusion. 2002. 3 pages.
Steidler et al., Biological containment of genetically modified Lactococcus lactis for intestinal delivery of human interleukin 10. Nat Biotechnol. Jul. 2003;21(7):785-9. doi: 10.1038/nbt840. Epub Jun. 15, 2003.
Szafranski et al., A new approach for containment of microorganisms: dual control of streptavidin expression by antisense RNA and the T7 transcription system. Proc Natl Acad Sci U S A. Feb. 18, 19978;94(4):1059-63.
Tamsir et al., Robust multicellular computing using genetically encoded NOR gates and chemical 'wires'. Nature. Jan. 13, 2011;469(7329):212-5. doi: 10.1038/nature09565. Epub Dec. 8, 2010.
Trappmann et al., Extracellular-matrix tethering regulates stem-cell fate. Nat Mater. May 27, 2012;11(7):642-9. doi: 10.1038/nmat3339. Erratum in: Nat Mater. Aug. 2012;11(8):742.
Valade et al., Polyacrylamide hydrogel membranes with controlled pore sizes. 2013; 51(1): 129-38.
Vegas et al., Combinatorial hydrogel library enables identification of materials that mitigate the foreign body response in primates. Supplementary Information. Nat Biotechnol. Mar. 2016;34(3):345-52. doi: 10.1038/nbt.3462. Epub Jan. 25, 2016. Erratum in: Nat Biotechnol. Jun. 2016;34(6):666. Erratum in: Nat Biotechnol. Jun. 9, 2016;34(6):666.
Wright et al., Building-in biosafety for synthetic biology. Microbiology (Reading). Jul. 2013;159(Pt 7):1221-1235. doi: 10.1099/mic.0.066308-0. Epub Mar. 21, 2013.

\* cited by examiner

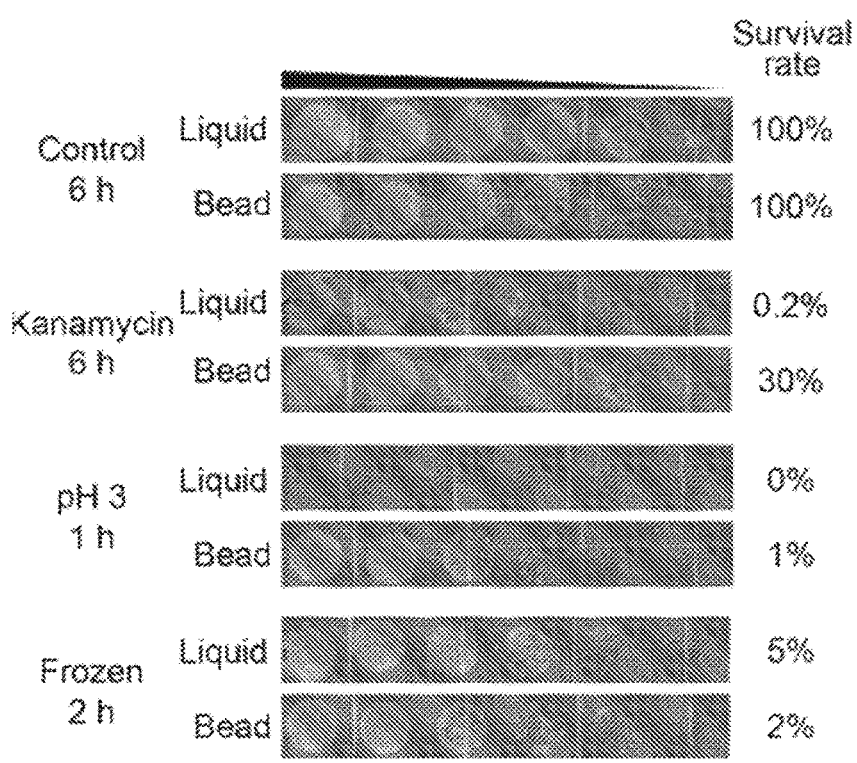

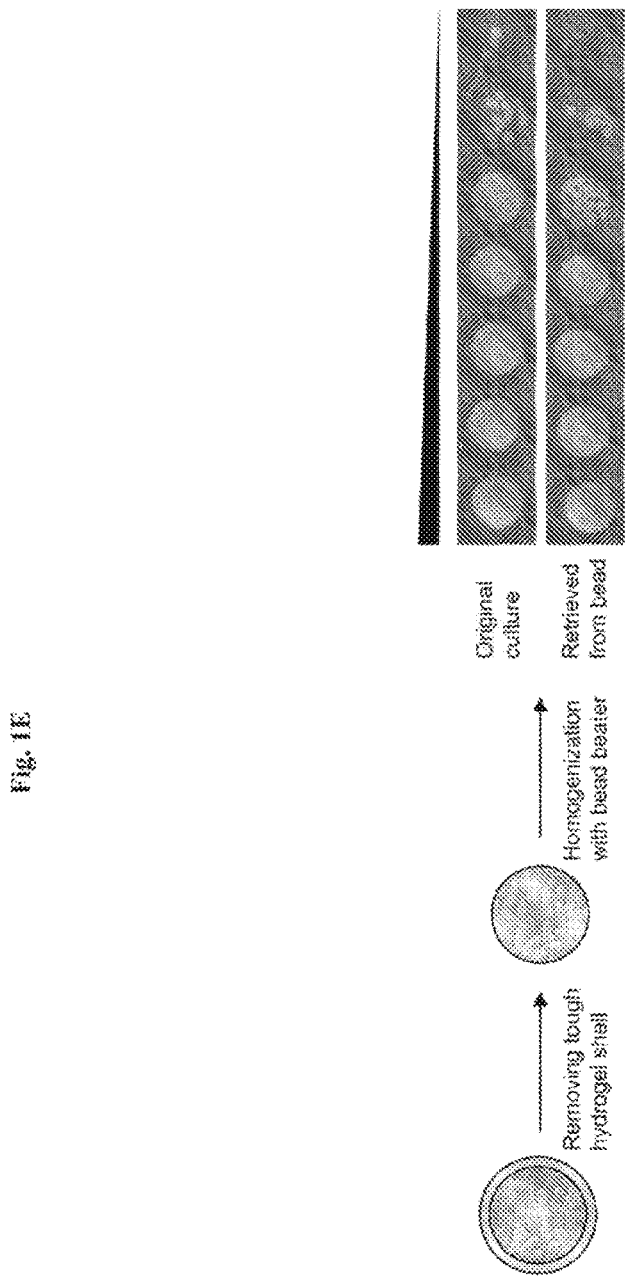

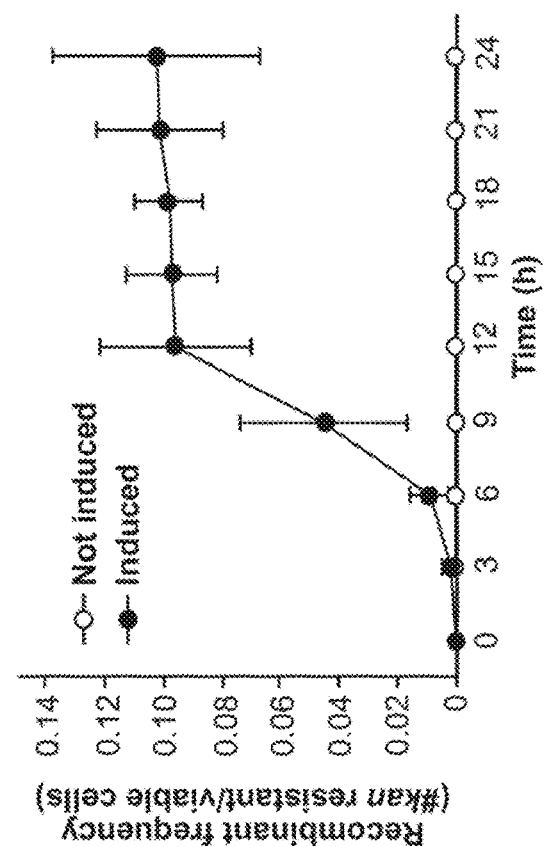
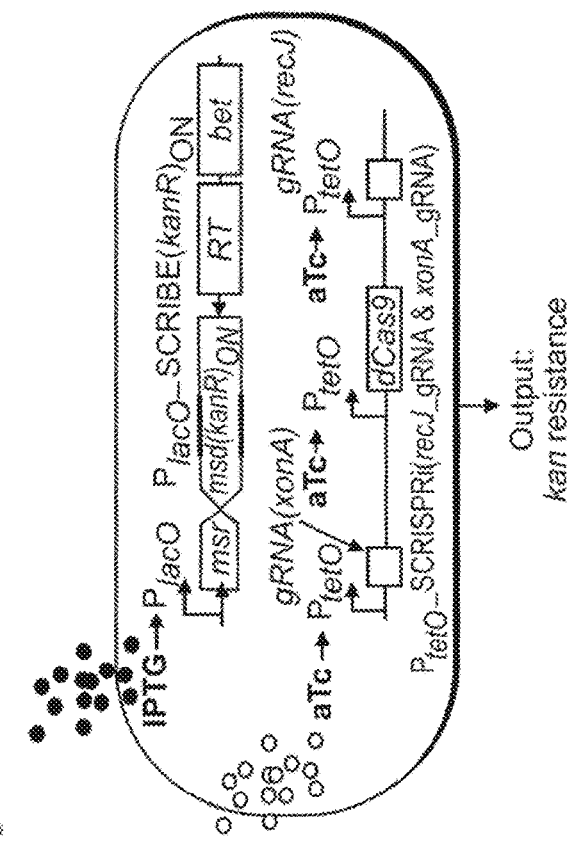
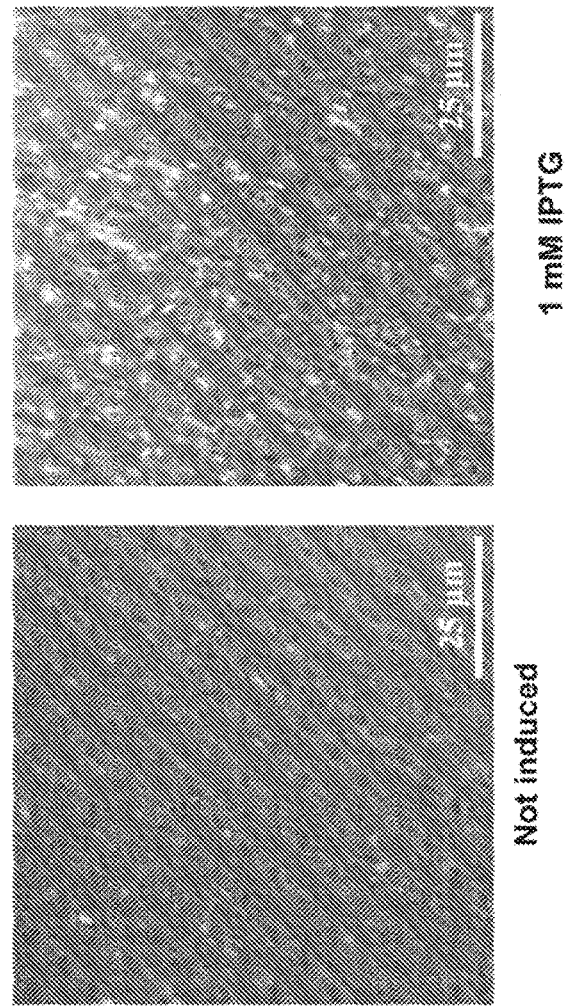
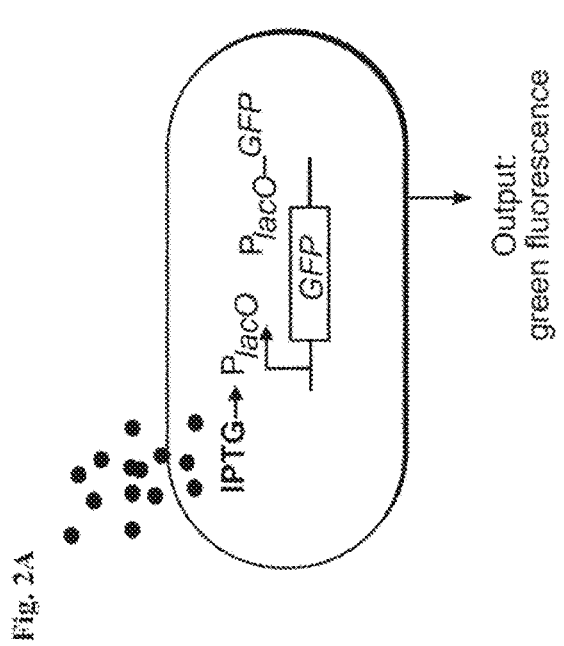
Fig. 2A
Fig. 2B

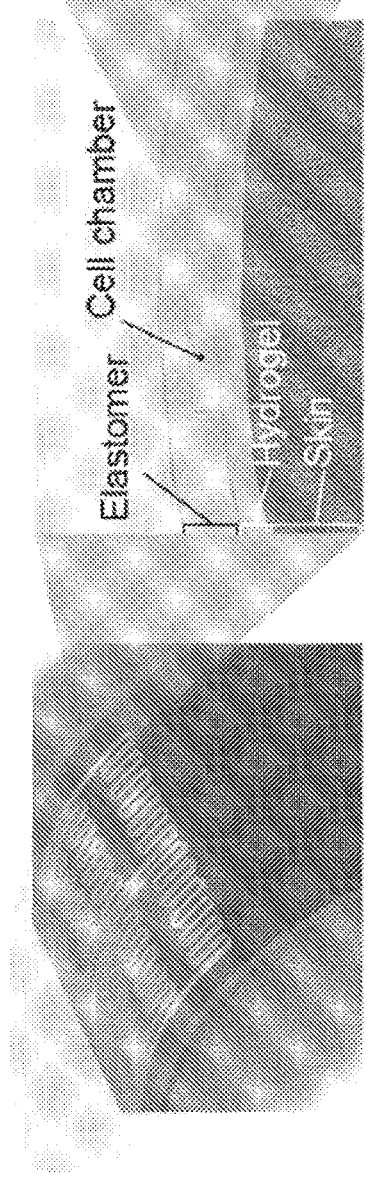
Fig. 9A
Fig. 9B
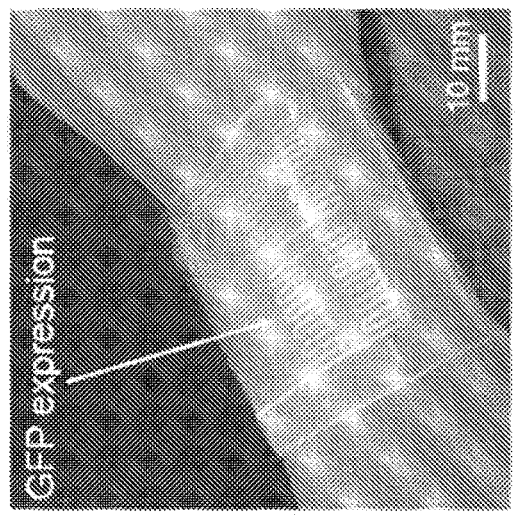
Fig. 9C
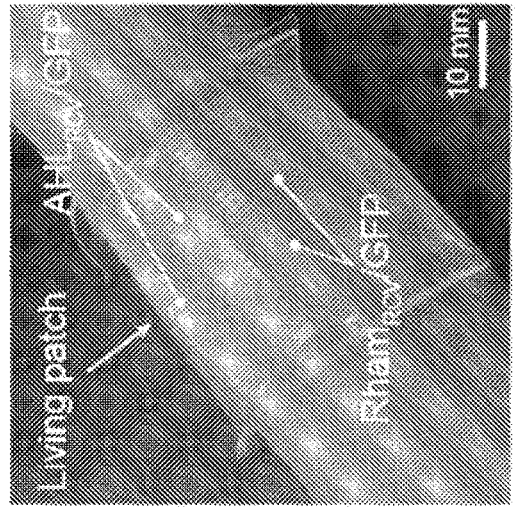
Fig. 9D
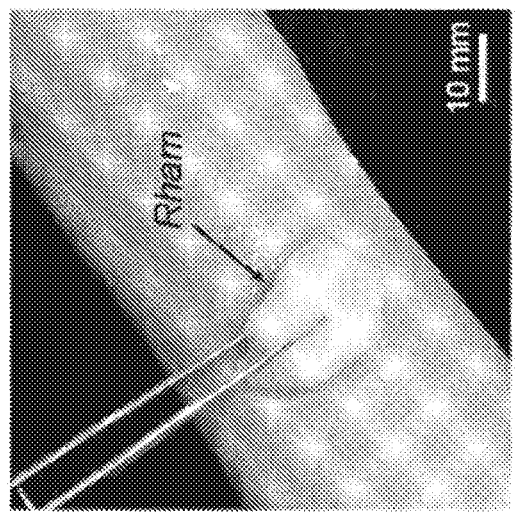

MATERIALS AND DEVICES CONTAINING HYDROGEL-ENCAPSULATED CELLS

RELATED APPLICATIONS

This application is a national stage filing under 35 U.S.C. § 371 of International Patent Application Serial No. PCT/US2017/043094, filed Jul. 20, 2017, which claims the benefit under 35 U.S.C. § 119(e) of U.S. provisional application No. 62/457,440 filed Feb. 10, 2017 and U.S. provisional application No. 62/365,073 filed Jul. 21, 2016, the contents of each of which is incorporated by reference herein in its entirety.

FEDERALLY SPONSORED RESEARCH

This invention was made with Government support under Grant Nos. N00014-13-1-0424 and N00014-14-1-0619 awarded by the Office of Naval Research. The Government has certain rights in the invention.

SUMMARY

Living systems, such as bacteria, yeasts, and mammalian cells, can be genetically programmed with synthetic circuits that execute sensing, computing, memory, and response functions. Integrating these functional living components (referred to as genetically modified microorganisms (GMMs)) into materials and devices provide powerful tools for scientific research and enable new technological applications. It has been a challenge to maintain the viability, functionality and safety of living components in freestanding materials and devices, which frequently undergo deformations during applications. The present disclosure provides, in some embodiments, a set of living materials and devices based on stretchable, robust and biocompatible hydrogel-elastomer hybrids that host various types of GMMs, including genetically-engineered bacterial cells. The hydrogel component provides sustainable supplies of water and nutrients and the elastomer component is air permeable, maintaining long-term viability and functionality of the encapsulated cells. Communication between different GMMs, such as different bacterial strains, and with the environment is achieved via diffusion of molecules in the hydrogel. The high stretchability and robustness of the hydrogel-elastomer hybrids prevents leakage of cells from the living materials and devices, even under large deformations. Novel functions and applications of stretchable living sensors that are responsive to multiple chemicals in a variety of form factors, including skin patches and biosensing gloves are demonstrated herein. In addition, a quantitative model was developed that couples transportation of signaling molecules and cellular response to aid the design of future living materials and devices.

Further, the containment of GMMs is a major bottleneck for realizing the promise of synthetic biology technologies in the environment. While biological strategies have been implemented to restrict the growth and replication of GMMs, there is a need for orthogonal technologies to achieve redundant and multilayered containment. Thus, the present disclosure also provides a hydrogel-based encapsulation system for GMMs that incorporates a tough biocompatible shell and an alginate-based core. This physical containment strategy allows samples to be easily retrieved, bacteria to be protected against environmental insults, and the lifespan of genetically re-coded bacteria to be controlled. Robustly encapsulated cells can carry out useful functions, including sensing heavy metals in water samples and performing cell-cell communication with other encapsulated bacteria, for example. Robust encapsulation strategies enable integrated physical and biological containment of GMMs and enable a wide range of applications. Thus, also provided herein, in some embodiments, are hydrogel devices having a tough (hard) hydrogel shell that are used to encapsulate living cells. Such devices enable, for example, tough, low cost, biocontained, distributed cell-based sensors, remediation systems and therapeutics. These hydrogel devices of the present disclosure combine physical and chemical containment to overcome barriers to deployment of synthetic organisms in a variety of applications.

In some embodiments, the present disclosure provides wearable devices comprising a hydrogel-elastomer composition encapsulating a population of genetically-engineered cells that comprise a promoter operably linked to a nucleic acid encoding a product of interest.

In other embodiments, the present disclosure provides skin patches, comprising a first layer comprising a hydrogel containing genetically-engineered cells and a second layer comprising an elastomer.

In yet other embodiments, the present disclosure provides biosensing gloves having fingertips that comprise a hydrogel-elastomer composition encapsulating a population of genetically-engineered cells that comprise a promoter operably linked to a nucleic acid encoding a product of interest.

Also provided herein, in some embodiments, are hydrogel-elastomer compositions encapsulating a population of genetically-engineered cells that comprise a promoter operably linked to a nucleic acid encoding a product of interest.

In some embodiments, the present disclosure provides methods, comprising (a) contacting a hydrogel-elastomer composition with a solution containing cell nutrients to produce a nutrient-infused hydrogel-elastomer composition, and (b) introducing a population of genetically-engineered cells into the nutrient-infused hydrogel-elastomer composition to produce genetically-engineered cells encapsulated by the nutrient-infused hydrogel, wherein the genetically-engineered cells comprise a promoter operably linked to a nucleic acid encoding a product of interest.

Also provided herein, in some embodiments, are hydrogel-alginate capsules comprising a hydrogel shell and an alginate core containing a population of genetically-engineered cells that comprise a promoter operably linked to a nucleic acid encoding a product of interest.

The present disclosure also provides, in some embodiments, systems comprising (a) a first population of hydrogel-alginate capsules comprising (i) a hydrogel shell and (ii) an alginate core containing a population of genetically-engineered cells that comprise a first inducible promoter operably linked to a nucleic acid encoding a first product of interest, and (b) a second population of hydrogel-alginate capsules comprising (i) a hydrogel shell and (ii) an alginate core containing a population of genetically-engineered cells that comprise a second inducible promoter operably linked to a nucleic acid encoding a second product of interest, wherein activity of the second inducible promoter is modulated by the first product of interest.

Further provided herein, in some embodiments, are compositions comprising (a) an environmental sample comprising at least one contaminant, and (b) a hydrogel-alginate capsule comprising a hydrogel shell and an alginate core containing a population of genetically-engineered cells that comprise an inducible promoter operably linked to a nucleic acid encoding a product of interest, wherein activity of the inducible promoter is modulated by the at least one contaminant.

Yet other embodiments provide method comprising (a) combining a culture of genetically-engineered cells with alginate to produce droplets, (b) crosslinking the droplets with calcium ions to form spheres containing the genetically-engineered cells, and (c) encapsulating the spheres with a hydrogel to form a capsule, wherein the genetically-engineered cells comprise a promoter operably linked to a nucleic acid encoding a product of interest.

BRIEF DESCRIPTION OF THE DRAWINGS

FIG. 1A: Schematic of core-shell encapsulation of cells. Droplets of 2.5% alginate with engineered *E. coli* were crosslinked in a calcium solution to form the soft core of the beads, which were then coated with a layer of alginate/polyacrylamide to form a tough hydrogel shell. FIG. 1B: Hydrogel beads were subjected to 10% (red), 20% (green), and 40% (blue) compressive strains. The average maxi-mum strain and force before fracture were 25.84% and 0.108 N, respectively (n=14). FIG. 1C: Encapsulated bacteria escaped from non-coated beads at high rates but did not escape from coated beads at detectable levels (shows that tough hydrogel encapsulation provides physical containment). FIG. 1D: Survival rates after subjecting beads or liquid cultures to various types of environmental challenges such as antibiotics (30 µg/ml kanamycin for 6 hours), extreme pH (pH 3 for 1 hour), and extreme temperatures (−80° C. freezing for 2 hours) normalized to untreated control groups (demonstrates that tough hydrogel encapsulation provides protection against a range of environmental stresses). FIG. 1E illustrates living cells retrieval through bead homogenization and serial dilutions. Retrieval is almost 100%.

FIGS. 2A-2C show responses of encapsulated bacterial cells to external stimuli. FIG. 2A: Left: GFP expression under the control of an IPTG-inducible promoter. Right: Confocal images of beads encapsulating the IPTG-sensing *E. coli* strain with and without 1 mM IPTG (demonstrates that tough hydrogel encapsulation allows small molecule inducers to diffuse into the core and induce protein expression). FIG. 2B: Left: An improved SCRIBE strain using CRISPRi to knockdown cellular exonucleases (xonA and recJ) for enhanced genome editing efficiency via SCRIBE in DH5αPRO. Right: Recombinant frequencies of beads containing the high efficiency SCRIBE strain induced for a total of 24 hours with or without aTc and IPTG. FIG. 2C: Left: AHL sender strain responds to aTc and produces AHL as an output, which later reaches the AHL receiver strain through diffusion and induces GFP expression. Right: Cells retrieved from receiver beads showed various levels of induction corresponding to different AHL sender bead:AHL receiver bead ratios.

FIG. 3A: Survival rates of encapsulated GRO in beads pre-soaked (closed circles)/not pre-soaked (open circles) in LB+1 mM pIF 0.2% L-ara before incubation in LB. Survival rates were calculated by normalizing colony forming units (CFU) at each time point to CFU at 0 h. Insets show visual differences between the cores in the two experimental groups after 24 hours of incubation, which corresponded to different levels of bacterial cell death. Serial dilutions corresponding to the curves are shown at the bottom. FIG. 3B: The supernatants after 6 days of incubation were plated and showed no detectable escape (<200 CFU/mL, n=10) FIG. 3C: Escape rate of broken GRO beads in 10 mL of LB. Escape rate is calculated as the ratio of CFU escape over the initial number ($\sim 5*10^4$ cells per bead) of bacteria encapsulated (limit of detection: 200 CFU/mL) (n=3).

FIG. 4A: Flow cytometry analysis of heavy metal sensing strain. After a 3-hour incubation, beads were exposed to 300 µM ZnCl2, 100 µM Pb(NO3)2, and 1 µM CdCl2 in LB medium, respectively. FIG. 4B: Response of encapsulated heavy metal ion sensing strain to 0 µM, 0.5 µM, 5 µM, 50 µM, and 500 µM CdCl2 after 3 hours of incubation. FIG. 4C: Photo-graph of the heavy metal sensing experiment setup (top). Tea bags containing five beads each were incubated in beakers containing Charles River water with and without 5 mM CdCl2 (below the 1 mg/L toxic limit defined by the Massachusetts Department of Environmental Protection). Beads retrieved after 6 hours showed green fluorescence (bottom). FIG. 4D: Flow cytometry analysis of encapsulated cells responding to cadmium ions in Charles River water.

FIG. 5A is a schematic and graph depicting SCRIBEs and FIG. 5B shows their performance in tough hydrogel.

FIG. 6A is a schematic illustration of a generic structure for living materials and devices. Layers of robust and biocompatible hydrogel and elastomer were assembled and bonded into a hybrid structure, which can transport sustained supplies of water, nutrient and oxygen to genetically engineered cells at hydrogel-elastomer interface. Communication between different types of cells and with the environment was achieved by diffusion of small molecules in hydrogels. FIG. 6B is a schematic illustration of the high stretchability and high robustness of the hydrogel-elastomer hybrids that prevent cell leakage from the living device, even under large deformations. Images shows that the living device can sustain uniaxial stretching over 1.8 times and twisting over 180° while maintaining its structural integrity. FIG. 6C shows viability of bacterial cells at room temperature over 3 days. The cells were kept in the device placed in the humid chamber without additional growth media (light gray, middle line), in the device immersed in the growth media (dark gray, bottom line) as a control, and in growth media as another control (black, top line). N=3 repeats. FIG. 6D shows $OD_{600}$ and streak plate results (inset images) of the media surrounding the defective devices (yellow) and intact devices at different times after once (black) or 500 times (gray) deformation of the living devices and immersion in media. N=3 repeats.

FIG. 7A is a schematic illustration of a hydrogel-elastomer hybrid with four isolated chambers to host bacterial strains, including $DAPG_{RCV}$/GFP, $AHL_{RCV}$/GFP, $IPTG_{RCV}$/GFP, and $Rham_{RCV}$/GFP, respectively. Signaling molecules diffused from the environment through the hydrogel window into cell chambers, where they were detected by the bacteria. FIG. 7B: Genetic circuits were constructed in bacterial strains to detect cognate inducers (i.e., DAPG, AHL, IPTG, and Rham), and produce GFP.

FIG. 7C: Images of living devices after exposure to individual or multiple inputs. Cell chambers hosting bacteria with the cognate sensors showed green fluorescence while the non-cognate bacteria in chambers were not fluorescent. Scale bars are shown in images.

FIG. 8A is a schematic illustration of a living device that contains two cell strains: the transmitters (aTc$_{RCV}$/AHL strain) produce AHL in the presence of aTc, and the receivers (AHL$_{RCV}$/GFP strain) express GFP in the presence of AHL. The transmitters could communicate with the receivers via diffusion of the AHL signaling molecules through the hydrogel window, even though the cells are physically isolated by elastomer. FIG. 8B: Quantification of normalized fluorescence over time. N=3 repeats. All data were measured by flow cytometry with cells retrieved from the device at different times. FIG. 8C: Images of device and microscopic images of cell chambers 6 h after addition of aTc into the environment surrounding the device. The side chambers contain transmitters, while the middle one contains receivers. FIG. 8D: Images of device and microscopic images of cell chambers, 6 h after aTc addition in the environment. The side chambers contain aTc$_{RCV}$/GFP instead of transmitters, while middle one contains receivers. Scale bars are shown in images.

FIGS. 9A-9H show living wearable devices. FIG. 9A is a schematic illustration of a living patch. The patch adhered to the skin with the hydrogel side and the elastomer side was exposed to the air. Engineered bacteria inside can detect signaling molecules. FIGS. 9B-9D: Rham solution was smeared on skin and the sensor patch was conformably applied on skin. The channels with Rham$_{RCV}$/GFP in the living patch became fluorescent, while channels with AHL-$_{RCV}$/GFP did not show any differences. Scale bars are shown in images. FIG. 9E: Schematic illustration of a glove with chemical detectors robustly integrated at the fingertips. Different chemical-inducible cell strains, including IPTG$_{RCV}$/GFP, AHL$_{RCV}$/GFP, and Rham$_{RCV}$/GFP, were encapsulated in the chambers. FIGS. 9F-9H: When the living glove was used to grab a wet cotton ball containing the inducers, GFP fluorescence was shown in the cognate sensors on the gloves. In contrast, the non-cognate sensor did not show any fluorescence. Scale bars are shown in images.

FIG. 10A is a schematic illustration of the diffusion of signaling molecules from the environment through the hydrogel to cell chambers in the living device. FIG. 10B: Diagram of GFP expression after induction with a small-molecule chemical. FIG. 10C: Inducer concentration profile throughout the hydrogel window and cell chamber at different times. FIG. 10D: Typical inducer concentration in the cell chamber as a function of time. FIG. 10E: The normalized fluorescence of different cell strains as a function of time after addition of inducer. N=3 repeats. Dots represent experimental data, and curve represents model.

FIG. 11A: Bacteria were injected into the cavities at the hydrogel-elastomer interface with metallic needles from the hydrogel side. FIG. 11B: Injection holes were sealed on hydrogel-elastomer device with drops of fast-curable pre-gel solution. FIG. 11C: Hydrogel-elastomer device with fully encapsulate bacteria was obtained.

FIGS. 18A-18B show living patch control experiments. FIG. 18A: When no inducer was smeared on skin and the living sensor patch was adhered on skin conformably, the channels with Rham$_{RCV}$/GFP and AHL$_{RCV}$/GFP in the living patch did not show any differences. FIG. 18B: When both inducers Rham and AHL was smeared on skin and the living patch was applied, the channels with Rham$_{RCV}$/GFP and AHL$_{RCV}$/GFP in the living patch became fluorescent. Scale bars are shown in images.

FIG. 19A: Schematic illustration of the hydrogel-elastomer hybrid sensor patch have anti-dehydration property over pure hydrogel device. The silicone elastomer cover effectively prevents evaporation of water from the hydrogel and dehydration of the living patch. FIG. 19B: Time-lapse snapshots of hydrogel-elastomer hybrid sensor patch (left) and pure hydrogel sensor patch (right) mounted on a plastic beaker at room temperature with low humidity (25° C. and 50% relative humidity) for 24 h. The elastomer outlayer of the hydrogel-elastomer hybrid device significantly slowed down the dehydration process of the hydrogel and provided a sustained humid environment for encapsulated cells for over 24 h. On the other hand, distorted channels became apparent on patches made of pure hydrogels when they were exposed to air for 6 h due to dehydration.

FIG. 20A: Schematic illustration of signaling molecule diffusion from the environment through the hydrogel in the living device. Cells were embedded in a segment of the hydrogel close to the elastomer wall. FIG. 20B: Comparison of typical inducer concentration profiles when cells were embedded in hydrogel ($I(L,t)/I_0$) versus cells in medium of the cell chamber ($I(L_g+L_c/2,t)/I_0$). Despite small deviation (<12%) due to the diffusivity differences between hydrogel and medium and distance variation in two cases, it can be seen that the profile in the simplified model can consistently represent the typical concentration profile in the cell chamber of the living sensor at any time.

Figure 1A:
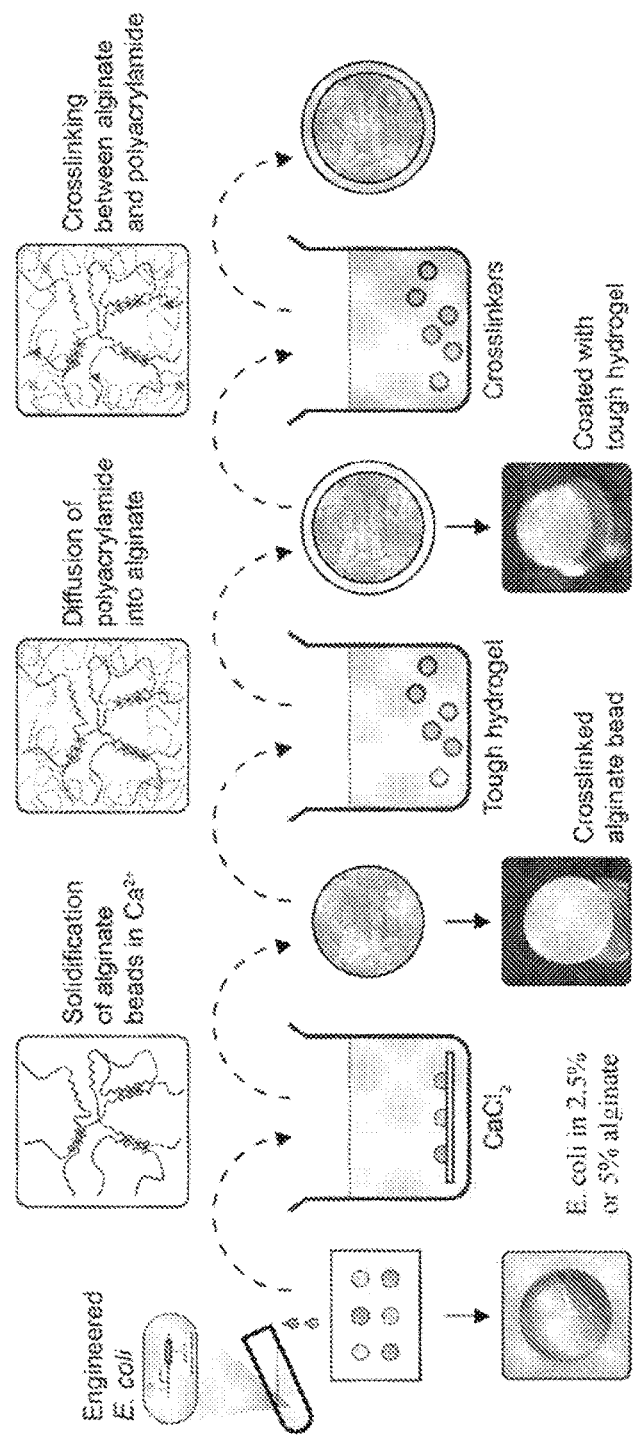
FIGS. 1A-1D show the encapsulation of living cells in tough hydrogel beads.

and its approximate solution. The pre-factor in $$t_{\mathit{diffuse}} = [\Lambda(K/I_0)]^{-2}\frac{L^2}{D_g}$$

is fitted into a power law that approximately gives $$t_{\mathit{diffuse}} \approx \frac{4}{9}\left(\frac{I_0}{K}-1\right)^{-0.56}\frac{L^2}{D_g}.$$

DETAILED DESCRIPTION

The integration of genetically programmed cells into materials and devices enables the power of biology to be harnessed for a wide range of scientific research and technological applications. Stretchable, robust and biocompatible hydrogel-elastomer hybrids to host genetically programmed bacteria are described herein, thus creating a set of stretchable and wearable living materials and devices that possess unprecedented functions and capabilities. A quantitative yet generic model was also developed to account for the coupled physical and biochemical processes in living materials and devices. This new and simple strategy for designing living materials and devices not only provides new tools for research in synthetic biology but also enables novel applications such as living sensors, interactive genetic circuits, and living wearable devices.

Genetically engineered cells enabled by synthetic biology have accomplished multiple programmable functions, including sensing (1), responding (2), computing (3), and recording (4). Powered by this emerging capability to program cells into living computers (1-6), the integration of genetically encoded cells into freestanding materials and devices not only provides new tools for scientific research but also lead to unprecedented technological applications (7). The development of such living materials and devices has been significantly hampered by the demanding requirements for maintaining viable and functional cells in materials and devices, plus biosafety concerns towards the release of genetically modified organisms into environments. For example, gene networks embedded in paper matrices have been utilized for low-cost rapid viruses detection and protein manufacturing (1). Their gene networks, however, are based on freeze-dried extracts from genetically engineered cells to operate, partially because the paper substrates cannot sustain long-term viability and functionality of living cells or prevent their leakage. As another example, by seeding cardiomyocytes on thin elastomer films, bio-hybrid devices have been developed as soft actuators (8) and biomimetic robots (9). Nonetheless, since the cells are not protected or isolated from the environment, the bio-hybrid devices need to operate in media and the cells may detach from the elastomer films.

Thus, prior to the present disclosure, it was a challenge to integrate genetically encoded cells into practical materials and devices that can maintain long-term viability and functionality of the cells, allow for efficient chemical communications between cells and with external environments, and prevent cells from escaping the materials or devices. A versatile material system and a general method to design living materials and devices capable of diverse functions (1, 8-10) were a critical need in the field.

As polymer networks infiltrated with water, hydrogels have been widely used as scaffolds for tissue engineering (11) and vehicles for cell delivery (12), owning to their high water content, biocompatibility, bio-functionality, and permeability to a wide range of chemicals and biomolecules (13). The success of hydrogels as cell carriers in tissue engineering and cell delivery demonstrates their potential as an ideal matrix for living materials and devices to incorporate genetically engineered cells. Common hydrogels, however, exhibit low mechanical robustness (14) and difficulty in bonding with other materials and devices (15), which have posed challenges in using them as matrices for living materials and devices (10). Significant progress has been made towards designing hydrogels with high mechanical toughness and stretchability (14, 16, 17) and robustly bonding hydrogels to engineering materials such as glass, ceramics, metals, and elastomers (15, 18, 19). Combining programmed cells with robust biocompatible hydrogels, as provided herein, enables an avenue to create new living materials and devices.

Demonstrated herein is the design of a set of living materials and devices based on stretchable, robust and biocompatible hydrogel-elastomer hybrids that host various types of genetically engineered bacterial cells. As shown herein, the hydrogels can sustainably provide water and nutrients to the cells, while the elastomers ensure sufficient air permeability to maintain viability and functionality of the bacteria. Communication between different types of genetically engineered cells and with the environment was achieved via transportation of signaling molecules in hydrogels. The high stretchability and robustness of the hydrogel-elastomer hybrids prevent leakage of cells from the living materials and devices under repeated deformations.

Novel applications uniquely enabled by the described living materials and devices are demonstrated, including stretchable living sensors responsive to multiple chemicals, interactive genetic circuits, a living patch that senses chemicals on the skin, and a glove with living chemical detectors integrated at the fingertips. A quantitative model that couples transportation of signaling molecules and responses of cells was further developed to help the design of future living materials and devices.

As disclosed herein, genetically engineered cells have been integrated as programmable functional components with stretchable, robust and biocompatible hydrogel-elastomer hybrids to create a set of stretchable living materials and devices. These living materials and devices can be programmed with desirable functionalities by designing the genetic circuits in the cells as well as the structures and micro-patterns of the hydrogel-elastomer hybrids. Moreover, a quantitative model was developed that accounts for the coupling between physical and biochemical processes in living materials. Further, two critical time scales were identified that determine the speed of response of the living materials and devices, and provide guidelines for the design of future systems. This work has the potential to open new technological avenues that capitalize on advances in synthetic biology and soft materials to implement stretchable, wearable and portable living systems with important applications in the monitoring of human health (1) and environmental conditions (35), and the treatment and prevention of diseases (2).

Further, genetically modified microorganisms (GMMs) are being developed and used for bioremediation, agriculture, mining, and the production of biofuels and pharmaceuticals. The potential for GMMs to escape into the environment, however, has created a need for strategies to contain these organisms and prevent their uncontrolled release. Since 1985, the US Environmental Protection Agency has issued only a handful of experimental use permits for engineered microorganisms and has registered only a few, mostly for heat-killed bacteria with insecticidal effects.

Biological biocontainment involves biological barriers impeding the escape and survival of microorganisms in the environment. Hydrogels are desirable materials for encapsulating living cells as they provide an aqueous environment that can be infused with chemicals, allowing cell growth, sensing, and protection against environmental hazards. Alginate forms hydrogels in the presence of di-cationic solutions (e.g., $Ca^{2+}$, $Ba^{2+}$) and has been used in various biomedical applications due to its low cost, negligible toxicity, and mild gelation conditions.

Described herein is a physical strategy for the containment of GMMs using robust hydrogels that resulted in virtually no escape of cells into the surrounding environment. GMMs were encapsulated in a core-shell hydrogel structure that enables retrieval of cells from the system by peeling and homogenization. This technology was harnessed to protect encapsulated cells against a number of chemical and physical stresses such as antibiotics, low pH, and freezing. In addition, it was demonstrated that encapsulated cells divide, stay metabolically active, and sense and respond to environmental stimuli via heterologous gene circuits. Encapsulated cells were equipped with a genomically-encoded memory system, SCRIBE (Farzadfard, T. K. Lu, Science 346, 1256272 (2014)) and could record information about chemical exposure. Furthermore, encapsulated cells could generate and respond to quorum-sensing molecules, thus allowing for cell-cell communication between bacteria in distinct encapsulated beads. As an additional safeguard layer, chemical containment was demonstrated by encapsulating a genomically-recoded organism (GRO Escherichia coli) and tuning the lifespan of the GRO by changing the amount of synthetic amino acid incorporated into the beads. Finally, functional bacterial sensors were constructed, which detected toxic heavy metals spiked into water samples. This tough hydrogel-based strategy for physical biocontainment enables deployment of GMMs for a variety of applications while mitigating concerns regarding environmental escape.

While biological containment strategies are crucial to biosafety, physical containment remains the principal means that currently allows handling of GMMs as intrinsic containment strategies always have non-zero mutation escape rates. So far, the only commercially available GMMs used as environmental sensors are confined in a sealed vial in which samples are injected manually. To unleash the potential of biosensor and bioremediation devices for time-course monitoring and interacting with surrounding environment, there is a need for smart vehicles to deploy GMMs for long-term autonomous in situ detection. Hydrogel scaffolds provide a highly-hydrated environment to sustain cell growth by allowing small molecules to diffuse between the interior and exterior of the device, thus serving as an ideal vehicle for GMM delivery. Although previous work showed the long-term physical containment of bacteria by core-shell hydrogel microparticles, it did not demonstrate biological activity. No reports have yet shown near-perfect physical containment that still permits sensing and cell growth, thus making population-based microbial devices (such as SCRIBE) impossible for deployment in the field.

Provided herein is a hydrogel-based encapsulation system that incorporates both physical and chemical biocontainment strategies for safe deployment of engineered organisms. As the data herein shows, the tough shell conferred mechanical resistance to the underlying soft core where the cells were contained. The alginate core provided nutrients to sustain bacterial growth, and a second layer of containment was achieved by incorporating a GRO that only grows in the presence of a synthetic amino acid. Changing the synthetic amino acid concentration within the hydrogels enabled fine-tuning of the lifespan of the GRO. This "biological timer" system eliminated potential bacterial growth outside the bead even when the hydrogel shell was purposely compromised. This is the first description of an approach that combines dual chemical and physical safeguards to achieve near-perfect biocontainment. The data provided herein also demonstrated that encapsulated cells could be genetically engineered to respond to environmental stimuli in a programmed fashion. Finally, heavy-metal-sensing bacteria were incorporated into the hydrogel beads and then tested under real-world conditions to show successful detection of cadmium ions in water samples.

This containment platform could thus lead to in vitro and in vivo deployment of synthetic biology tools. Just as toxicity fingerprinting of an industrial contaminant can be detected with a simple optical readout, the same hydrogel beads encapsulating other biosensing strains could detect TNT explosives in military settings or monitor exposure time to chemicals with population-level readout such as that obtained with SCRIBE. The design of the hydrogel can be easily adapted to the intended application. For example, sheet-geometry core-shell structures were fabricated, which could be used on the skin to sense small molecules produced by common pathogens such as Pseudomonas aeruginosa, thus detecting infection at an early stage. Automating the manufacturing process will provide precise control of the device geometries to accommodate various physical environments and improve the scalability of the platform. Further, implementing a selective diffusion barrier and/or an extreme-pH resistance capability in the hydrogels to help encapsulated microbial populations survive in harsh environments such as the human gut, where they would be able to detect disease-relevant biomarkers.

By combining two types of hydrogels into a core-shell structure, the present disclosure provides a reliable strategy for the environmental deployment of microbial biosensors. This platform can prolong and control cell viability, prevent bacterial escape, and allow the detection at low levels of contaminants, all of which facilitate GMM use for bioremediation and biomonitoring.

Compositions

Provided herein are hydrogel-elastomer compositions encapsulating a population of genetically-engineered cells that comprise a promoter operably linked to a nucleic acid encoding a product of interest.

A hydrogel-elastomer composition is a hybrid composition comprising both a hydrogel and an elastomer. The biocompatible hydrogel is designed to provide sustainable supplies of water and nutrients and the elastomer is air permeable, maintaining long-term viability and functionality of encapsulated cells. In some embodiments, layers of the hydrogel and elastomer are bonded (e.g., covalently or non-covalently) together to form a physically-crosslinked hydrogel. Following assembly of the hydrogel and elastomer, the physically-crosslinked hydrogel may be UV irradiated.

In some embodiments, the hydrogel of a hydrogel-elastomer composition is comprised of polyacrylamide (PAAm)-alginate. Thus, the hydrogel may be comprised of polyacrylamide (PAAm) and alginate (polyacrylamide (PAAm)-alginate). In some embodiments, the PAAm is covalently crosslinked PAAm. To produce a PAAm network in hydrogel, acrylamide may be used as the monomer, N,N-methylenebisacrylamide may be used as the crosslinker, and 2-hydroxy-4'-(2-hydroxyethoxy)-2-methylpropriophenone may be used as the photoinitiator, for example. In some embodiments, the alginate is ionically crosslinked alginate. For example, a calcium sulfate slurry may be used as the ionic crosslinker with sodium alginate to produce dissipative networks.

A hydrogel of a hydrogel-elastomer composition, in some embodiments, is infused with nutrients to support cell growth and/or survival/maintenance. This can be achieved, for example, by infusing the hydrogel with cell culture media, which includes nutrients such as growth factors, cytokines, hormones, vitamins, carbon sources and/or nitrogen sources.

The elastomer of a hydrogel-elastomer composition, in some embodiments, is comprised of silicone. Thus, the elastomer may contain a silicone such as polydimethylsiloxane (PDMS) (e.g., SYLGARD® 184) and/or platinum-catalyzed silicone (e.g., ECOFLEX® (Smooth-On)). In some embodiments, the silicone is molded and activated with benzophenone. In some embodiments, elastomers with microstructures cavities are prepared, e.g., by soft lithography, with a feature size of 400-600 μm in width and 100-300 μm in depth. In some embodiments, elastomers with microstructures cavities are prepared with a feature size of 500 μm in width and 200 μm in depth. In some embodiments, the elastomer is air-permeable, which permits the exchange of gases through the elastomer (elastomer layer). Thus, in some embodiments, the elastomer is microporous (e.g., containing pores with diameters less than 2 nm).

Hydrogel-elastomer compositions encapsulate (surround) a (at least one) population of genetically-engineered cells. That is, the cells are incorporated into the hydrogel-elastomer composition such that they are not freely exposed to the environment. Typically, the hydrogel provides sustainable supplies of water and nutrients and the elastomer is air permeable, maintaining long-term viability and functionality of the encapsulated cells.

In some embodiments, a hydrogel-elastomer composition is capable of sustaining a uniaxial stretch over (greater than) 1.5 times its original length and a twist over 180° while maintaining its structural integrity. In some embodiments, a hydrogel-elastomer composition is capable of sustaining a uniaxial stretch over 1.8 times its original length and a twist over 180° while maintaining its structural integrity. In some embodiments, a hydrogel-elastomer composition is capable of sustaining a uniaxial stretch over 2 times its original length and a twist over 180° while maintaining its structural integrity.

Also provided herein are hydrogel-alginate compositions, for example, in the shape of a capsule (bead/bead-like structure) comprising a (tough) hydrogel shell and an alginate core containing a population of genetically-engineered cells that comprise a promoter operably linked to a nucleic acid encoding a product of interest. In this core-shell capsule, the alginate core supports growth, in some embodiments, by supplying nutrients, while the hydrogel shell provides mechanical protection for the entire capsule.

In some embodiments, genetically-engineered cells are incorporated into the hydrogel-alginate capsules in a liquid culture with alginate into droplets that are crosslinked with calcium ions, for example, to form spheres. The cell-containing alginate hydrogel may then be cast into different shapes These cores may then be coated with a polyacrylamide-alginate hydrogel layer.

In some embodiments, the hydrogel of a hydrogel-alginate composition is comprised of polyacrylamide (PAAm)-alginate. Thus, the hydrogel may be comprised of polyacrylamide (PAAm) and alginate (polyacrylamide (PAAm)-alginate). In some embodiments, the PAAm is covalently crosslinked PAAm. To produce a PAAm network in hydrogel, acrylamide may be used as the monomer, N,N-methylenebisacrylamide may be used as the crosslinker, and 2-hydroxy-4'-(2-hydroxyethoxy)-2-methylpropriophenone may be used as the photoinitiator, for example. In some embodiments, the alginate is ionically crosslinked alginate. For example, a calcium sulfate slurry may be used as the ionic crosslinker with sodium alginate to produce dissipative networks.

In some embodiments, the hydrogel shell comprises pores having a pore size of 50 nm or less. For example, the pore size may be 5-50 nm (e.g., 5, 10, 15, 20, 25, 30, 35, 40, 45 or 50 nm).

The alginate core of a hydrogel-alginate composition/capsule, in some embodiments, is infused with nutrients to support cell growth and/or survival/maintenance. This can be achieved, for example, by combining the alginate with cell culture media (e.g., containing genetically-engineered cells), which includes nutrients such as growth factors, cytokines, hormones, vitamins, carbon sources and/or nitrogen sources.

Hydrogel-alginate capsules provide tough mechanical properties and can serve as a containment mechanism. Thus, in some embodiments, the capsule exhibits no bacterial escape when incubated in media for 72 hours (or at least 72 hours) at 37° C.

The hydrogel-alginate capsules also have resistance to many physical, chemical, and biological stresses. Thus, in some embodiments, the genetically-engineered cells have a survival rate that is at least 30-fold (e.g., at least 35, 40, 45, 50, 55, 60, 65, 70, 75, 80, 85, 90, 95 or 100-fold) greater than the survival rate of planktonic (free) cells following exposure to an antibiotic or an acidic environment. In some embodiments, the genetically-engineered cells have a survival rate that is at least 50-fold greater than the survival rate of planktonic cells following exposure to an antibiotic or an acidic environment. Planktonic cells are cells (e.g., bacterial cells) that grow unattached to a substrate (e.g., a biofilm). In some embodiments, the genetically-engineered cells have a survival rate that is at least 100-fold greater than the survival rate of planktonic cells following exposure to an antibiotic or an acidic environment. Acid environments typically have a pH value of less than 7. In some embodiments, the acidic environment has a pH value of 2-5. In some embodiments, the acidic environment has a pH value of 3.

In some embodiments, genetically-engineered cells encapsulated within the hydrogel-alginate capsules are metabolically active within the alginate core of the capsule. Cells are considered mitotically active if they are capable of growth/cell division. In some embodiments, the cells (e.g., at least 10, 20, 30, 40, 50, 60, 70, 80, 90% of the cells) within the alginate core of the capsules are mitotically active. For example, the number of cells may increase by at least $10^5$ fold (at least 16 generations) and reach stationary phase following 12 hours of incubation.

Given the permeable nature of the hydrogel capsules, chemical containment may be used to add a layer of control over encapsulated cells. Thus, in some embodiments, the genetically-engineered cells are auxotrophic for at least one nutrient or other agent. That is, the cells may be engineered to require a certain nutrient for cell survival such that if the cell escapes from the capsule, the cell will die, in the absence of the required nutrient. For example, the at least one nutrient may be an amino acid (e.g., synthetic amino acid p-azido-phenylalanine).

Compositions as provided herein may be used to test samples, for example, for contaminants. Thus, in some embodiments, the present disclosure provides compositions comprising (a) a sample, such as an environmental sample, comprising at least one contaminant, and (b) a hydrogel-alginate capsule comprising a hydrogel shell and an alginate core containing a population of genetically-engineered cells that comprise an inducible promoter operably linked to a nucleic acid encoding a product of interest, wherein activity of the inducible promoter is modulated by the at least one contaminant.

In some embodiments, the environmental sample is a water sample. In some embodiments, the environmental sample is a soil sample. Other environmental samples may be used. For example, the sample may be a biological sample, such as sweat, saliva, blood, urine or cerebrospinal fluid.

In some embodiments, the at least one contaminant comprises a heavy metal. For example, the heavy metal may comprise cadmium ions, zinc and/or lead.

In some embodiments, the product of interest is a reporter molecule (e.g., fluorescent molecule).

Further provided herein are systems comprising hydrogel-alginate encapsulated cells that are capable of communicating with each other, for example, via small molecule quorum sensing. Thus, the systems may comprise (a) a first population of hydrogel-alginate capsules comprising (i) a hydrogel shell and (ii) an alginate core containing a population of genetically-engineered cells that comprise a first inducible promoter operably linked to a nucleic acid encoding a first product of interest, and (b) a second population of hydrogel-alginate capsules comprising (i) a hydrogel shell and (ii) an alginate core containing a population of genetically-engineered cells that comprise a second inducible promoter operably linked to a nucleic acid encoding a second product of interest, wherein activity of the second inducible promoter is modulated by the first product of interest. In some embodiments, the first and/or second product of interest is a quorum-sensing molecule. In some embodiments, the second product of interest is a reporter molecule (e.g., fluorescent protein). These systems may include more than two populations of hydrogel-alginate capsules, each population comprising a different population of cells, each population of cells comprising a different genetic circuit (promoter operably linked to a nucleic acid encoding a product of interest).

Genetically-engineered cells as provided herein may be prokaryotic cells (e.g., bacterial cells) or eukaryotic cells (e.g., yeast or mammalian cells).

In some embodiments, the cells are bacterial cells. Examples of bacterial cells of the present disclosure include, without limitation, cells from *Yersinia* spp., *Escherichia* spp., *Klebsiella* spp., *Acinetobacter* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Streptomyces* spp., *Bacteroides* spp., *Prevotella* spp., *Clostridium* spp., *Bifidobacterium* spp., and/or *Lactobacillus* spp. In some embodiments, the bacterial cells are from *Bacteroides thetaiotaomicron, Bacteroides fragilis, Bacteroides distasonis, Bacteroides vulgatus, Clostridium leptum, Clostridium coccoides, Staphylococcus aureus, Bacillus subtilis, Clostridium butyricum, Brevibacterium lactofermentum, Streptococcus agalactiae, Lactococcus lactis, Leuconostoc lactis, Actinobacillus actinobycetemcomitans, cyanobacteria, Escherichia coli, Helicobacter pylori, Selnomonas ruminatium, Shigella sonnei, Zymomonas mobilis, Mycoplasma mycoides, Treponema denticola, Bacillus thuringiensis, Staphylococcus lugdunensis, Leuconostoc oenos, Corynebacterium xerosis, Lactobacillus plantarum, Lactobacillus rhamnosus, Lactobacillus casei, Lactobacillus acidophilus, Streptococcus* spp., *Enterococcus faecalis, Bacillus coagulans, Bacillus ceretus, Bacillus popillae, Synechocystis* strain PCC6803, *Bacillus liquefaciens, Pyrococcus abyssi, Selenomonas nominantium, Lactobacillus hilgardii, Streptococcus ferus, Lactobacillus pentosus, Bacteroides fragilis, Staphylococcus epidermidis, Zymomonas mobilis, Streptomyces phaechromogenes,* and/or *Streptomyces ghanaenis*. In some embodiments, the cells are *Escherichia coli* cells.

In some embodiments, the cells are mammalian cells. Examples of mammalian cells of the present disclosure include, without limitation, human embryonic kidney (HEK) cells, HeLa cells, cancer cells from the National Cancer Institute's 60 cancer cell lines (NCI60), DU145 (prostate cancer) cells, Lncap (prostate cancer) cells, MCF-7 (breast cancer) cells, MDA-MB-438 (breast cancer) cells, PC3 (prostate cancer) cells, T47D (breast cancer) cells, THP-1 (acute myeloid leukemia) cells, U87 (glioblastoma) cells, SHSY5Y human neuroblastoma cells (cloned from a myeloma) and/or Saos-2 (bone cancer) cells.

Cells of the present disclosure, in some embodiments, are engineered to include genetic circuits. Thus, engineered cells may comprise a (at least one) promoter operably linked to a (at least one) nucleic acid encoding a product of interest (e.g., a nucleic acid or protein of interest).

A "promoter" refers to a control region of a nucleic acid sequence at which initiation and rate of transcription of the remainder of a nucleic acid sequence are controlled. A promoter may also contain sub-regions at which regulatory proteins and molecules may bind, such as RNA polymerase and other transcription factors. Promoters may be constitutive, inducible, activatable, repressible, tissue-specific or any combination thereof. A promoter drives expression or drives transcription of the nucleic acid sequence that it regulates. Herein, a promoter is considered to be "operably linked" when it is in a correct functional location and orientation in relation to a nucleic acid sequence it regulates to control ("drive") transcriptional initiation and/or expression of that sequence. In some embodiments, a coding nucleic acid sequence may be positioned under the control of a recombinant or heterologous promoter, which refers to a promoter that is not normally associated with the encoded sequence in its natural environment.

In some embodiments, inducible promoters such as pLtetO, which is induced by anhydrotetracycline (aTc), or pLlacO, which is induced by isopropyl β-D-1-thiogalactopyranoside (IPTG) (Lutz et al., *Nucleic Acids Res* 25:1203 (1997)) are used.

Engineered cells may also be referred to as modified cells. A modified cell is a cell that contains an exogenous nucleic acid or a nucleic acid that does not occur in nature (e.g., an engineered nucleic acid). In some embodiments, an engineered cell contains an exogenous independently replicating nucleic acid (e.g., an engineered nucleic acid present on an episomal vector) or a chromosomal modification. In some embodiments, an engineered cell is produced by introducing a foreign or exogenous nucleic acid into the cell.

The population of cells encapsulated within a hydrogel-elastomer composition may be a homogeneous population (e.g., all the same cell type expressing the same genetic circuit) or a heterogeneous population (e.g., all the same cell type expressing different genetic circuits, or different cell types expressing the same genetic circuit, or difference cell types expressing difference genetic circuits). In some embodiments, the heterogeneous population comprises subsets of cells, each subset comprising a different promoter relative to the other subsets of the population. Thus, population A (e.g., bacterial cells) may include promoter A operably linked to a nucleic acid encoding a product of interest, while population B (e.g., also bacterial cells) may include promoter B operably linked to a nucleic acid encoding a product of interest.

In some embodiments, the genetic circuits are cascading circuits such that the activity of (e.g., activation of) one circuit depends on the activity of an upstream circuit. Thus, in some embodiments, one subset of genetically-engineered cells of the population comprises a first inducible promoter operably linked to a nucleic acid encoding a first product of interest, and another subset of genetically-engineered cells of the population comprises a second inducible promoter operably linked to a nucleic acid encoding a second product of interest, wherein activity of the second inducible promoter is modulated by the first product of interest. For example, the first product of interest produced by the first population of cells may be a quorum-sensing molecule that modulates activity of the second inducible promoter within the second population of cells.

Quorum sensing, generally, is a system of stimuli and response correlated to population density. Quorum sensing typically enables bacteria to restrict the expression of specific genes to the high cell densities at which the resulting phenotypes will be most beneficial. Bacteria use quorum sensing to coordinate certain behaviors such as biofilm formation, virulence, and antibiotic resistance, based on the local density of the bacterial population. Exemplary, non-limiting, classes of quorum-sensing signaling molecules are oligopeptides in Gram-positive bacteria, N-acyl homoserine lactones (AHL) in Gram-negative bacteria, and a family of autoinducers known as autoinducer-2 (AI-2) in both Gram-negative and Gram-positive bacteria.

Wearable, Digestible and/or Implantable Devices

Aspects of the present disclosure provide wearable (or ingestible or implantable) devices comprising hydrogel-elastomer compositions. A wearable device, in some embodiments, is made to be worn (e.g., place on or secured to) on the surface of a subject's body, such as on the skin (e.g., stomach, hand, arm, leg or foot). Examples of wearable devices as provided herein include, but are not limited to, skin (dermal) patches and gloves.

The present disclosure, in some embodiments, provides skin patches that include a first layer comprising a hydrogel containing genetically-engineered cells and a second layer comprising an elastomer. In some embodiments, the hydrogel is infused with cell nutrients. In some embodiments, the elastomer is air-permeable.

In some embodiments, the elastomer is comprised of silicone. For example, the silicone may be polydimethylsiloxane (PDMS) or a platinum-catalyzed silicone (e.g., ECO-FLEX® silicone). In some embodiments, the elastomer is microporous.

In some embodiments, the population of genetically-engineered cells is a heterogeneous population. In some embodiments, the heterogeneous population comprises subsets of cells, each subset comprising a different promoter relative to the other subsets of the population. For example, one subset of genetically-engineered cells of the population may comprise a first inducible promoter operably linked to a nucleic acid encoding a first product of interest, and another subset of genetically-engineered cells of the population may comprise a second inducible promoter operably linked to a nucleic acid encoding a second product of interest, wherein activity of the second inducible promoter is modulated by the first product of interest.

In some embodiments, the genetically-engineered cells are genetically-engineered bacterial cells. Other cell types may be used.

Skin patches, and other wearable devices of the present disclosure, may include a hydrogel-elastomer comprising a population of cells genetically-engineered to respond to secretions from the body. For example, activity of an inducible promoter of a genetic circuit within an engineered cell may be modulated by a cognate inducer present in skin, sweat or blood of a subject. In the presence of a cognate inducer, the cells may produce a therapeutic molecule or a prophylactic molecule, for example.

The present disclosure, in some embodiments, provides biosensing gloves having fingertips that comprise a hydrogel-elastomer composition encapsulating a population of genetically-engineered cells that comprise a promoter operably linked to a nucleic acid encoding a product of interest.

In some embodiments, the elastomer is comprised of silicone. For example, the silicone may be polydimethylsiloxane (PDMS) or a platinum-catalyzed silicone (e.g., ECO-FLEX® silicone). In some embodiments, the elastomer is microporous.

In some embodiments, the population of genetically-engineered cells is a heterogeneous population. In some embodiments, the heterogeneous population comprises subsets of cells, each subset comprising a different promoter relative to the other subsets of the population. For example, one subset of genetically-engineered cells of the population may comprise a first inducible promoter operably linked to a nucleic acid encoding a first product of interest, and another subset of genetically-engineered cells of the population may comprise a second inducible promoter operably linked to a nucleic acid encoding a second product of interest, wherein activity of the second inducible promoter is modulated by the first product of interest.

In some embodiments, the genetically-engineered cells are genetically-engineered bacterial cells. Other cell types may be used.

Biosensing gloves, and other wearable devices of the present disclosure, may include a hydrogel-elastomer comprising a population of cells genetically-engineered to respond to signals from an environment (e.g., for monitoring the environment, such as a water contamination site or a healthcare facility). For example, activity of an inducible promoter of a genetic circuit within an engineered cell may be modulated by a cognate inducer present in the water, soil or other environmental area.

Methods

The present disclosure also provides methods of contacting a composition and/or wearable device (e.g., skin patch and/or biosensing glove) with a cognate inducer that modulates activity the inducible promoter of the genetically-engineered cells.

Also provided herein are methods comprising (a) contacting a hydrogel-elastomer composition with a solution containing cell nutrients to produce a nutrient-infused hydrogel-elastomer composition, and (b) introducing a population of genetically-engineered cells into the nutrient-infused hydrogel-elastomer composition to produce genetically-engineered cells encapsulated by the nutrient-infused hydrogel, wherein the genetically-engineered cells comprise a promoter operably linked to a nucleic acid encoding a product of interest.

In some embodiments, the hydrogel of the hydrogel-elastomer composition is comprised of polyacrylamide (PAAm)-alginate. In some embodiments, the PAAm is covalently crosslinked PAAm and the alginate is ionically crosslinked alginate. In some embodiments, the hydrogel is infused with cell nutrients.

In some embodiments, the elastomer is air-permeable. In some embodiments, the elastomer is comprised of silicone. For example, the silicone may be/may comprise polydimethylsiloxane (PDMS) and/or platinum-catalyzed silicone (e.g., ECOFLEX silicone). In some embodiments, the elastomer is microporous.

Further provided herein are methods comprising (a) combining a culture of genetically-engineered cells with alginate to produce droplets, (b) crosslinking the droplets with calcium ions to form spheres containing the genetically-engineered cells, and (c) encapsulating the spheres with a hydrogel to form a capsule, wherein the genetically-engineered cells comprise a promoter operably linked to a nucleic acid encoding a product of interest.

In some embodiments, the hydrogel of the hydrogel-alginate composition/capsule is comprised of polyacrylamide (PAAm) and alginate. In some embodiments, the PAAm is covalently crosslinked PAAm and the alginate is ionically crosslinked alginate.

In some embodiments, the capsule comprises pores having a pore size of 50 nm or less. For example, the pore size may be 5-50 nm.

In some embodiments, the population of genetically-engineered cells is a heterogeneous population. In some embodiments, the heterogeneous population comprises subsets of cells, each subset comprising a different promoter relative to the other subsets of the population.

In some embodiments, the promoter is an inducible promoter.

In some embodiments, one subset of genetically-engineered cells of the population comprises a first inducible promoter operably linked to a nucleic acid encoding a first product of interest, and another subset of genetically-engineered cells of the population comprises a second inducible promoter operably linked to a nucleic acid encoding a second product of interest, wherein activity of the second inducible promoter is modulated by the first product of interest.

In some embodiments, the genetically-engineered cells are genetically-engineered bacterial cells.

In some embodiments, activity of the inducible promoter is modulated by a quorum-sensing molecule. In some embodiments, the product of interest is a quorum-sensing molecule.

ADDITIONAL EMBODIMENTS

1. A composition comprising genetically engineered bacteria comprising an analog or digital reporter system for logging long-term memory of conditions of the bacterial environment, and a tough and stretchable hydrogel that encapsulates the bacteria, wherein the hydrogel protects the bacteria from the adverse effects of the environment and provides biocontainment of the bacteria.
2. A composition comprising a genetically engineered heavy metal ion sensing bacterial strain, and a tough and stretchable hydrogel that encapsulates the bacteria, wherein the hydrogel protects the bacteria from the adverse effects of the environment and provides biocontainment of the bacteria.
3. The composition of embodiment 1 or 2, wherein the hydrogel is made of (a) polyethylene glycol (PEG) or polyacrylamide and (b) alginate.
4. The composition of any one of embodiments 1-3, wherein the hydrogel is coated.
5. A method of encapsulating living cells in tough hydrogel beads, comprising (a) combining engineered bacterial cells that comprise an analog or digital reporter system for logging long-term memory of conditions of the bacterial environment with alginate; (b) solidifying the alginate in calcium to form alginate beads; (c) diffusing polyacrylamide into the alginate of (b); and (d) crosslinking the alginate and polyacrylamide of (c).
6. A method of encapsulating living cells in tough hydrogel beads, comprising (a) combining a genetically engineered heavy metal ion sensing bacterial strain with alginate; (b) solidifying the alginate in calcium to form alginate beads; (c) diffusing polyacrylamide into the alginate of (b); and (d) crosslinking the alginate and polyacrylamide of (c).
7. A composition comprising a robust and biocompatible hydrogel, and an elastomer, wherein the hydrogel and the elastomer are bonded into a hybrid structure.
8. The composition of embodiment 7, further comprising patterned cavities on a hydrogel-elastomer interface.
9. The composition of embodiment embodiment 7 or 8, wherein the hydrogel is polyacrylamide-alginate (PAAm-alginate) hydrogel or a fiber-reinforced tough hydrogel.
10. The composition of any one of embodiments 7-9, wherein the elastomer is air permeable.
11. The composition of any one of embodiments 7-10, wherein the elastomer is polydimethylsiloxane (PDMS), ECOFLEX® (Smooth-On) silicone elastomer, SILBIONE® or a microporous elastomer.

12. The composition of any one of embodiments 7-11, wherein the bonding between the hydrogel and elastomer comprises covalently anchoring the hydrogel on the elastomer substrate.
13. The composition of any one of embodiments 7-12, wherein the hydrogel comprises growth media for cells to be seeded in the hydrogel.
14. The composition of any one of embodiments 7-13, wherein the high stretchability and robustness of the hydrogel-elastomer hybrids prevents leakage of cells from the materials and devices made from the composition.
15. The composition of any one of embodiments 7-14, wherein the composition is a skin patch or glove.
16. The composition of any one of embodiments 7-15, wherein the hydrogel comprises cells.
17. The composition of embodiment 16, wherein the cells are bacterial cells.
18. The composition of embodiment 16 or 17, wherein the cells comprise one or more genetic circuits.
19. The composition of any one of embodiments 16-18, wherein the cells sense one or more molecules and produce an output signal when exposed to the one or more molecules.

Also provided herein are compositions that include a robust and biocompatible hydrogel, and an elastomer, wherein the hydrogel and the elastomer are bonded into a hybrid structure. In some embodiments, the compositions include patterned cavities on a hydrogel-elastomer interface. In some embodiments, the hydrogel is polyacrylamide-alginate (PAAm-alginate) hydrogel or a fiber-reinforced tough hydrogel. In some embodiments, the elastomer is air permeable. In some embodiments, the elastomer is polydimethylsiloxane (PDMS), ECOFLEX® (Smooth-On) silicone elastomer, SILBIONE® or a microporous elastomer. In some embodiments, the bonding between the hydrogel and elastomer comprises covalently anchoring the hydrogel on the elastomer substrate.

In some embodiments, the hydrogel comprises growth media for cells to be seeded in the hydrogel. In some embodiments, the high stretchability and robustness of the hydrogel-elastomer hybrids prevents leakage of cells from the materials and devices made from the composition. In some embodiments, the composition is a skin patch or glove.

In some embodiments, the hydrogel comprises cells. In some embodiments, the cells are bacterial cells. In some embodiments, the cells comprise at least one (one or more) genetic circuit(s). In some embodiments, the cells sense at least one (one or more) molecule(s) and produce an output signal when exposed to the at least one (one or more) molecule(s).

EXAMPLES

Example 1: Hydrogel Encapsulation of Cells

Hydrogel devices were designed to encapsulate living cells in their cores, surrounded by a tough hydrogel shell.

Figure 1B:
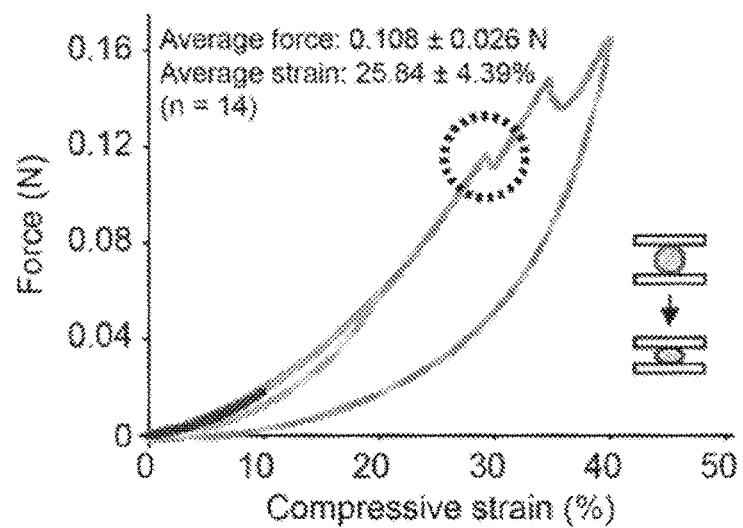
Figure 1C:
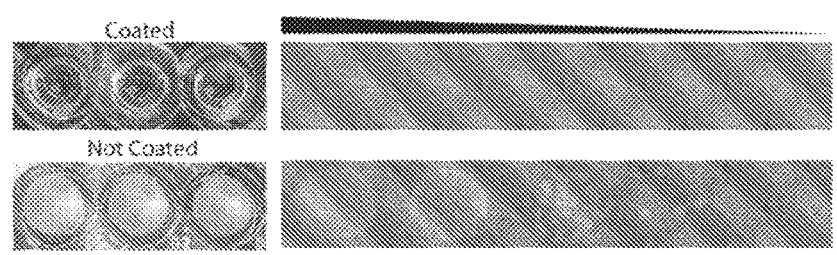
Figure 1C:
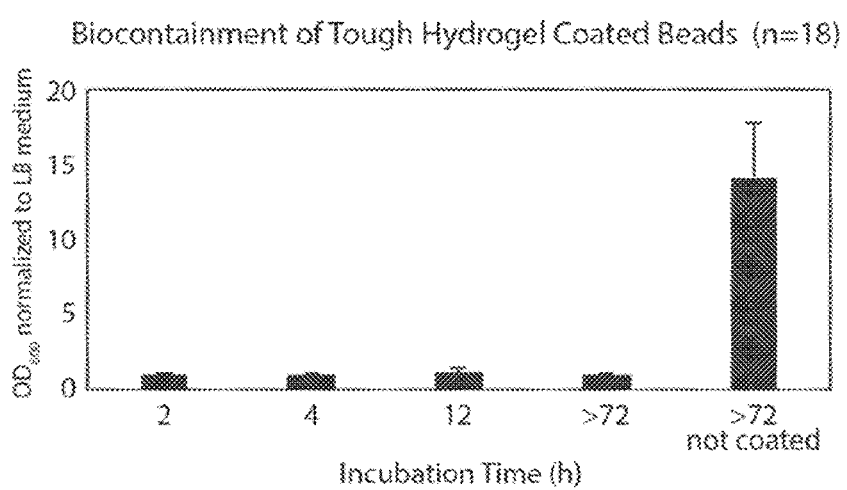
Figure 1D:
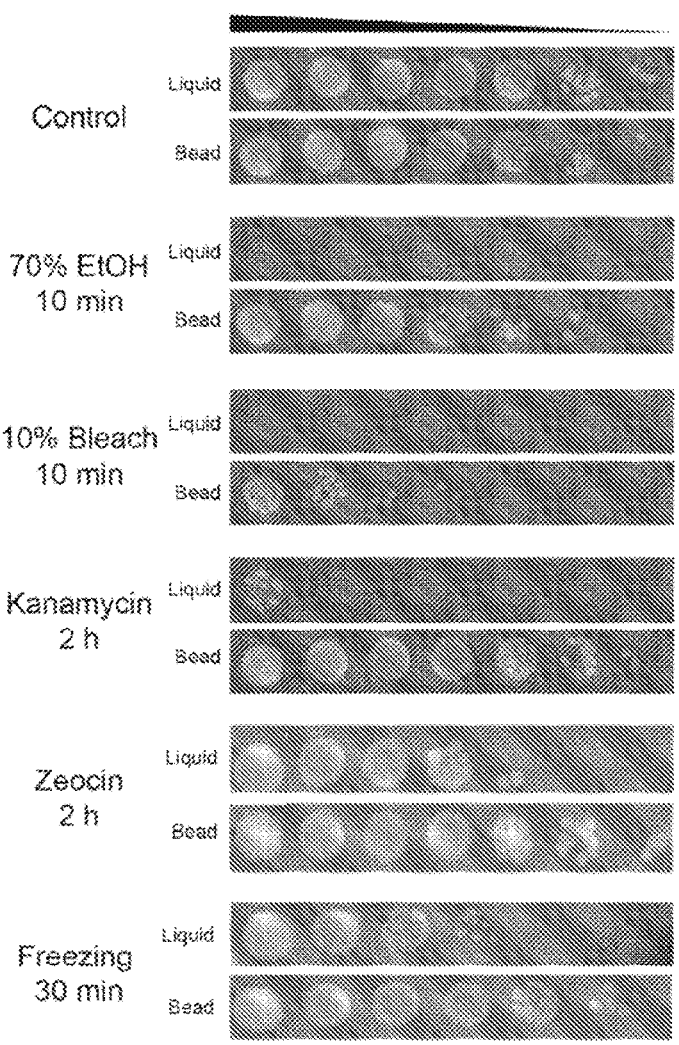

Cells were encapsulated into tough hydrogels to achieve biocontainment (FIG. 1C). Hydrogels provide protection for cells from harsh environments (FIG. 1D). Additionally, hydrogel-cell beads sense environmental signals (FIG. 1D).

Thus, the present disclosure also provides: methods of using genomically recoded organisms (GRO) to provide chemical containment; methods of using the metal ion sensing hydrogel-cell system with environmental samples (e.g., river water, soil, etc.); and methods of using a coaxial nozzle system to produce hydrogel beads.

Example 2: Design of Living Materials and Devices

Figure 6A:
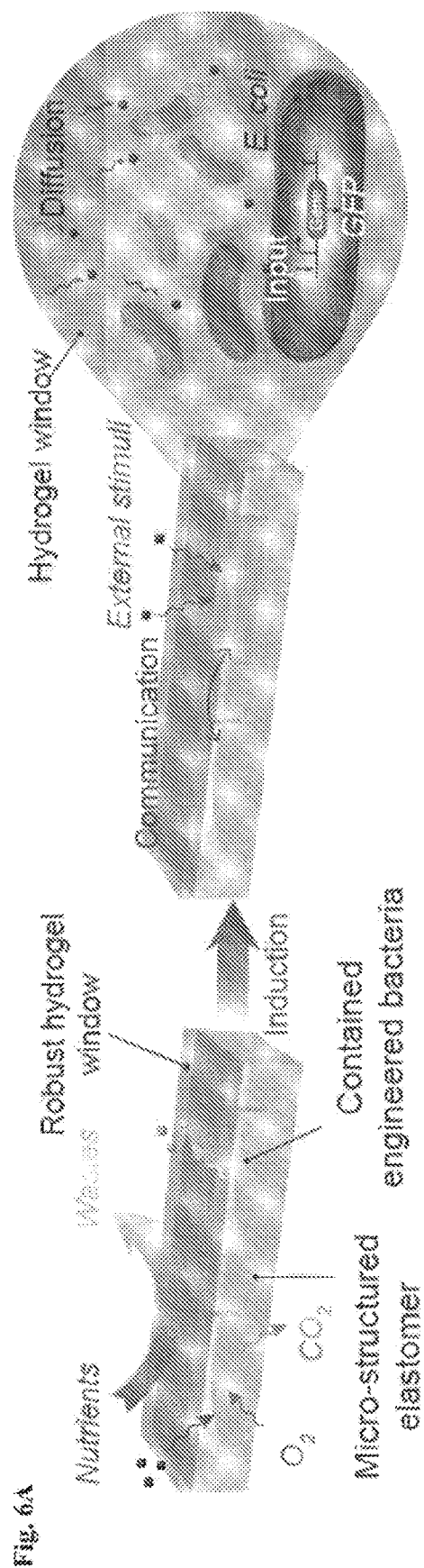
FIGS. 6A-6D show design of living materials and devices.
Figure 11A:
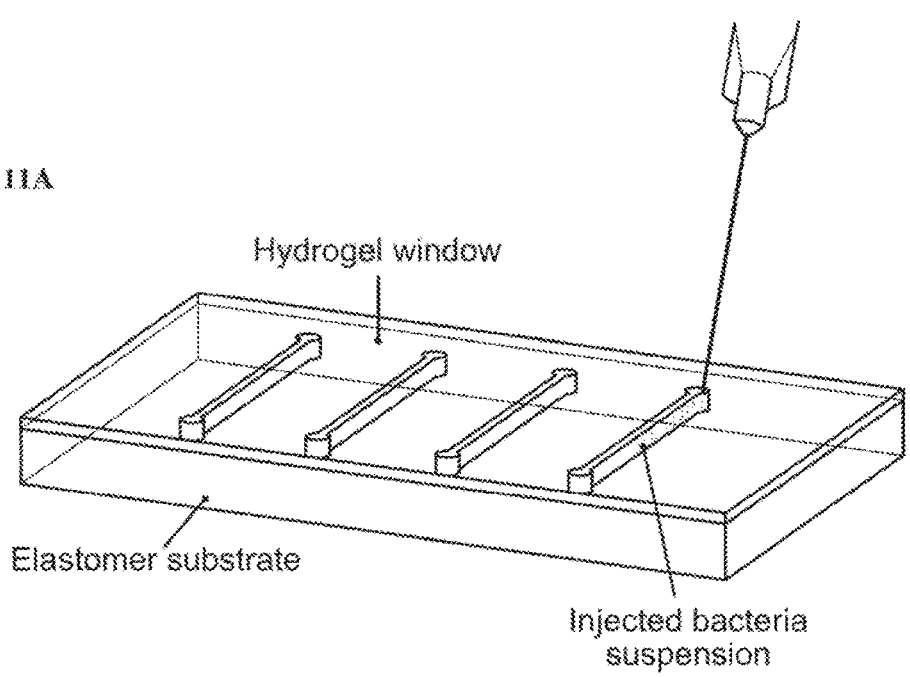
FIGS. 11A-11C show a schematic illustration of cell suspension injection, and sealing of injection points.
Figure 11B:
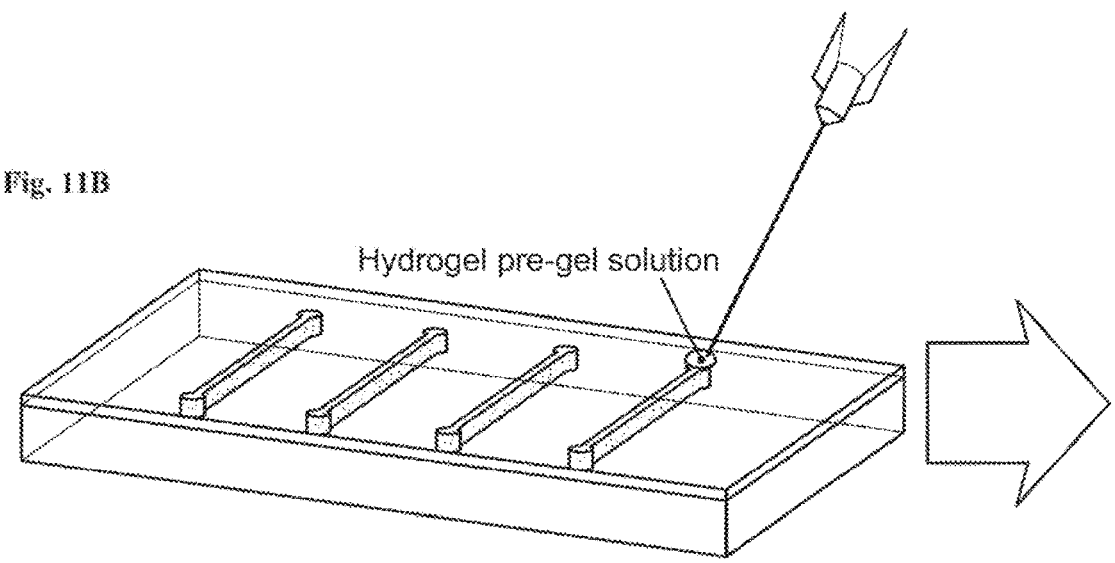
Figure 11C:
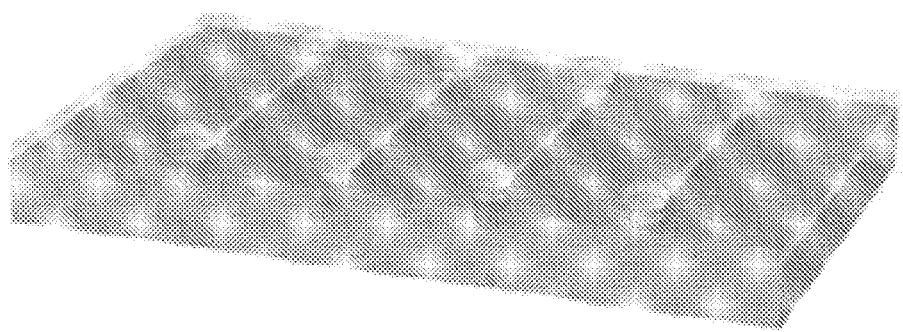
Figures 12A, 12B, 12C, 12D:
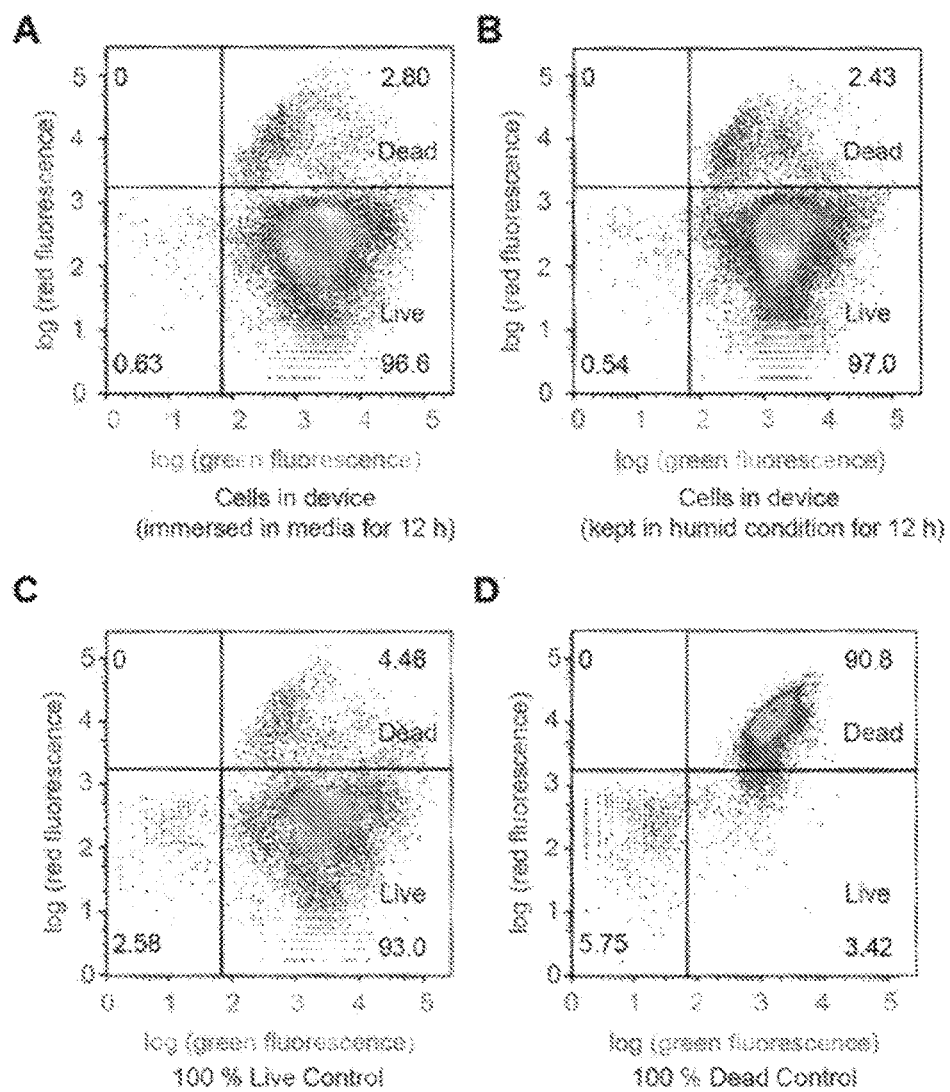
FIGS. 12A-12D show flow cytometry analysis using live/dead stains for (FIG. 12A) cells retrieved from the living device that has been immersed in media for 12 h, (FIG. 12B) cells retrieved from the living device that has been placed in humid environment for 12 h, (FIG. 12C) live-cell controls, and (FIG. 12D) dead-cell controls. Green fluorescence denotes both live and dead bacteria, and the red fluorescence denotes bacteria that have been damaged and leaky membranes. The distributions of the live and dead populations are illustrated in the plots, with thresholds determined by controls. Over 95% of cells in the hydrogel-elastomer devices immersed in media or placed in humid chamber remained viable after 12 h, respectively.

Encapsulating genetically engineered cells in biocompatible, stretchable and robust hydrogel-elastomer hybrid matrices represents a general strategy for the design of living materials and devices with powerful properties and functions. The design of a generic structure for the living materials and devices is illustrated in FIG. 6A. In brief, layers of robust and biocompatible hydrogel and elastomer were assembled and bonded into a hybrid structure (15). Patterned cavities of different shapes and sizes were introduced on the hydrogel-elastomer interfaces to host living cells in subsequent steps. The hydrogel-elastomer hybrid was then immersed in culture media for 12 h, so that the hydrogel can be infiltrated with nutrients. Thereafter, genetically engineered bacteria suspended in media were infused into the patterned cavities through the hydrogel, and the injection points were then sealed with drops of fast-curable pre-gel solution (FIG. 11). Since the hydrogel was infiltrated with media and the elastomer is air permeable, hydrogel-elastomer hybrids with proper dimensions can provide sustained supplies of water, nutrient and oxygen (if needed) to the cells. By tuning the dimensions of hydrogel walls between different types of cells and between cells and external environments, the transportation times of signaling molecules for cell communication can be controlled. Furthermore, the high mechanical robustness of the hydrogel, elastomer and their interface confer structural integrity to the matrix even under large deformations, thus preventing cell escape in dynamic environments.

Polyacrylamide-alginate (PAAm-alginate) hydrogel (15, 17), and polydimethylsiloxane (PDMS, SYLGARD® 184, Dow Corning) or ECOFLEX® (Smooth-On) silicone elastomer were chose to constitute the robust hydrogel and elastomer, respectively. The biocompatibility of these materials has been extensively validated in various biomedical applications (20, 21). The sufficient gas permeation of the silicone elastomer enables oxygen supply for the bacteria (22-24). If higher level of oxygen is required, one may choose elastomers with higher permeability such as SILBIONE® (25) or microporous elastomers (23). In the hydrogel, covalently-crosslinked PAAm network is highly stretchable and the reversibly-crosslinked alginate network dissipates mechanical energy under deformation, leading to tough and stretchable hydrogels (14, 17, 26). More robust devices can be fabricated by using fiber reinforced tough hydrogel (27). Robust bonding between the hydrogel and elastomer can be achieved by covalently anchoring the PAAm network on the elastomer substrate (15, 18, 26).

The *Escherichia coli* (*E. coli*) bacterial strains were engineered to produce outputs (e.g., expressing green fluorescent protein (GFP)) under control of promoters that are inducible by cognate chemicals. For example, the $DAPG_{RCV}$/GFP strain produces GFP when the chemical inducer DAPG is added and received by the cells. The cell strains used herein included $DAPG_{RCV}$/GFP, $AHL_{RCV}$/GFP, $IPTG_{RCV}$/GFP, $Rham_{RCV}$/GFP, and $aTc_{RCV}$/AHL. The 2,4-diacetylphloroglucinol (DAPG), N-acyl homoserine lactone (AHL), isopropyl β-D-1-thiogalactopyranoside (IPTG), rhamnose (Rham), and anhydrotetracycline (aTc) are small molecules with biochemical activities, and used as the signaling molecules.

To evaluate the viability of cells in living materials and devices, the hydrogel-elastomer matrices containing $Rham_{RCV}$/GFP cells (FIG. 6A) were placed in a humid chamber (relative humidity >90%) without addition of growth media, or immersed the living materials in the growth media at room temperature (25° C.) for 3 days. The cells were also directly cultured in growth media as a control. Thereafter, the live/dead stain was used and flow cytometry analysis was performed for bacteria retrieved from the living device to test the cell viability. As shown in FIG. 6C, the viability of cells in the device placed in humid chamber maintains above 90% over 3 days without addition of media to the device. This viability is similar to that of cells in the device immersed in media or cells directly cultured in media at room temperature over 3 days.

Figure 6B:
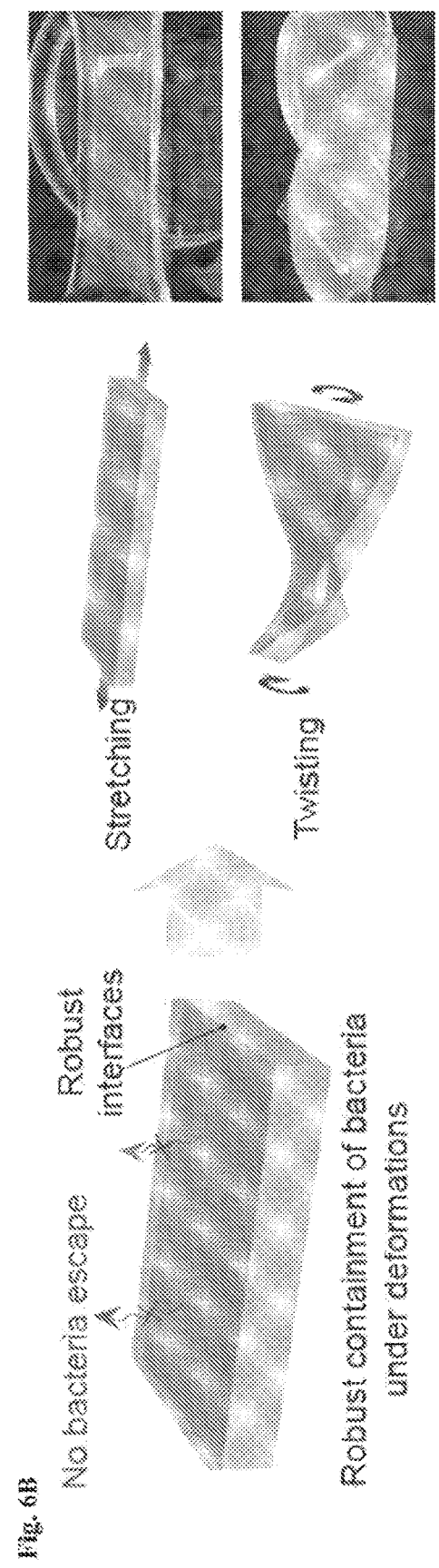
Figure 6D:
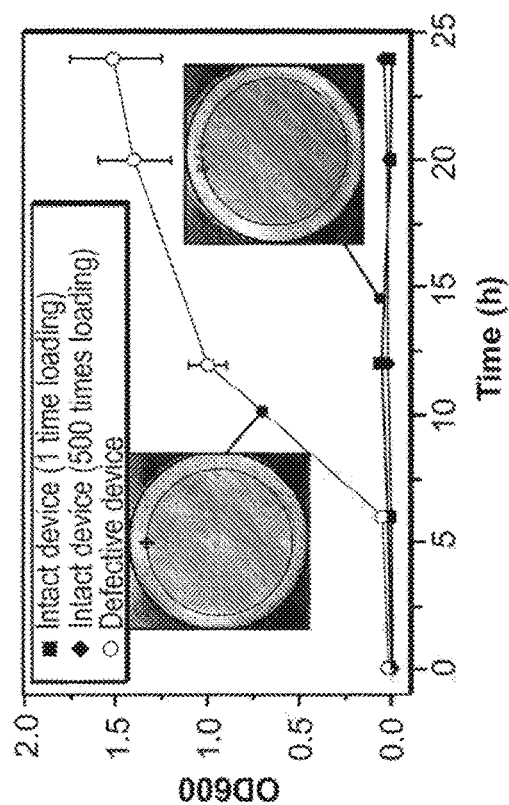
Figure 6C:
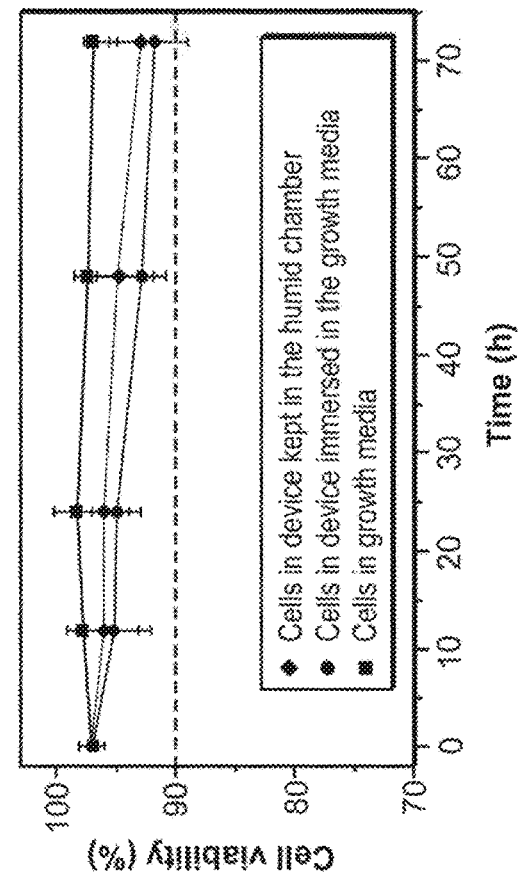
Figure 13:
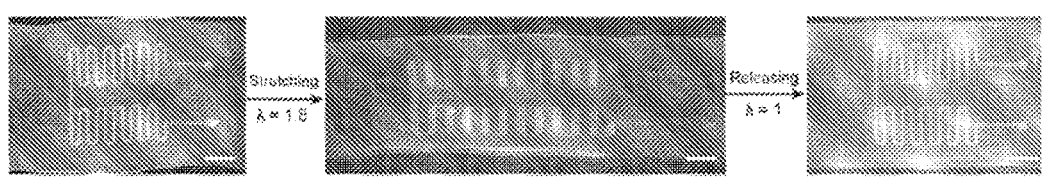
FIG. 13 shows functional living device under large uniaxial stretch. After GFP was switched on in the wavy channels of ECOFLEX®-hydrogel hybrid matrix, the device was stretched to 1.8 times of its original length, and then released. The device including cells encapsulated can maintain functionality under large deformation without failure or leakage. Scale bar: 5 mm.
Figures 14A, 14B, 14C, 14D, 14E, 14F:
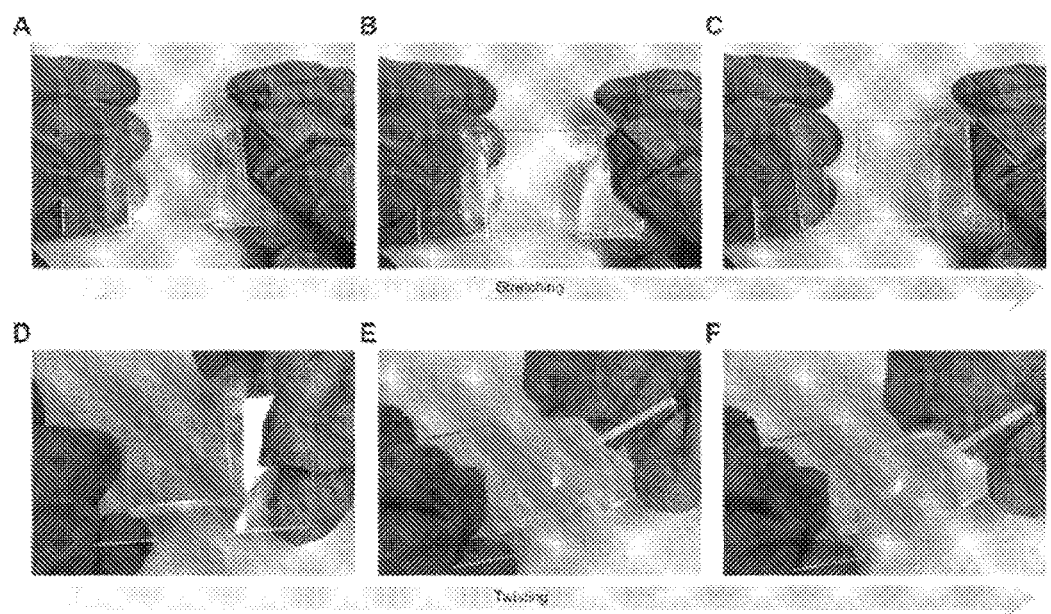
FIG. 14 shows deformation of agar-based living devices. An agar-based control device that encapsulated Rham$_{RCV}$/GFP bacteria with the same dimensions as the hydrogel-elastomer hybrid was fabricated. The agar device fractured even under a moderate deformation, including (A-C) a stretch of 1.1 or (D-F) a twist of 60°.
Figure 15:
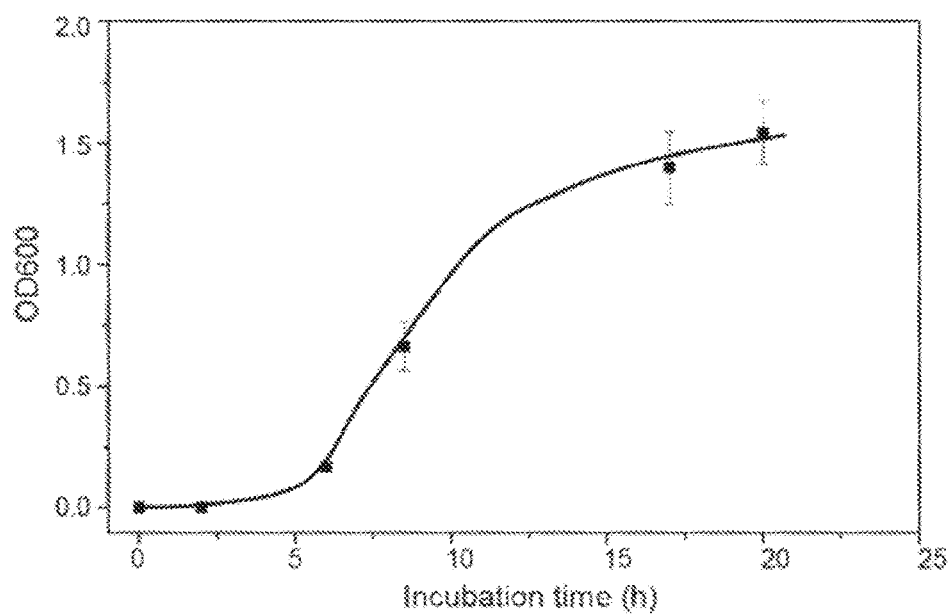
FIG. 15 shows cell leakage from the agar device. The medium surrounding the agar device (without any deformation) was collected to measure OD$_{600}$. The high OD$_{600}$ after 10 h indicates the large cell populations in the medium and cell leakage even without any deformation of agar gel.
Figures 16A, 16B, 16C, 16D, 16E:
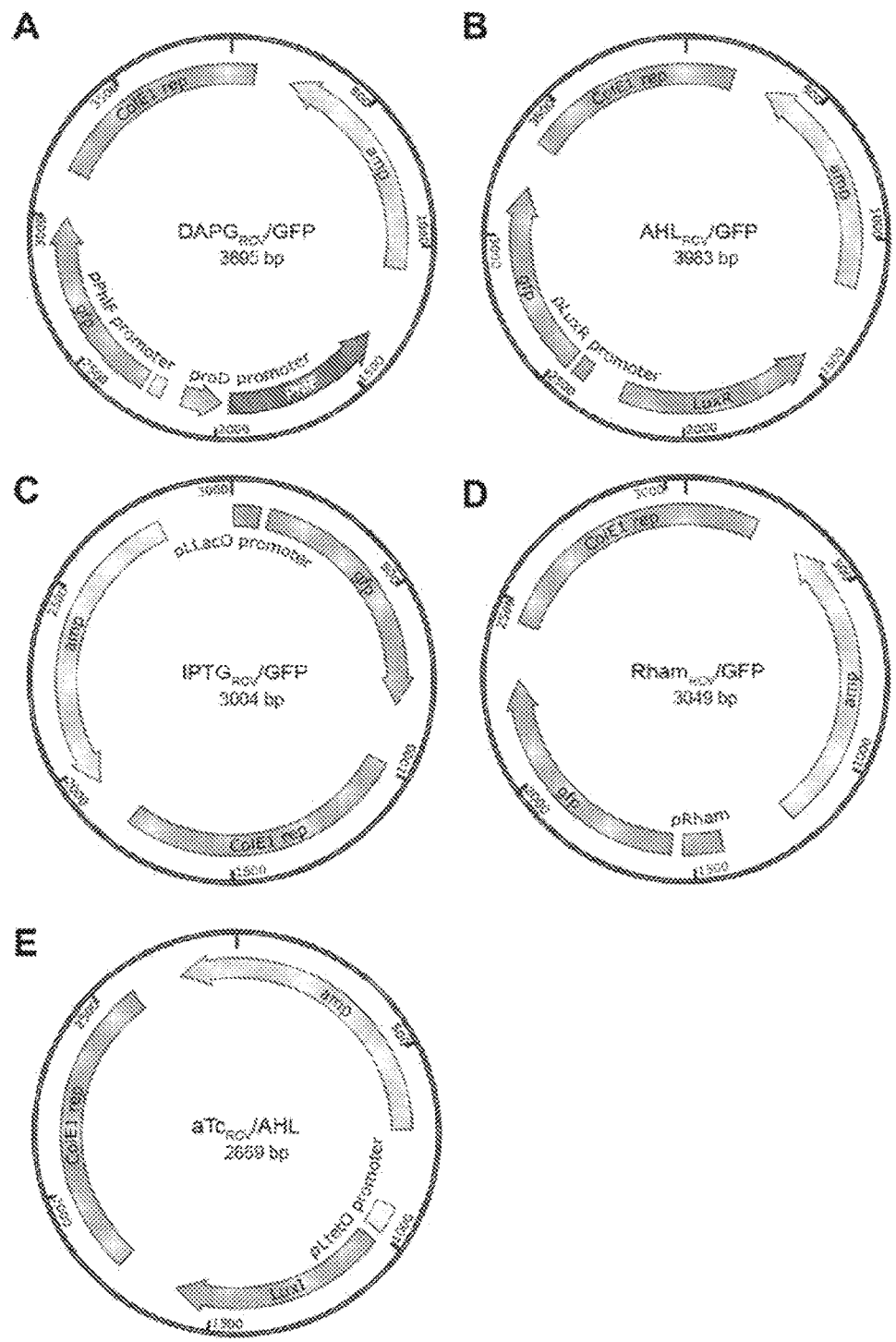
FIGS. 16A-16E shows plasmid maps of the plasmids constructed.

To test whether bacteria could escape from the living devices, the hydrogel-elastomer hybrids illustrated in FIG. 6B containing $Rham_{RCV}$/GFP bacteria were deformed in different modes (i.e., stretching and twisting), and then immersed the device in media for a 24 h period. As shown in FIG. 6B and FIG. 13, the living device made of Ecoflex and tough hydrogel sustained a uniaxial stretch over 1.8 times of its original length and a twist over 180° while maintaining its structural integrity. Furthermore, after immersing the device in media for 6, 12, 20, and 24 h, the media surrounding the device were collected and the cell population in the media was measured over time via $OD_{600}$ by UV spectroscopy (FIG. 6D). 200 μL of media were streaked on agar plates after 24 h to check for cell escape and growth (FIG. 6D, inset optical images). FIG. 6D demonstrates that bacteria did not escape the hydrogel-elastomer hybrid even under repeated mechanical loads (500 cycles). As controls, defective devices (with weak hydrogel-elastomer bonding) were intentionally created and significant escape and overgrowth of bacteria was observed after immersing the samples in media (yellow curve, FIG. 6D). Since agar hydrogels have been widely used for cell encapsulation, an agar-based control device was fabricated that encapsulated $Rham_{RCV}$/GFP bacteria with the same dimensions as the hydrogel-elastomer hybrid. In FIG. 14, it can be seen that these agar devices underwent failures even under moderate deformation (e.g., a stretch of 1.1 or a twist of 60°). Moreover, cell leakage from the agar devices occurred regardless of the presence of any deformation, likely due to the large pore sizes and sol-gel transition of the agar gel allowing for escape of encapsulated bacteria. These results indicate that the disclosed hydrogel-elastomer hybrids can provide a biocompatible, stretchable and robust host for genetically engineered bacteria.

Example 3: Stretchable Living Sensors for Chemical Sensing

Figure 7A:
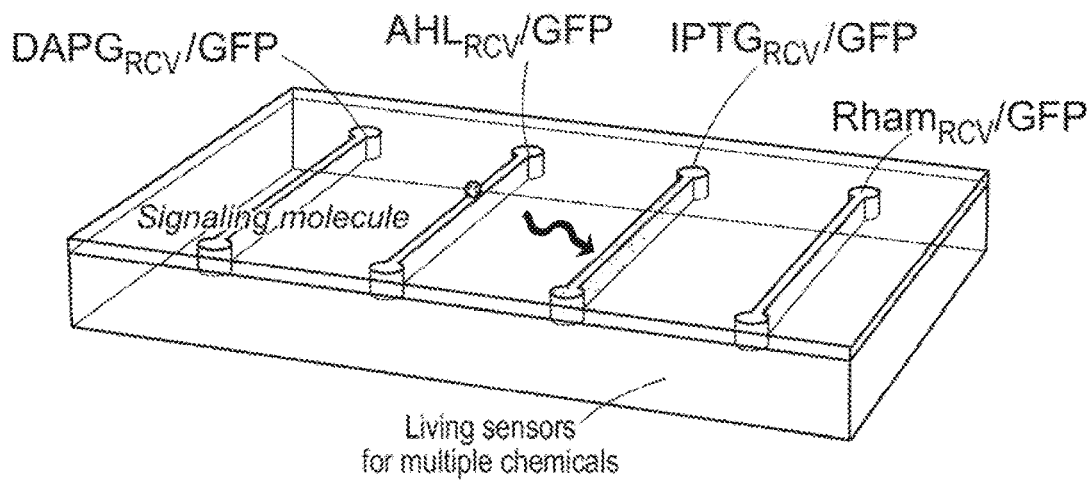
FIGS. 7A-7C show stretchable living sensors can independently detect multiple chemicals.
Figure 7B:
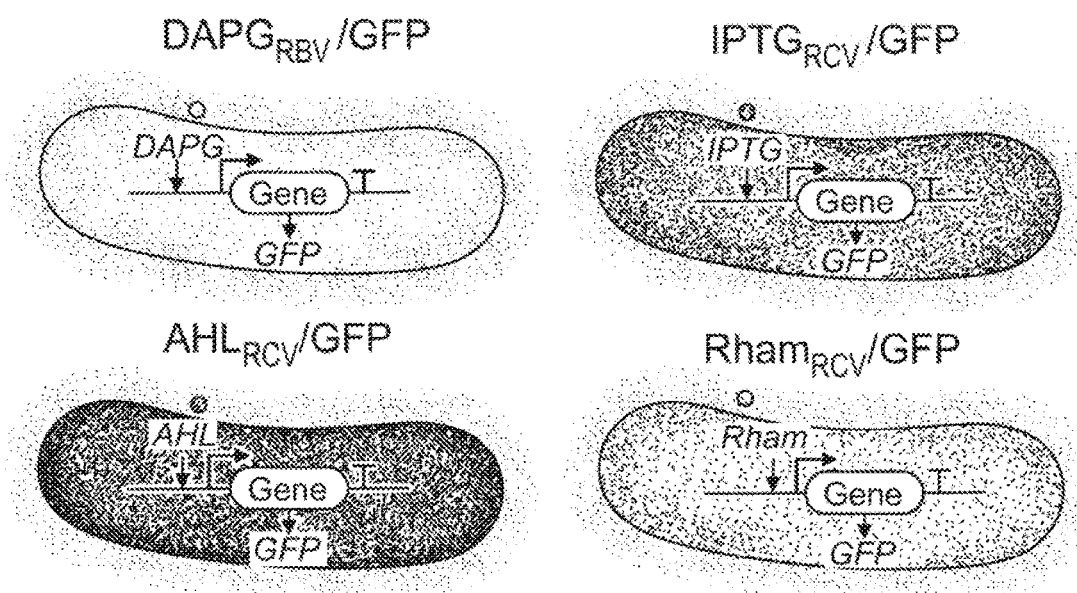
Figure 7C:
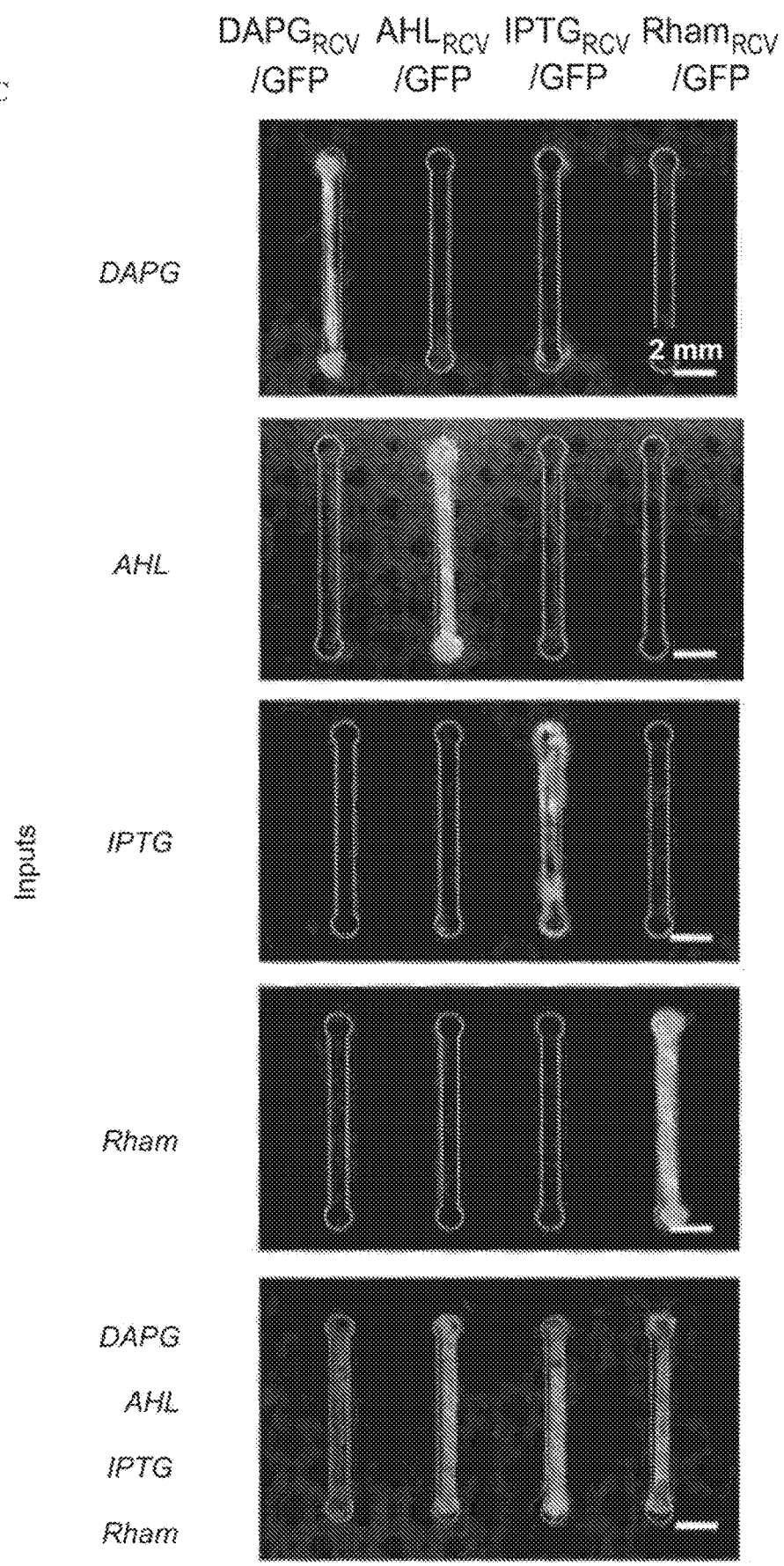
Figure 17:
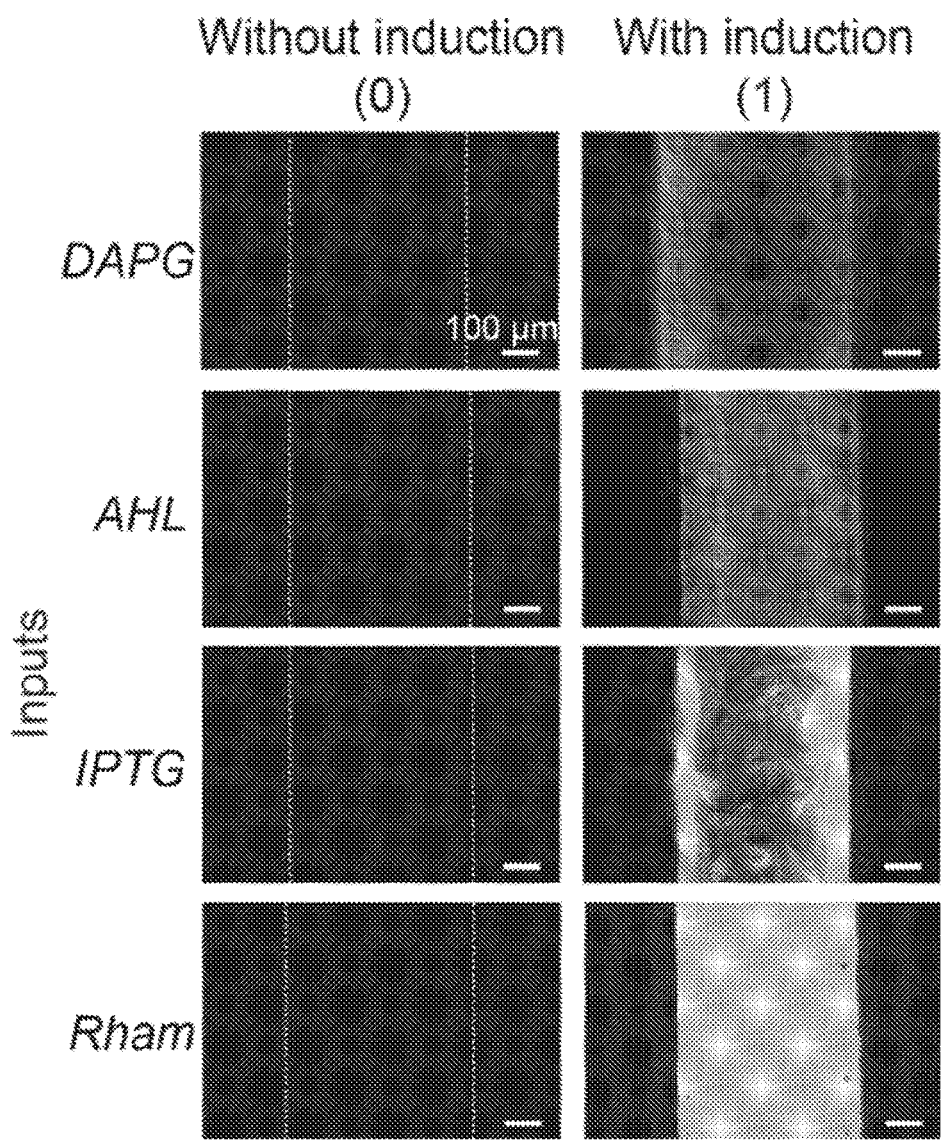
FIG. 17 shows microscopic images of different cell strains in the chamber encapsulated in the living device. When a cell strain was induced, the channels showed fluorescence (denoted as "1"). If not induced, the channel stay dark (denoted as "0"). Scale bars are shown in images.

Novel functions and applications enabled by the living materials and devices were next demonstrated. FIG. 7A illustrates a hydrogel-elastomer hybrid with four isolated chambers that each hosted a different bacterial strain, $DAPG_{RCV}$/GFP, $AHL_{RCV}$/GFP, $IPTG_{RCV}$/GFP, and $Rham_{RCV}$/GFP. The genetic circuits in these bacterial strains can sense their cognate inducers and express GFP, which can be visible under blue light illumination. As mentioned above, the $DAPG_{RCV}$/GFP strain exhibits green fluorescence when receiving DAPG, but is not responsive to other stimuli. Similarly, the $AHL_{RCV}$/GFP strain expresses GFP only induced by AHL; IPTG selectively induces GFP expression in the $IPTG_{RCV}$/GFP strain; and Rham selectively induces the green fluorescence output of the $Rham_{RCV}$/GFP strain (FIG. 7B). It was shown that each inducer, diffusing from the environment through the hydrogel into cell chamber, can trigger GFP expression of its cognate strain inside the device, which could be visualized by the naked eye or microscope (FIG. 7C and FIG. 17). This orthogonality makes the hydrogel-elastomer hybrid with encapsulated bacteria into a living sensor that can simultaneously detect multiple chemicals in the environment (FIG. 7C). About two hours are required for each strain to produce significant fluorescence. Parameters that affect response times for the living sensor are discussed with a quantitative model below.

Example 4: Interactive Genetic Circuits

Figure 8B:
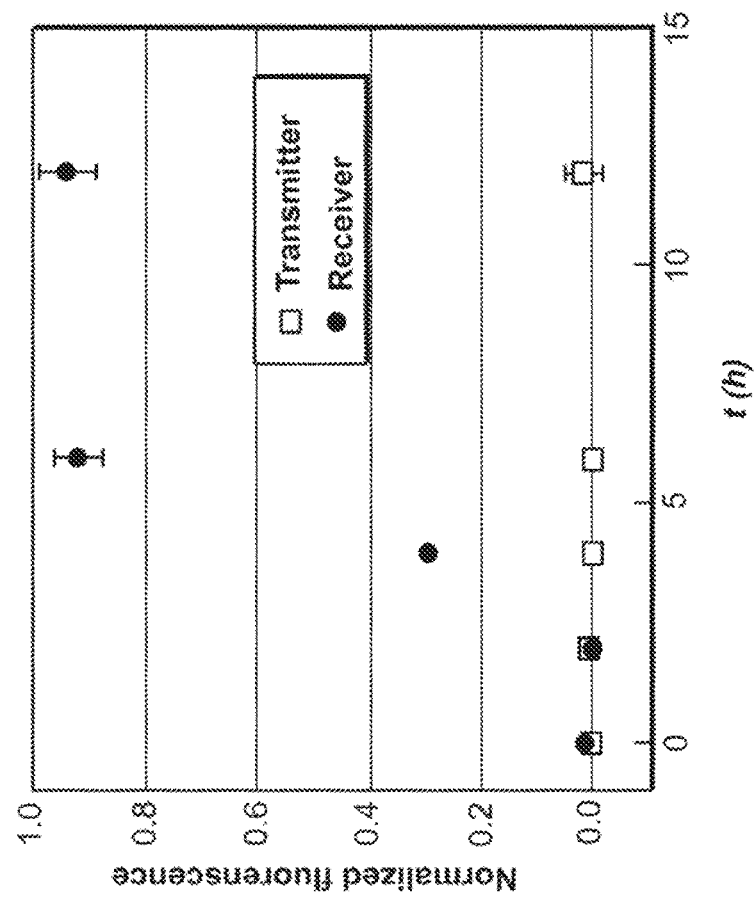
FIGS. 8A-8D show interactive genetic circuits.
Figure 8A:
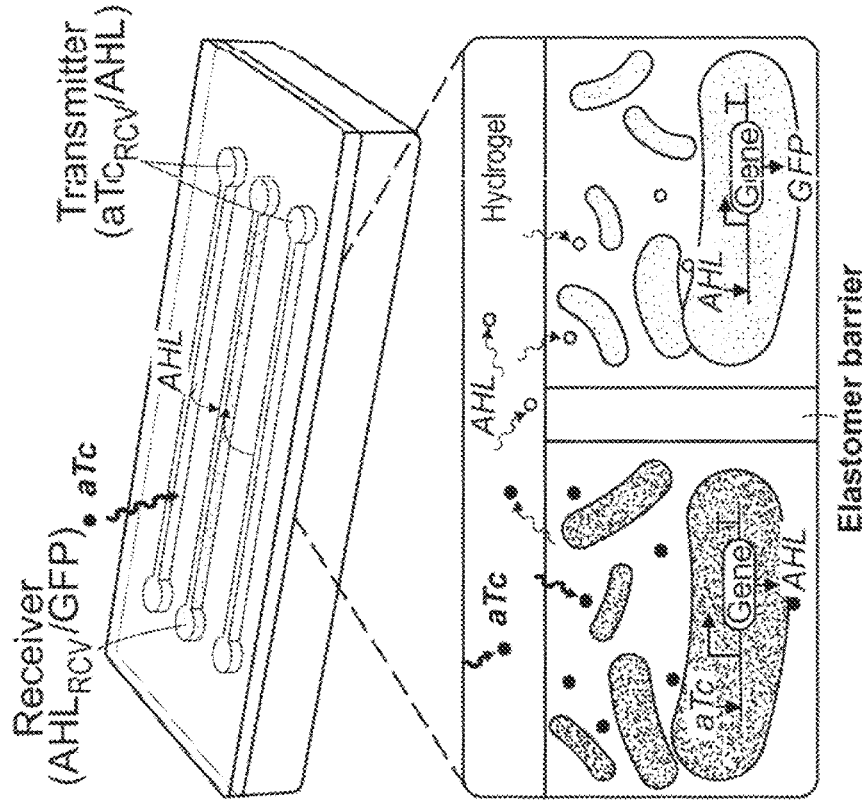
Figure 8D:
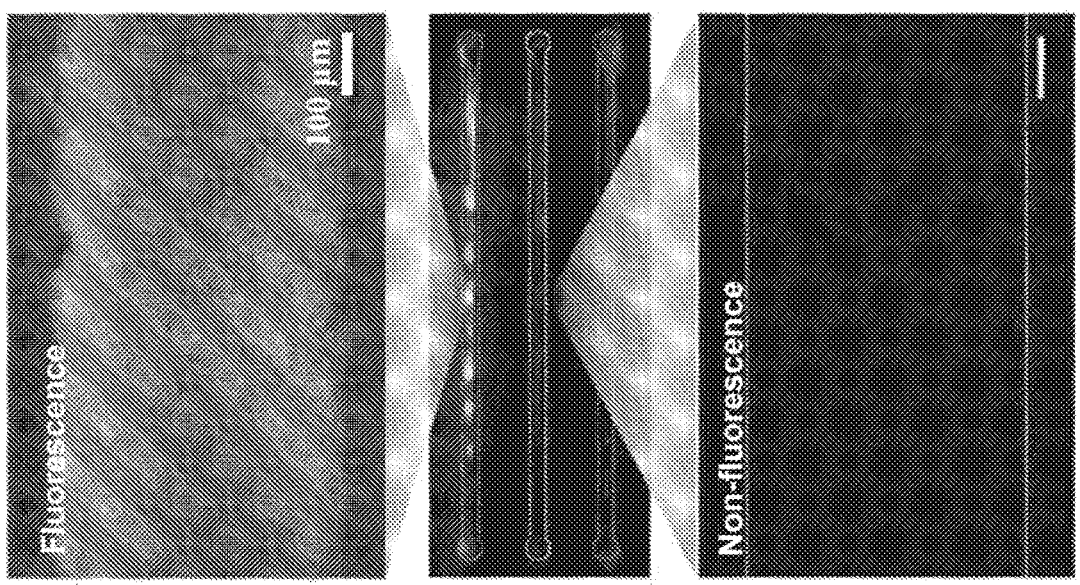
Figure 8C:
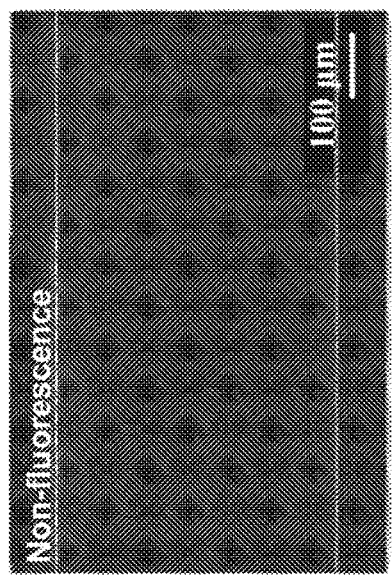
Figure 8C:
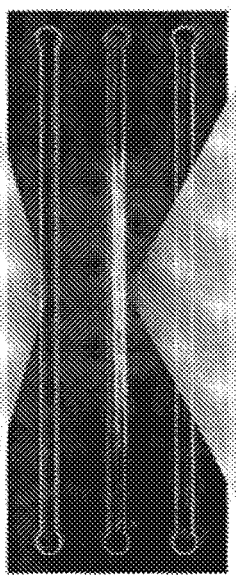
Figure 8C:
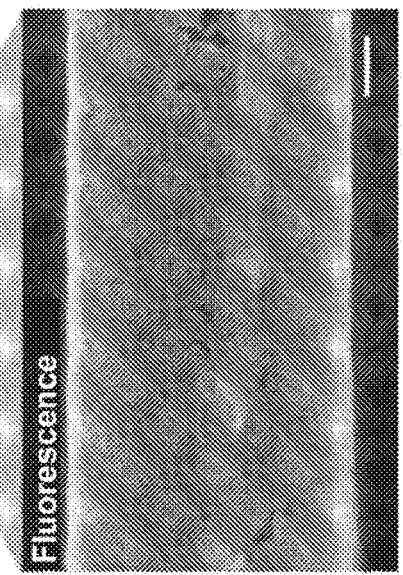

Next, cells containing different genetic circuits were integrated into a freestanding living device to study cellular signaling cascades. Two bacterial strains were designed that can communicate via the diffusion of signaling molecules through the hydrogel even though both were separated by an elastomer barrier within discrete chambers of the device (FIG. 8A). Specifically, a transmitter strain ($aTc_{RCV}$/AHL) was used that produces the quorum-sensing molecule AHL when induced by aTc, and a receiver strain ($AHL_{RCV}$/GFP) with an AHL-inducible GFP gene (5). This device was triggered with aTc from the environment to induce the transmitter cells, which resulted in AHL production and stimulation of receiver cells to synthesize GFP (FIG. 8C). In FIG. 8B, the normalized fluorescence of bacteria in different cell chambers (i.e., transmitter and receiver in FIG. 8A) is plotted as a function of time after aTc was added outside the device. Since there is no GFP gene in the transmitter cells ($aTc_{RCV}$/AHL), their chambers showed no fluorescence over time (FIG. 8B). It took longer response time (~5 h) for the receiver cells in the middle chamber to exhibit significant fluorescence, as compared with the cells in simple living sensors (FIG. 7A). Two diffusion processes (i.e., aTc from the environment to the two side chambers, and AHL from the two side chambers to the central chamber) and two induction processes (i.e., AHL production induced by aTc in transmitters, and GFP expression induced by AHL in receivers) were involved in the current interactive genetic circuits. As a control, when the transmitters ($aTc_{RCV}$/AHL) in the device was replaced by a cell strain containing aTc-inducible GFP ($aTc_{RCV}$/GFP) that cannot communicate with $AHL_{RCV}$/GFP, no fluorescence was observed in the receiver ($AHL_{RCV}$/GFP) chamber (FIG. 8D). Overall, the integrated devices containing interactive genetic circuits provide a new platform for the detection of various chemicals and the investigation of cellular interaction among physically isolated cell populations.

Example 5: Living Wearable Devices

Figure 19A:
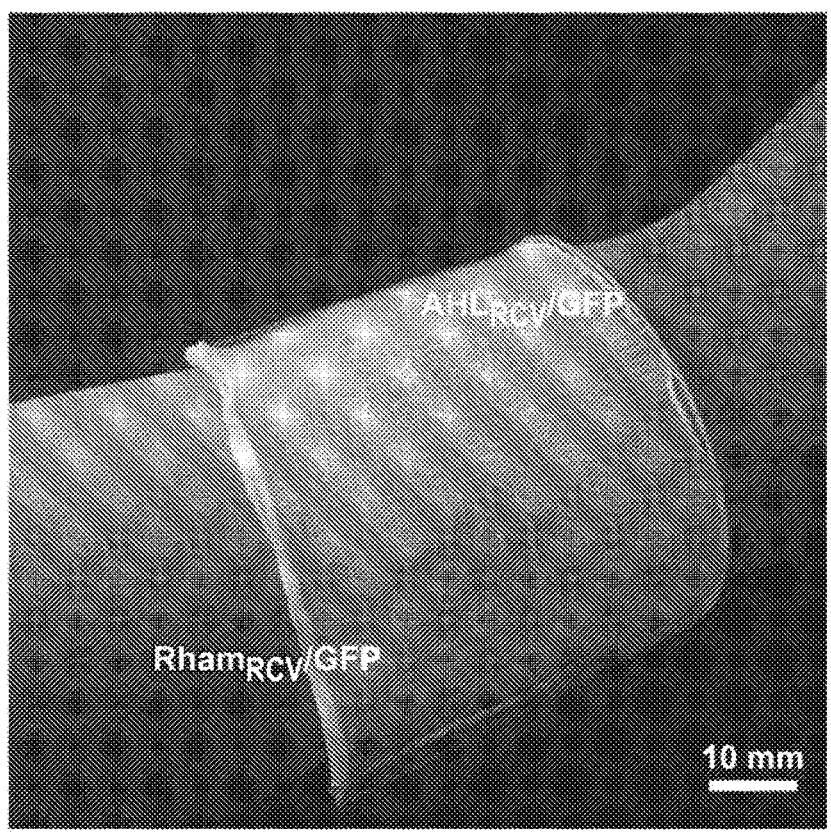
FIGS. 19A-19B show anti-dehydration property of the sensor patch.
Figure 19B:
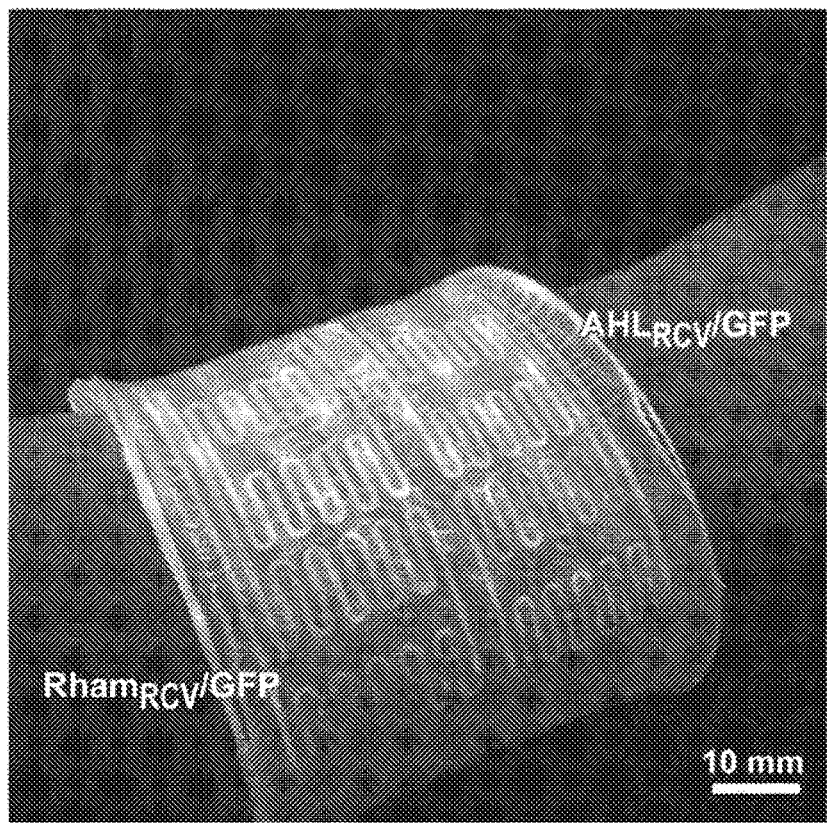

To further demonstrate practical applications of living materials and devices, a living wearable living patch was fabricated that detects chemicals on the skin (FIGS. 9A-9D). The sensing patch matrix consists of a bilayer hybrid structure of tough hydrogel and silicone elastomer. The wavy cell channels could cover a larger area of the skin with a limited amount of bacterial cells (FIG. 9A). The living patch can be fixed on the skin by clear Scotch tape, with the hydrogel exposed to the skin and the elastomer to the air. The compliance and stickiness of the hydrogel promotes conformal attachment of the living patch to human skin, while the silicone elastomer cover effectively prevents the dehydration of the sensor patch (FIG. 19) (15). As shown in FIG.

Figure 18A:
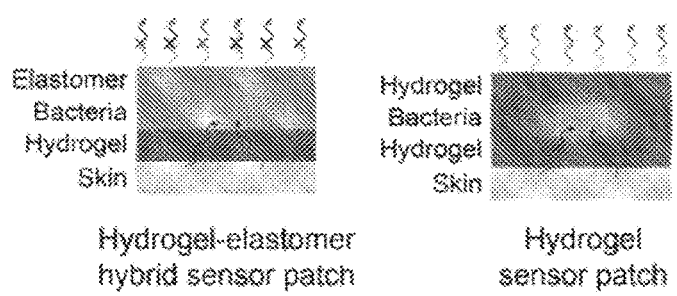
(FIG. 18A) DAPG$_{RCV}$/GFP, (FIG. 16B) AHL$_{RCV}$/GFP, (FIG. 16C) IPTG$_{RCV}$/GFP, (FIG. 16D) Rham$_{RCV}$/GFP, and (FIG. 16E) aTc$_{RCV}$/AHL. ColE1 rep: replication origin from ColE1 plasmid; gfp: green fluorescent protein; amp: ampicillin resistance gene.
Figure 18B:
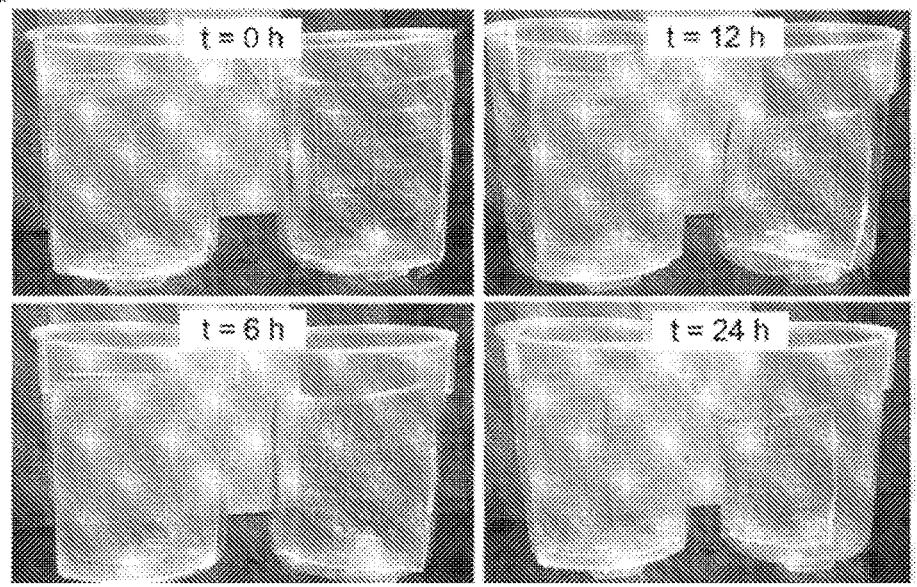

9B-9D, the inducer Rham was smeared on the skin of a forearm prior to adhering the living patch. The channels with Rham$_{RCV}$/GFP in the living patch became fluorescent within 4 h, while channels with AHL$_{RCV}$/GFP did not show any difference. As controls, no fluorescence was observed in any channels in absence of any inducer on the skin (FIG. 18A), while all channels became fluorescent in presence of both AHL and Rham (FIG. 18B). While the inducers are used as mock biomarkers here, more realistic chemical detections, such as components in human sweat or blood, may be pursued with living devices for scientific research and translational medicine in future.

Figure 9G:
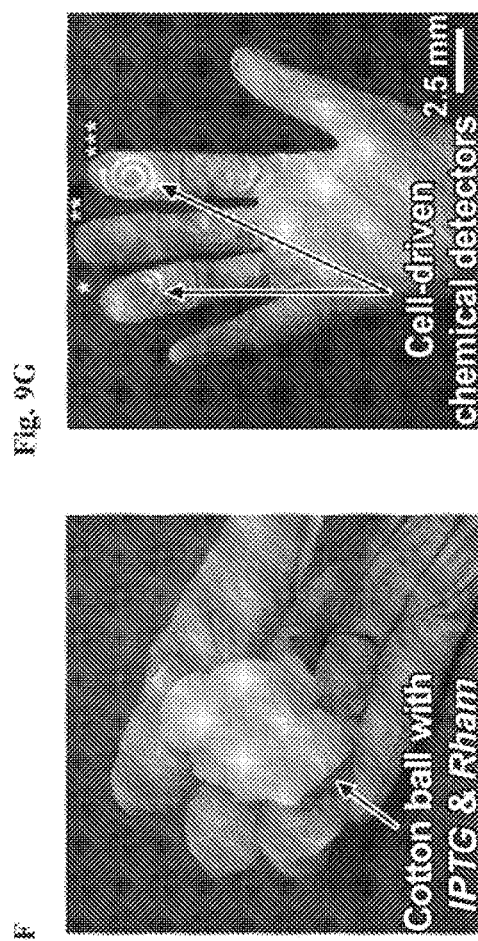
Figure 9F:
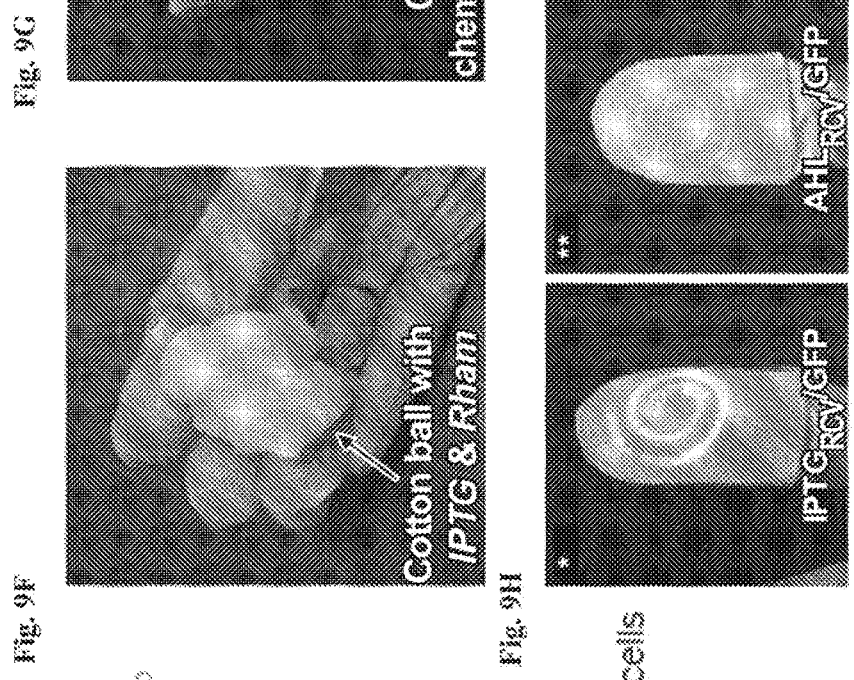
Figure 9H:
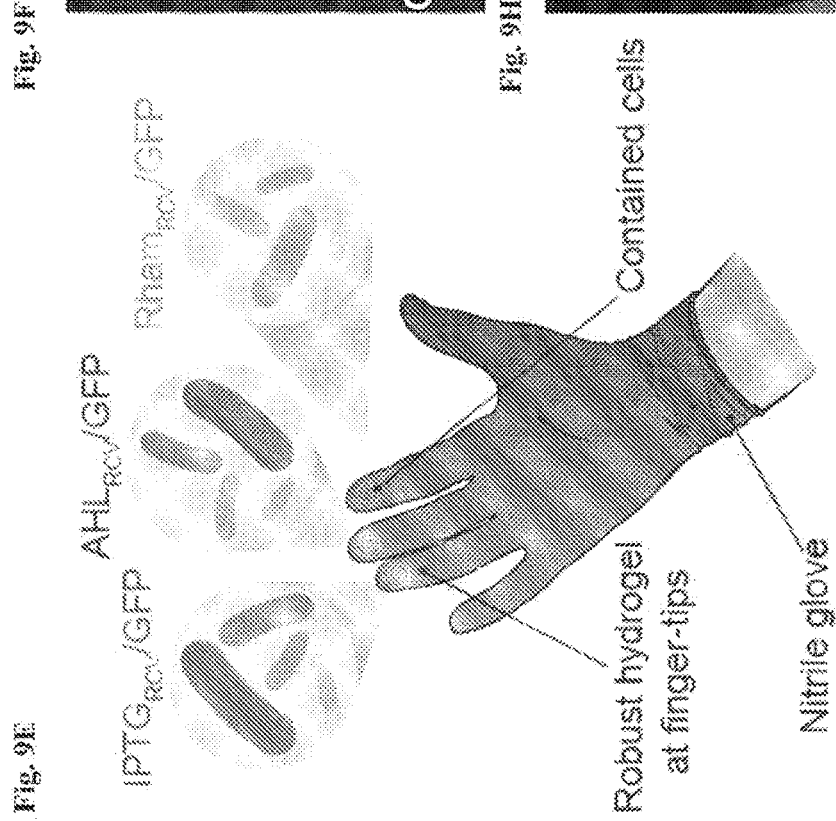

As another application, a glove with chemical detectors integrated at the fingertips was fabricated (FIG. 9E). The stretchable hydrogel and tough bonding between hydrogel and rubber allow for robust integration of living monitors on flexible gloves. To demonstrate the capability of this living glove, a glove-wearer held cotton balls which have absorbed inducers. Those chemicals from the cotton ball would diffuse through the hydrogel and induce fluorescence in the engineered bacteria. For example, gripping a wet cotton ball that contained IPTG and Rham resulted in fluorescence at two of the three bacterial sensors that contained IPTG$_{RCV}$/GFP (*) and Rham$_{RCV}$/GFP (*) on the glove within 4 h. The middle sensor containing AHL$_{RCV}$/GFP () remained unaffected (FIG. 9F-9H). The living patch and biosensing glove demonstrate the potential of living materials as low-cost and mechanically flexible platforms for healthcare and environmental monitoring. Based on these results, the design of new living devices that can be wearable, ingestible or implantable for applications such as water quality alert, disease diagnostics and therapy can be envisioned.

Example 6: Model of Living Materials and Devices

Figure 10A:
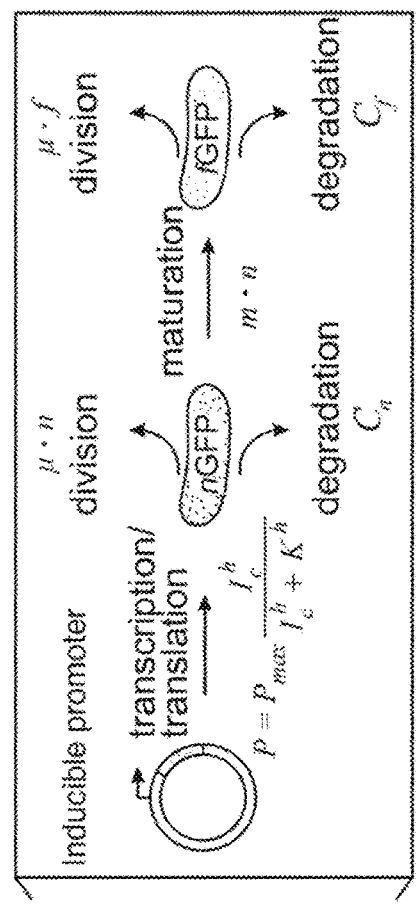
FIGS. 10A-10E show a model for the diffusion-induction process in living materials and devices.

In this section, a model that quantitatively accounted for the coupled physical transportation and biochemical responses underlying the living sensor (FIGS. 9A-9C) was developed. The operation of the living sensor (FIG. 7A) relied on two processes: diffusion of signaling molecules from the environment through the hydrogel window into cell chambers, and induction of the encapsulated cells by the signaling molecules (28). Given the geometry of the sensor (FIG. 10A), the transportation of inducer in the hydrogel and the cell chamber could be approximated to follow the one-dimensional Fick's law $$\frac{\partial I}{\partial t} = D_g \frac{\partial^2 I}{\partial x^2} \text{ for } 0 \leq x < L_g \quad (1)$$

$$\frac{\partial I}{\partial t} = D_c \frac{\partial^2 I}{\partial x^2} \text{ for } L_g \leq x < L_g + L_c \quad (2)$$

where x is the coordinate of a point in the hydrogel window or the cell chamber; $L_g$ and $L_c$ are the thicknesses of the hydrogel and cell chamber, respectively; t is the current time; I is the inducer concentration in hydrogel or medium in the cell chamber, and $D_g$, $D_c$ are the diffusion coefficients of the inducer in hydrogel and medium, respectively.

To prescribe boundary conditions for Eq. 1 and 2, the inducer concentration at the boundary between the environment and the hydrogel window is taken to be a constant $I_0$, the inducer concentration and inducer flux is taken to be continuous across the interface between the hydrogel and cell chamber, and the elastomer wall of the cell chamber is taken to be impermeable to the inducers. Since the diffusion process begins at t=0, the inducer concentration throughout the hydrogel window and cell chamber is zero when t≤0, as the initial condition for Eq. 1 and 2. Furthermore, the consumption of inducers by the bacterial cells was taken to be negligible. In the current experiments, we set $L_g$=5×10$^{-4}$ m, $L_c$=2×10$^{-4}$ m, and $I_0$=1 mM for IPTG diffusion-induction. The diffusion coefficients of inducers are estimated to be $D_g$=3×10$^{-10}$ m$^2$/s, $D_c$=1×10$^{-9}$ m$^2$/s based on previous measurements (29).

Figure 10C:
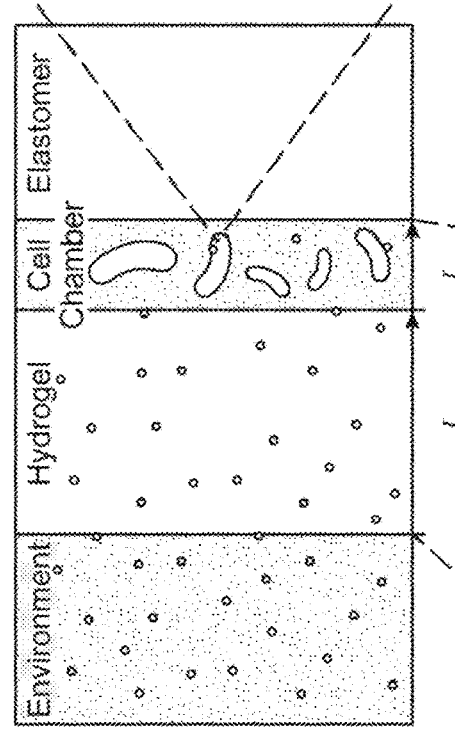
Figure 10B:
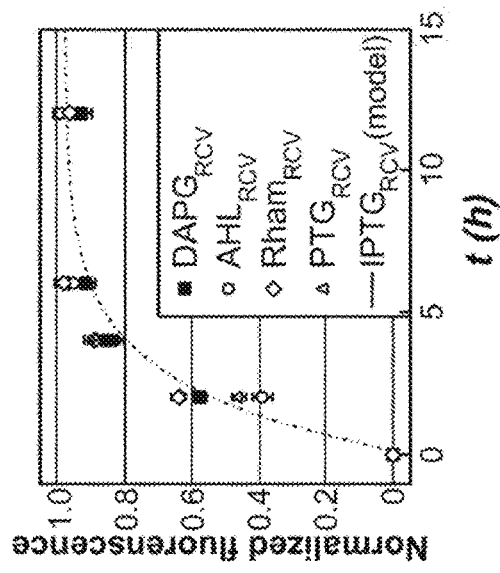
Figure 10D:
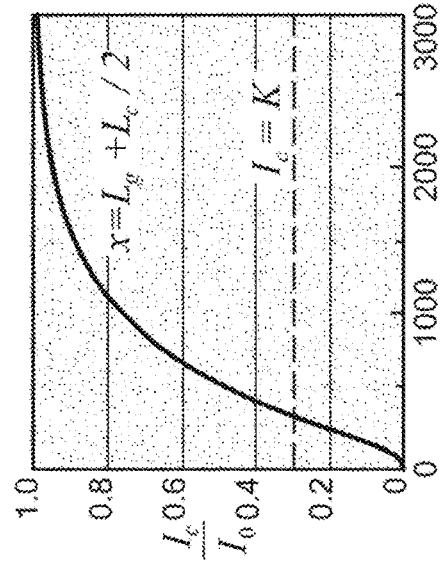

The diffusion equations together with boundary and initial conditions were solved using COMSOL Multiphysics. In FIG. 10C, the inducer concentrations throughout the hydrogel window and cell chamber at different times were plotted. It can be seen that the distribution of inducers in the cell chamber is more uniform than that in the hydrogel due to the higher inducer diffusion coefficient in media than that in hydrogel. The typical inducer concentration $I_c$ was further defined as the inducer concentration at the center of the cell chamber (i.e., $I_c$=I(t,x=$L_g$+$L_c$/2)). In FIG. 10D, the typical inducer concentration in the cell chamber was plotted as a function of time.

To characterize the GFP expression of the bacterial cells in the living sensor, a model from Leveau (30) was adopted. The inducers can bind with repressors or activators in a bacterial cell, and induce the transcription of promoters. The induced promoters initiate the synthesis of nonfluorescent GFP ($^n$GFP). Meanwhile, the $^n$GFP in the cell are consumed due to their maturation into the fluorescent GFP ($^f$GFP), cell division, and protein degradation. The converted $^f$GFP also undergoes consumption due to cell division and protein degradation. Eventually, the syntheses and consumptions of $^n$GFP and $^f$GFP reach steady states in the cell (FIG. 10B). Denoting the numbers of $^n$GFP and $^f$GFP in a cell as n and f respectively, their rates of variation can be approximated as $$\frac{\partial n}{\partial t} = P - m \cdot n - \mu \cdot n - C_n \quad (3)$$

$$\frac{\partial f}{\partial t} = m \cdot n - \mu \cdot f - C_f \quad (4)$$

In Eq. 3 and 4, P is the promoter activity that expresses $^n$GFP, m·n prescribes the maturation rate of $^n$GFP into $^f$GFP where m is the maturation constant, μ·n and μ·f prescribe the consumption rates of $^n$GFP and $^f$GFP due to cell division where μ is the growth constant, $C_n$ and $C_f$ are the degradation rates of $^n$GFP and $^f$GFP, respectively. The promoter activity for transcription and translation induced by an inducer is approximated by a Hill equation (31)

$$P = P_{max} \frac{I^h}{I^h + K^h},$$

in which $P_{max}$ is the maximum rate of $^n$GFP expression (i.e., maximum promoter activity), h is the Hill coefficient, K is the half-maximal parameter (inducer concentration at which P equals 0.5$P_{max}$). Since the inducer concentration in the cell chamber is relatively uniform (FIG. 10C), I in the promoter activity expression is taken to be the typical concentration in the cell chamber (i.e., I=$I_c$). Evidently, the connection between the transportation of inducers and biochemical responses of cells in the living sensor is through this Hill equation. Since the half-life of GFP in *E. coli* is over 24 h in absence of any proteolytic degradation, much longer than the typical responsive time of the living sensor, we assume $C_n=C_f=0$ throughout the current study. For the IPTG$_{RCV}$/GFP strain, $P_{max}=1000$ s$^{-1}$, $K=0.3$ mM, $h=2$, $m=1.16\times10^{-2}$ s$^{-1}$, and $\mu=1.20\times10^{-4}$ s$^{-1}$ based on previously reported data on this system (30, 32).

Figure 10E:
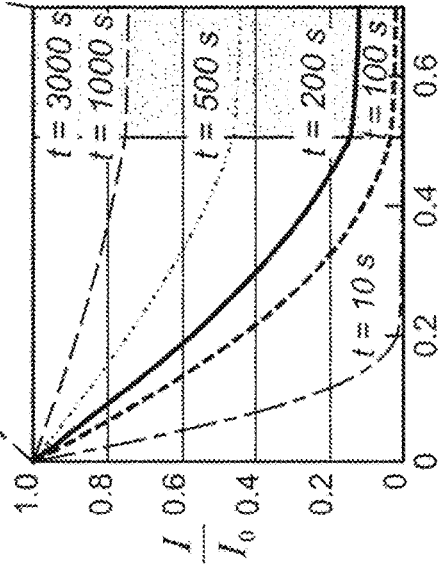

In FIG. 10E, the normalized fluorescence of cell in the device was plotted as a function of time after the inducers are added outside the living device. It takes around 2 h for different strains in the living sensor to demonstrate significant fluorescence (e.g., 0.5 of the maximum fluorescence). For the IPTG$_{RCV}$/GFP strain, the diffusion-induction coupled model matches very well with experimental data (FIG. 10E).

Example 7: Critical Time Scales for Living Materials and Devices

Figure 20A:
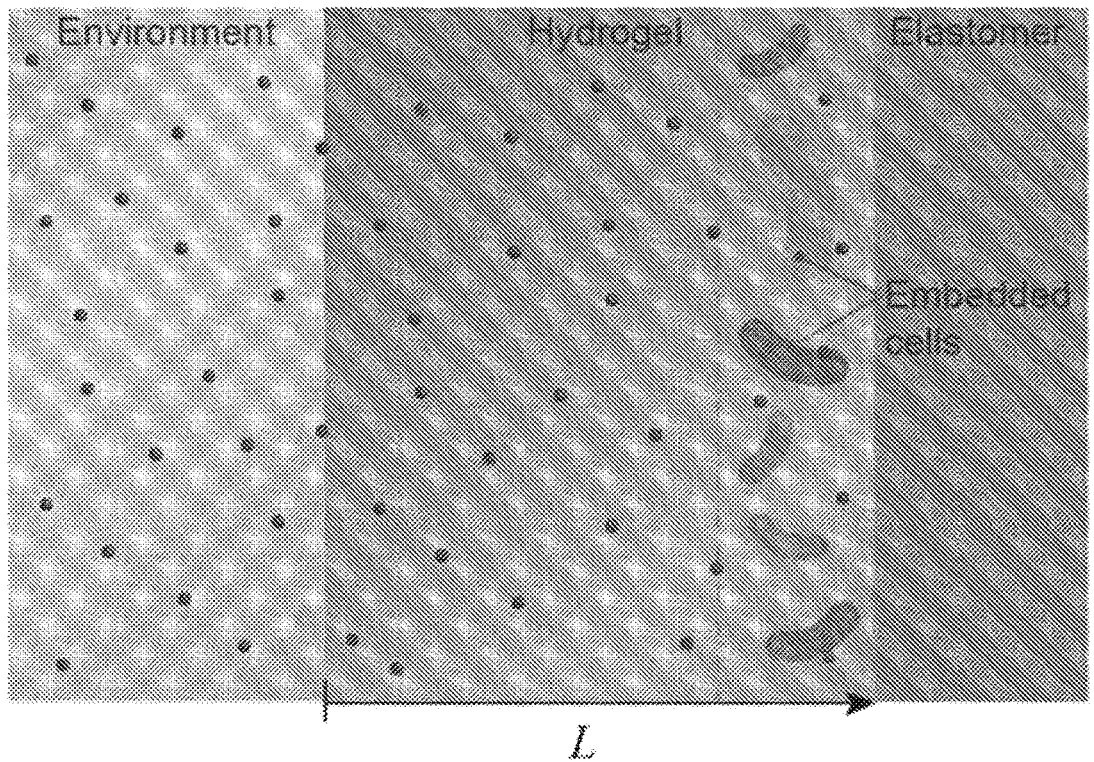
FIGS. 20A-20B show calculation of critical diffusion time scales for living materials and devices.
Figure 20B:
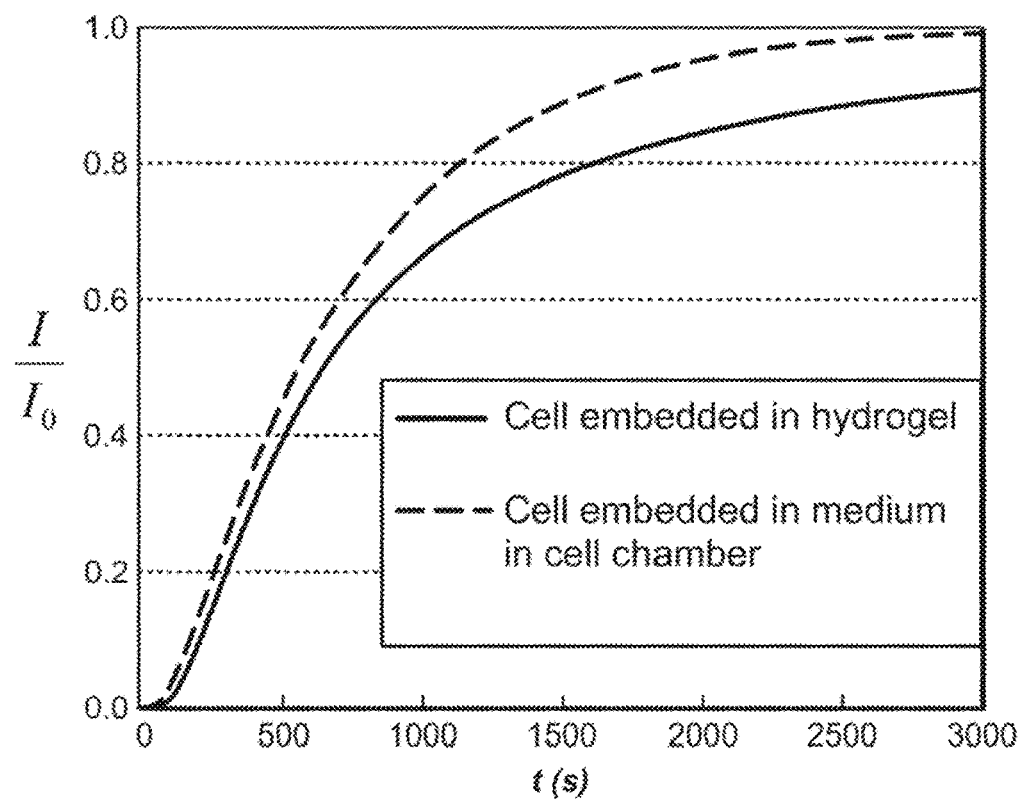
Figure 21:
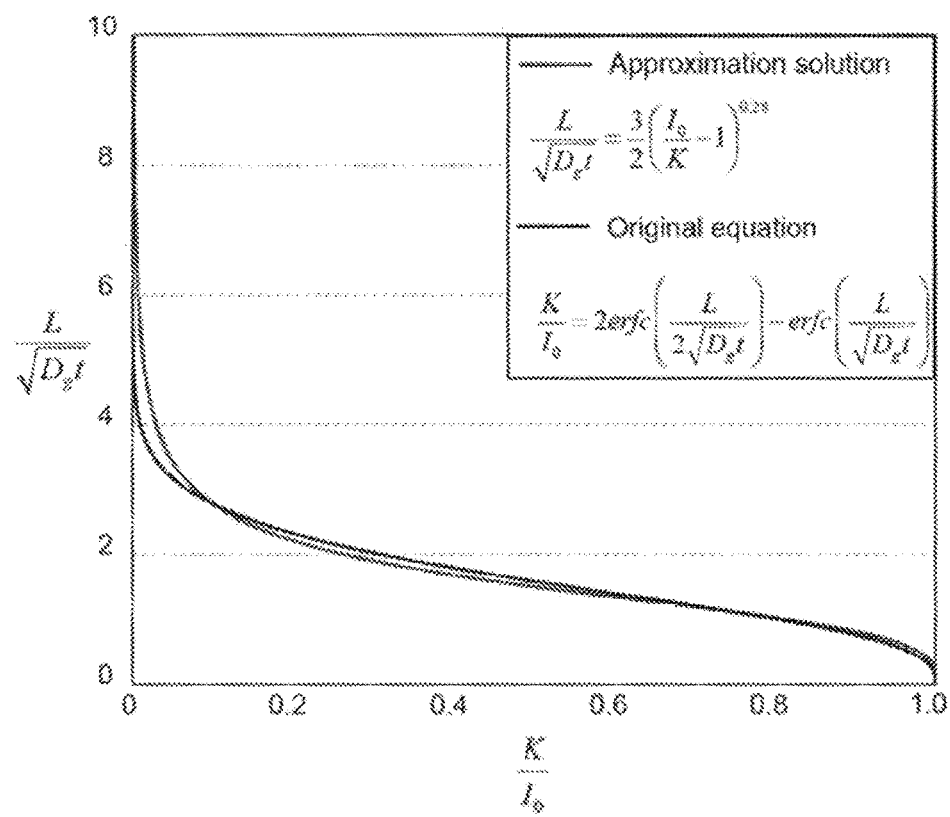
FIG. 21 shows approximate diffusion time scale. The expression of $$\frac{K}{I_0} = 2\mathrm{erfc}\left[\frac{L}{2\sqrt{D_g t}}\right] - \mathrm{erfc}\left[\frac{L}{\sqrt{D_g t}}\right]$$

From the above analysis, it is known that the responsive time of a living material or device is determined by two critical time scales: the time for inducers to diffuse and accumulate around cells to the level that is sufficient for induction $t_{diffuse}$, and the time to induce GFP expression and reach a steady state $t_{induce}$. To obtain analytical solutions for $t_{diffuse}$, a simple yet relevant model was developed, as illustrated in FIG. 20A. The model is similar to the geometry of the living sensor (FIG. 10A), but assumes that the cells are embedded in a segment of hydrogel close to the elastomer wall. The inducer concentration in the environment is taken to be constant $I_0$ and the total thickness of the hydrogel is L. By means of multiple imaginary sources (33), the inducer concentration at location L (at the end of hydrogel) and time t can be expressed as $I(L,t)/I_0 = 2\mathrm{erfc}[L/(2\sqrt{D_g t})] - \mathrm{erfc}[L/(\sqrt{D_g t})]$, where erfc(x) is the complementary error function. From FIG. 20B, it can be seen that the simplified model can consistently represent the typical concentration profile in the cell chamber of the living sensor. From promoter activity expression, it was assumed that only when the inducer concentration at a point reaches the level of K (i.e., $P=P_{max}/2$), the inducer concentration is sufficient to induce the cells. Therefore, the critical diffusion time for cells with a typical distance L from the environment is $$t_{diffuse} = [\Lambda(K/I_0)]^{-2} * L^2/D_g \quad (5)$$

where $\Lambda(x)$ is the inverse of function of $$\Omega(x) = 2\mathrm{erfc}\left(\frac{x}{2}\right) - \mathrm{erfc}(x), \; L^2/D_g$$

is the typical diffusion time scale, and the pre-factor $[\Lambda(K/I_0)]^{-2}$ accounts for the difference between $I_0$ and K. The pre-factor was further fitted into a power law that approximately gives $t_{diffuse} \approx 4/9/(I_0/K-1)^{0.56}*L^2/D_g$ (FIG. 21).

The time scale to induce the cell $t_{induce}$ was next evaluated. When the inducer concentration around a cell reaches the level of K (i.e., P reaches the level of $0.5P_{max}$), significant induction (e.g., expression of GFP) will occur in the cell. To solve Eq. 3 and 4 analytically, it was assumed that the induction happens only after P reaches the level of $0.5P_{max}$, and P maintains at a constant level (between $0.5P_{max}$ and $P_{max}$) during the induction. Therefore, n=f=0 can be set as the initial condition and P as a time-independent constant in Eq. 3 and 4. Further setting $C_n=C_f=0$, analytical solutions $n=P(1-e^{-(m+\mu)t})/(m+\mu)$ for $^nGFP$ and $f=P(e^{-(m+\mu)t}-1)/(m+\mu)-P(e^{-\mu t}-1)/\mu$ for $^fGFP$ can be obtained, from which two characteristic time scales [i.e., $1/(m+\mu)$ and $1/\mu$] can be identified. Evidently, the characteristic time scale for the expression of $^nGFP$ is $1/(m+\mu)$. Since the maturation constant m is usually much larger than the growth constant $\mu$ (30, 34), the second term of GFP has a much larger coefficient than the first term, and thus the second term dominantly characterizes the expression of GFP with a critical time scale of $1/\mu$. Therefore, the critical time to induce cells to reach steady-state fluorescence was approximated as $$t_{induce} \approx \frac{1}{\mu} \quad (6)$$

Based on the known parameters for IPTG$_{RCV}$/GFP cells encapsulated in hydrogel at a typical distance of L (0.7 mm) from the environment, the critical time scales of diffusion and induction were estimated to be 7.5 min and 140 min, respectively. The induction of cells takes much longer time than the transportation of inducers, which is consistent with the full model (FIGS. 10D and 10E). In total, the coupled diffusion-induction time scale is 2.4 h, which is also in good agreement with the full model's prediction (FIG. 10E).

The above analysis can provide a few guidelines for the design of future living materials. In order to design living materials and devices with faster responses, shorter times for both $t_{diffuse}$ and $t_{induce}$ are needed. In order to decrease $t_{diffuse}$ (Eq. 5), one can (a) reduce the thickness of the hydrogel, (b) increase the diffusivity of inducer in the hydrogel, and (c) increase the inducer concentration in the environment. On the other hand, in order to decrease $t_{induce}$, one can design cells with higher maturation constants or growth constants, and add negative feedback into genetic circuit (31).

Example 8

One design for bacterial encapsulation included two parts: 1) a natural polymer core and 2) a tough hydrogel shell (FIGS. 1A-1D). The core was made out of alginate because of its biocompatibility, low toxicity, cheap cost, and simple gelation mechanism. For the shell, a hydrogel was engineered, which combines a stretchy polymer network (polyacrylamide) and an energy dissipation mechanism (alginate), which has been demonstrated to be extremely tough and robust.

To incorporate living cells, a liquid culture of *E. coli* was mixed with alginate into droplets that were crosslinked with calcium ions to form spheres. The cell-containing alginate hydrogel could be easily cast into different shapes (data not shown). Cores were then coated with the tough polyacrylamide-alginate hydrogel layer. In the core-shell system, the alginate core supports growth by supplying nutrients while the hydrogel shell provides mechanical protection for the entire bead. For downstream analyses after deployment, cells can be retrieved from the beads by removing the shell and homogenizing the core (FIG. 1E). The mechanical properties of the beads (r=2.5 mm) were tested by submitting them to compression, and they could withstand 25.84% compressive strain before fracturing occurred (FIG. 1B). The force needed to fracture the shell was 0.108 N, which corresponds to ~170 times the gravitational force exerted by an individual bead.

Example 9

In addition to providing excellent mechanical properties, the tough hydrogel layer serves as a containment mechanism because its pore size (5-50 nm) is too small for *E. coli* to penetrate. To demonstrate this, the containment efficiency of the hydrogel beads by incubating them at the optimal temperature for *E. coli* growth (37° C.) with shaking. Beads lacking a tough shell allowed bacteria to escape into the surrounding medium and grow to high densities after overnight incubation, whereas coated beads showed no bacterial escape even after 72 hours of incubation (FIG. 1C).

The protective effects of the beads were investigated by comparing the resistance of encapsulated cells versus planktonic cells (without bead encapsulation) to a series of physical, chemical, and biological stresses (FIG. 1D). Encapsulated bacteria survived to a much greater extent (>100-fold) than planktonic cells in the presence of the aminoglycoside antibiotic kanamycin. Encapsulation also helped cells survive acidic environments (pH 3). Both protective effects may be attributed to ionic interactions between positively charged kanamycin molecules or $H^+$ ions and anionic alginate chains (18, 26). On the other hand, encapsulation did not prevent cell death at freezing conditions (−80'C), which is not entirely surprising because the water content is high in hydrogel-based systems. Thus, the robust hydrogels can provide protective housing for GMMs and enhance their survivability in certain stressful conditions.

Example 10

To show that bacterial cells could stay metabolically active inside the beads, an *E. coli* strain that expresses GFP in response to IPTG was encapsulated, and its growth inside the beads was measured. The number of cells in the beads increased by ~$10^5$ fold (~16-17 generations) and reached stationary phase after 12 hours of incubation, corresponding to a doubling time of ~40 minutes. This data indicates that bacterial cells within the beads were metabolically active and able to divide in the alginate core.

To show that encapsulated bacteria can respond to external stimuli, bacteria were encapsulated with a genetic construct that expresses GFP in response to IPTG induction. The beads were then incubated at 37° C. in 1 mM IPTG and found that encapsulated cells exhibited bright green fluorescence after induction (FIG. 2A). In contrast, encapsulated cells not exposed to IPTG exhibited minimal fluorescence, therefore demonstrating the inducibility of gene expression of the cells encapsulated within the tough hydrogels.

It was then shown that engineered bacteria with genomically encoded memory that requires cell division to function performs within the beads. The SCRIBE platform (Farzadfard, T. K. Lu, *Science* 346, 1256272 (2014)) enables targeted in vivo genome editing for recording information in living cells. A high-efficiency version of SCRIBE 1) expresses single-stranded DNA in vivo to write mutations into genomic DNA, 2) produces Beta recombinase to enhance recombination efficiency, and 3) leverages CRISPR interference (CRISPRi) to represses native exonucleases in order to maximize genome editing. This SCRIBE circuit was designed so that IPTG and aTc controlled the expression of Beta recombinase and the CRISPRi system, respectively; both of these inducers are required to achieve high-efficiency in vivo gene editing of the kanR gene (FIG. 2B, left). Beads containing SCRIBE bacteria were exposed to IPTG and aTc over 48 hours and found that increasing numbers of bacteria acquired kanamycin resistance over the first 12 hours (FIG. 2B, right). The high recombinant frequency (~10%) by 12 hours is comparable to results obtained using liquid cultures of unencapsulated bacteria, and the plateau in recombination frequency after 12 hours corresponded to growth saturation.

Figure 2C:
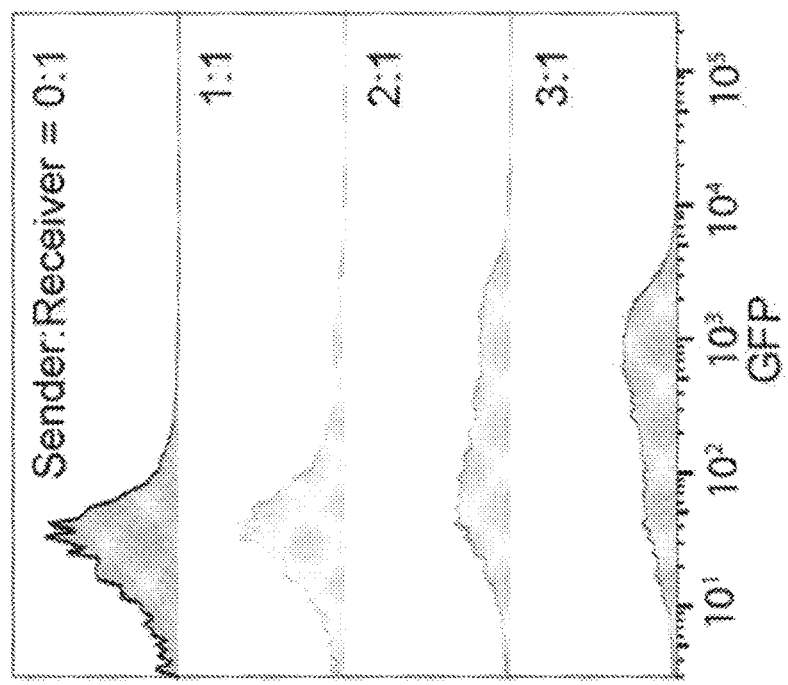
Figure 2C:
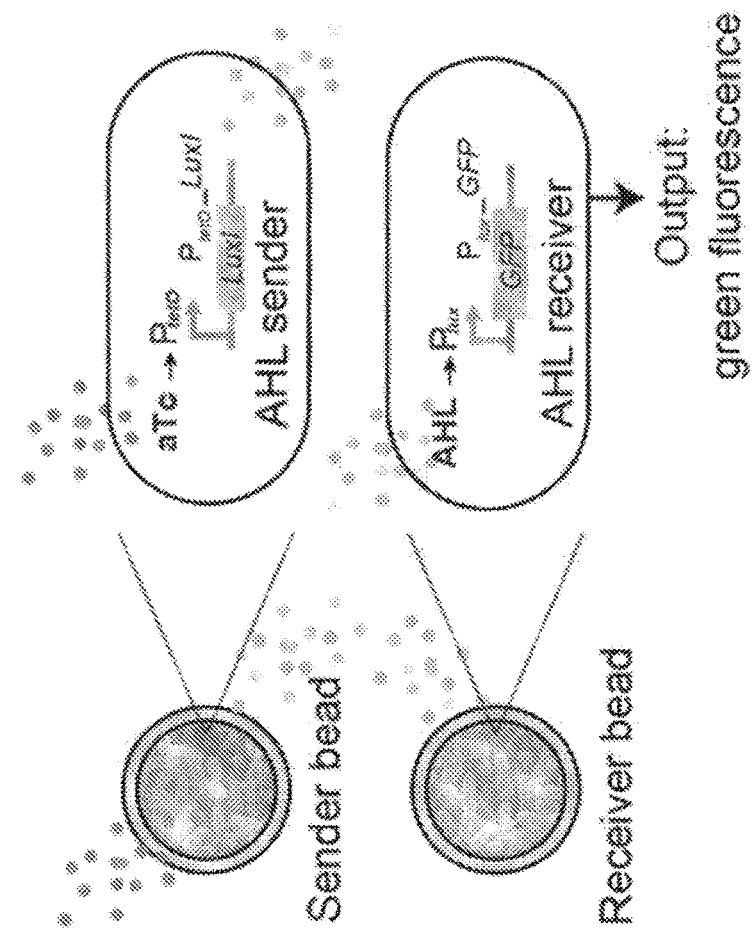

Finally, it was shown that different *E. coli* strains contained within beads could communicate with each other via small molecule quorum-sensing "chemical wires". An acyl homoserine lactone (AHL) sender strain and an AHL receiver strain were encapsulated in separate beads and incubated together in 1 mL of media (FIG. 2C, left). Upon receiving externally added aTc, the sender bead produced AHL, which diffused through the hydrogel structures and induced GFP expression in the neighboring receiver bead. The receiver beads exhibited intensified fluorescence as more sender beads were used (FIG. 2C, right). These results suggest a modular and distributed strategy for collective execution of complex tasks that require division of labor using multiple beads containing distinct bacteria with cell-to-cell communication.

Example 11

Figures 3A, 3B, 3C:
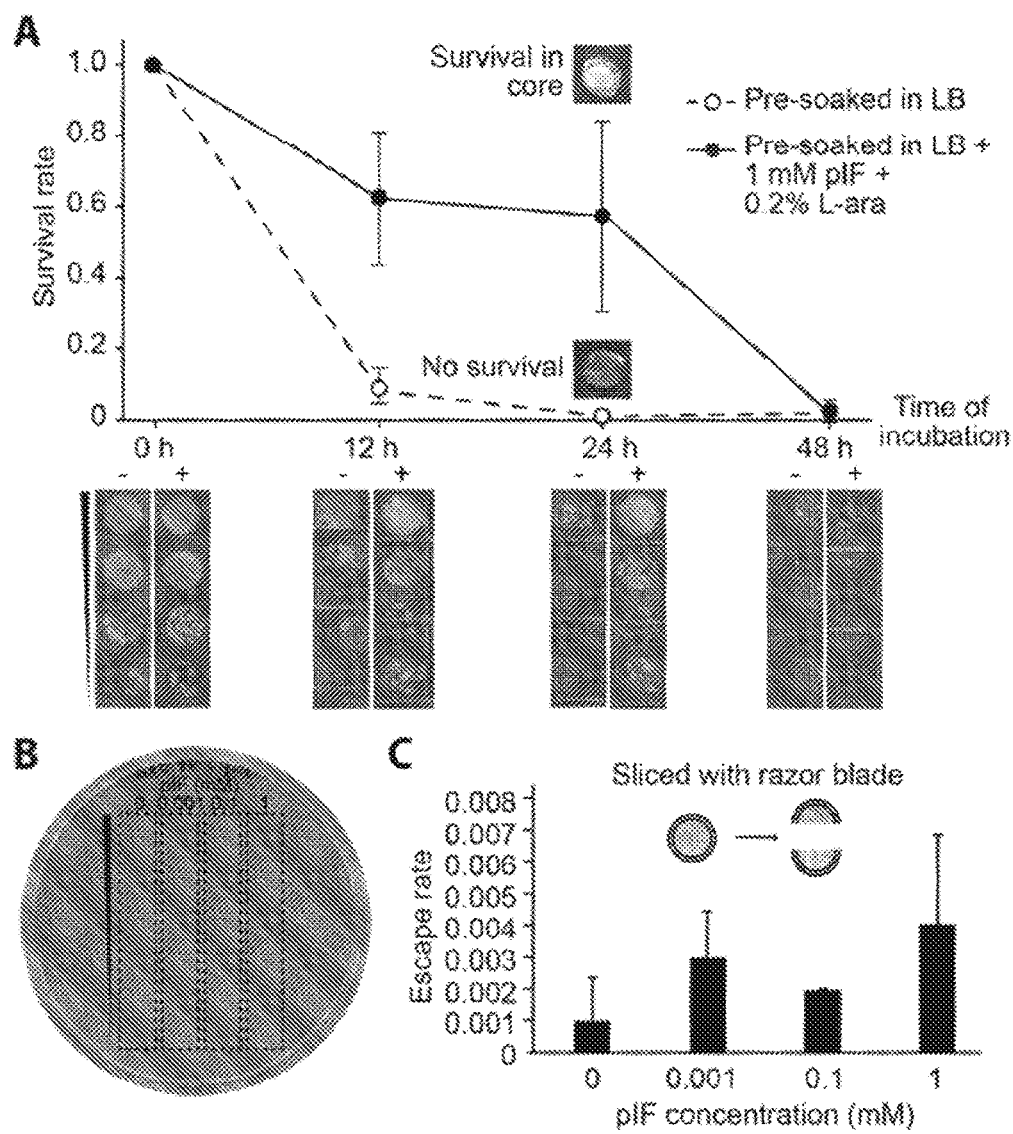
FIGS. 3A-3C shows combining chemical and physical strategies for optimal biocontainment.

Given the highly permeable nature of the hydrogels, it was thought that chemical containment could be employed to enforce an additional layer of control over encapsulated cells. Biological containment has been realized through designs that rely on inducible kill switches, programmed cell lysis, and engineered auxotrophy. GROs can be contained because the growth of these recoded organisms is dependent on the supply of synthetic amino acids. Such an organism, when encapsulated in the tough hydrogel, had a low escape rate and resistance to horizontal gene transfer (FIGS. 3A-3C).

Here, physical and chemical strategies were combined for biocontainment by encapsulating a GRO auxotrophic for the synthetic amino acid p-azido-phenylalanine (pIF) in tough hydrogel beads. First, beads encapsulating the pIF auxotroph GRO (rEc.β.dC.12'.ΔtY) were pre-soaked in LB in the absence (control) or presence of 1 mM pIF and 0.2% L-arabinose (L-ara, required for aaRS expression). Without pIF and L-ara, these rEc.β.dC.12'.ΔtY cells should not be able to synthesize functional essential proteins and should lose viability. Indeed, beads pre-soaked in LB without pIF and L-ara (control) failed to sustain cell growth and showed less than 10% survival after 12 hours in LB only (FIG. 3A). On the other hand, when the beads that had been pre-soaked in LB with pIF and L-ara were washed and transferred to fresh LB medium, they gradually released pIF and L-arabinose to their surroundings until the core was depleted of these amino acids. Pre-soaking encapsulated beads in pIF and L-ara greatly improved cell survival, which was reflected by the fact that more than half of the bacterial population stayed viable after one day of incubation. Nearly all cells lost viability after 2 days of incubation, which was attributed to pIF and L-ara consumption by cells, as well as to passive diffusion of these amino acids out of the encapsulated hydrogel. Because most of the chemical induction and sensing responses in *E. coli* require less than 24 hours to complete, this narrow yet adequate growth window may be leveraged to prevent undesirable growth of cells upon completion of tasks. The combinatorial effect of physical and chemical containment is shown in FIG. 3B. No viable cells were observed in the surrounding medium at the end of a 6-day incubation period, indicating complete containment.

In some instances, the hydrogel shell might be mechanically compromised, which would result in the release of the GRO into the environment. In addition, the free diffusion of artificial amino acids might be hindered by conditions such as small local volumes leading to limited dilution of the chemicals. To further investigate the risk of escape due to shell fracture and imperfect dilution, hydrogel beads encapsulating rEc.β.dC.12'.ΔtY cells supplemented with different concentrations of pIF were physically sliced open with a razor blade and incubated in small volumes (10 mL) of LB medium (FIG. 3C). After 2 days of incubation, the alginate cores dissolved and some cells escaped and stayed viable in the medium, though the escaped cells represented less than 0.4% of the cells. These results suggest that although combining physical and chemical containment provides near-zero escape rates, risk factors such as fracture and limited dilution should also be taken into account in the experimental design.

Example 12

An *E. coli* strain was used to detect the presence of cadmium ions in water samples from the Charles River. To regulate GFP expression, PzntA, a promoter activated by the transcriptional regulator ZntR upon binding to metal ions ($Zn^{2+}$, $Pb^{2+}$, $Cd^{2+}$) was used. Once *E. coli* was transformed with a plasmid encoding PzntA, we characterized the induction of PzntA by $Zn^{2+}$, $Pb^{2+}$, and $Cd^{2+}$ in liquid cultures (FIG. 4A) and decided to focus the studies on $Cd^{2+}$, as it is a well-known and widespread environmental contaminant that can adversely affect human health. While encapsulated in hydrogel beads and incubated in LB medium for a total of three hours, cells produced green fluorescence intensities proportional to $Cd^{2+}$ concentrations (FIG. 4B).

Figures 4A, 4B, 4C, 4D:
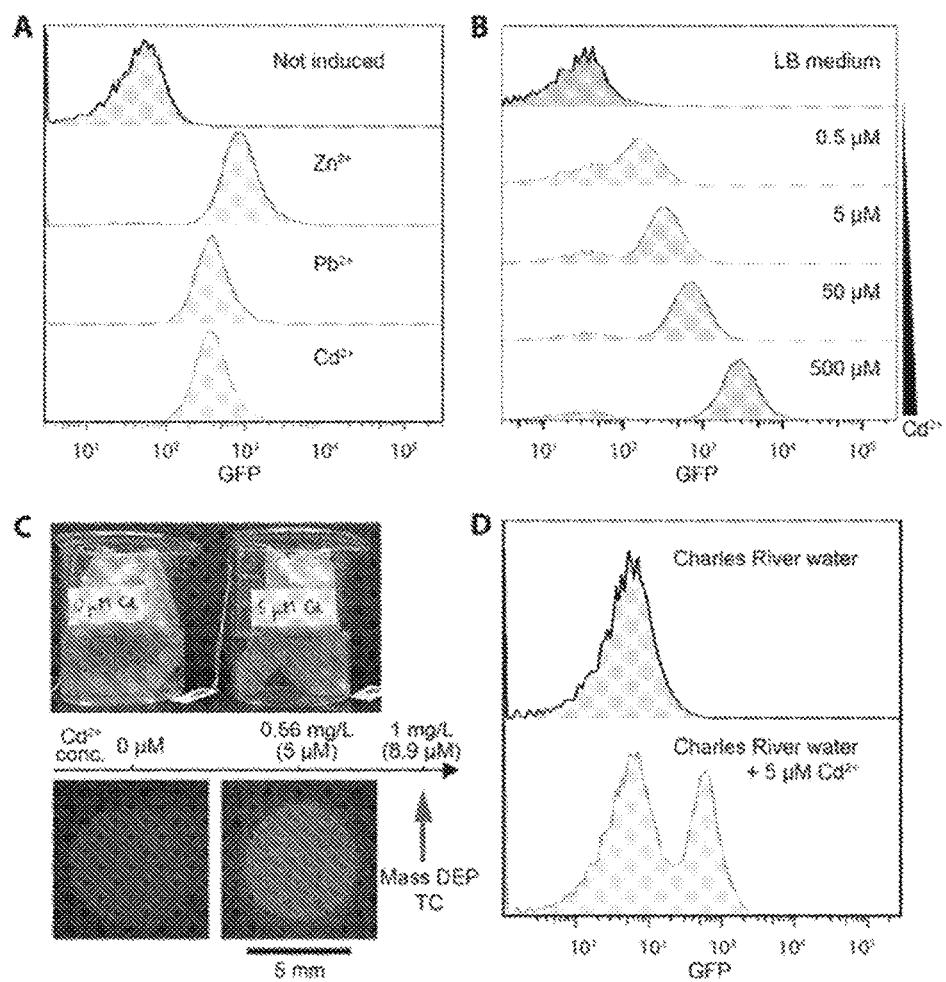
FIGS. 4A-4D show heavy metal sensing in river water samples.
Figure 4E:
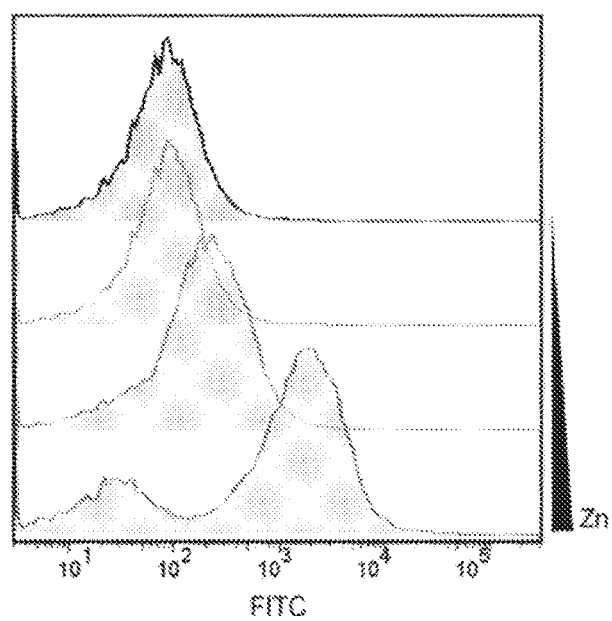
FIG. 4E shows heavy metal ion sensing *E. coli* strain encapsulated in a tough hydrogel for environmental monitoring.
Figure 5A:
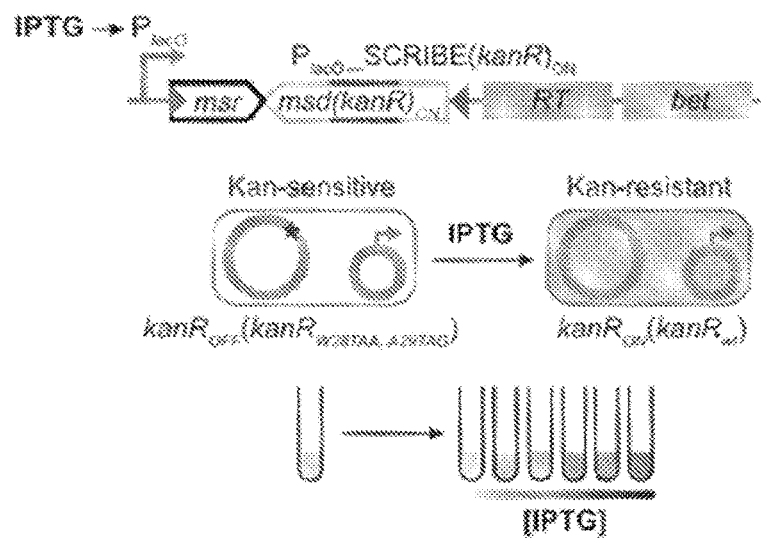
FIGS. 5A-5B show Synthetic Cellular Recorders Integrating Biological Event (SCRIBE) (Farzadfard, T. K. Lu, *Science* 346, 1256272 (2014); and WO 2016/025719, each of which is incorporated herein by reference) in tough hydrogel.
Figure 5A:
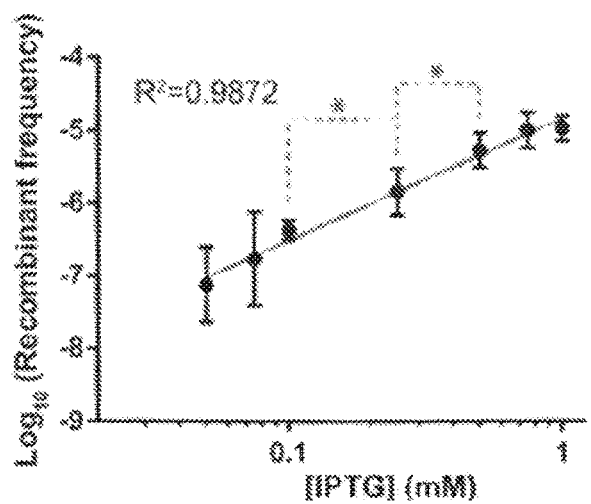
Figure 5B:
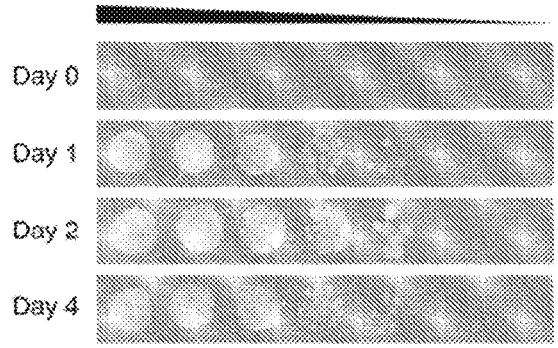

The hydrogel-bacteria beads (pre-soaked in 4×LB) were incubated in water samples extracted from the Charles River, and exogenously added $Cd^{2+}$ at various concentrations (teabags were used for efficient deployment and retrieval) (FIG. 4C top). An additional peak was observed in the GFP profile after exposure to 5 μM $CdCl_2$ (FIG. 4D), indicating successful detection of cadmium ions. These results were also observed visually under blue light: beads exposed to 5 μM $CdCl_2$ exhibited strong green fluorescence (FIG. 4C bottom). This sensitivity is well below the 8.9 μM (1 mg/L) standard defined by the Massachusetts Department of Environmental Protection as the maximum concentration of cadmium allowed in waste water. Thus, these results highlight the potential of the biocontained bacteria to detect toxic levels of heavy metals in environmental settings.

Materials and Methods
Fabrication of Living Device

Different cell strains were picked from overnight growth on LB plates and cultured in LB media with 50 μg/mL carbenicillin at 37° C. Cell cultures ($OD_{600}$≈1) were infused into the patterned cavities between hydrogel and elastomer by metallic needles (Nordson EFD) through the hydrogel layer (FIGS. 13A-13C). The holes induced by cell injection were sealed with small amounts of fast-curable pre-gel solution. The cell contained device was washed with PBS three times, followed by immersing the device in LB broth with carbenicillin and inducer(s) at 25° C.

Materials

The hydrogel was composed of two types of crosslinked polymers: ionically crosslinked alginate and covalently crosslinked polyacrylamide (PAAm). For the stretchy PAAm network in hydrogel, acrylamide (AAm; Sigma-Aldrich A8887) was used as the monomer, N,N-methylenebisacrylamide (MBAA; Sigma-Aldrich 146072) as the crosslinker, and 2-hydroxy-4'-(2-hydroxyethoxy)-2-methylpropiophenone (Irgacure 2959; Sigma-Aldrich 410896) as the photo-initiator, respectively. Calcium sulfate (Sigma-Aldrich C3771) slurry acted as the ionic crosslinker with sodium alginate (Sigma-Aldrich A2033) for the dissipative network. As for elastomers, SYLGARD® 184 (polydimethylsiloxane; Dow Corning) or Ecoflex (Smooth-On) were molded and activated with benzophenone (Sigma-Aldrich B9300). Purple Nitrile Exam Gloves (Kimberly-Clark) were also used as an elastomer substrate. Ammonium persulphate (APS; Sigma-Aldrich A3678) as a thermo-initiator and N,N,N',N'-tetramethylethylenediamine (TEMED; Sigma-Aldrich T9281) as a crosslinking accelerator were used in the fast-curable pre-gel solution for sealing of injection points. For cell induction, 2,4-diacetylphloroglucinol (DAPG; Santa Cruz Biotechnology sc-206518), N-(β-ketocaproyl)-L-homoserine lactone (AHL; Sigma-Aldrich K3007), isopropyl β-D-1-thiogalactopyranoside (IPTG; Sigma-Aldrich 15502), L-rhamnose (Rham; Sigma-Aldrich W373011), and anhydrotetracycline (aTc; Sigma-Aldrich 37919), were used as the signaling molecules. Carbenicillin (Sigma-Aldrich C1389) was added as an antibiotic in the LB-Miller medium (Sigma-Aldrich L3522) for cell culture. LIVE/DEAD BacLight bacterial viability and counting kit (Sigma-Aldrich L34856) was used for cell viability assay.

Fabrication of Hydrogel and Elastomer Hybrid

Elastomers with microstructured cavities were prepared by soft lithography with the feature size of 500 μm in width and 200 μm in depth. Then, the prepared microstructured elastomer was assembled with hydrogel to form robust hydrogel-elastomer hybrid as described in the previous report (15). Briefly, the surface of the elastomer was treated with 10 wt. % benzophenone solution in ethanol for 10 min, then washed and dried with nitrogen. The pre-gel solution (12.05 wt % acrylamide, 1.95 wt % sodium alginate, 0.2 wt % Irgacure 2959, and 0.012 wt % N,N-methylenebisacrylamide) was carefully degassed, and mixed with calcium sulfate slurry ($2 \times 10^{-2}$ M in pre-gel solution) to form physically-crosslinked hydrogel. To introduce robust bonding between assembled hydrogel and elastomer, the physically-crosslinked hydrogel was assembled with the surface treated elastomer followed by UV irradiation (365 nm; UVP CL-1000) for 30 min. The resultant hydrogel-elastomer hybrid was washed with phosphate-buffered saline (PBS) for three times, sterilized using germicidal UV irradiation thoroughly, and immersed in LB media with antibiotics for 12 h before bacterial cell seeding. Fast-curable pre-gel solution (30.05 wt % AAm, 1.95 wt % sodium alginate, 0.012 wt % MBAA, 0.142 wt % APS, and 0.10 v % TEMED), which could be cured at room temperature in 5 min, is used for sealing the holes after cell seeding.

Bacterial Strains and Plasmids

The plasmids used in this study were constructed with standard molecular cloning techniques. To create constructs for the expression of output genes under tight regulation by DAPG, IPTG, AHL or Rham inducible promoters, pZE-AmpR-pL(lacO)-gfp (IPTG inducible) was used as a starting point. All promoters were amplified using polymerase chain reaction (PCR) and inserted in place of pL(LacO) by Gibson assembly. The corresponding repressors or activators, which can interact with small molecule inducers, were inserted into the *E. coli* genome or cloned onto the same plasmid that harbors the promoter-gfp output module. For example, the proteins PhlF and LacI repressed DAPG and IPTG inducible promoters, respectively. PhlF was inserted in a plasmid under regulation of proD promoter, whereas the LacI repressor was already present in the genome of DH5αPRO. Similarly, the AHL-inducible transcriptional activator, LuxR, was constitutively expressed from a plasmid and can activate promoter pLuxR upon binding to AHL. The regulatory components necessary for Rham induction were already present in E. coli genome and did not required further engineering. To construct the AHL sender plasmid, LuxI was put onto a plasmid under the regulation of aTc-inducible promoter PLtetO. Finally, all ligations for plasmid construction were transformed into E. coli strain DH5αPRO with standard protocols, and described in FIGS. 18A-18E.

Cell Induction in the Living Device

The cell contained device was immersed in LB broth with carbenicillin and inducer(s) at 25° C. as mentioned in the main text. Inducers could be added in LB medium at final concentrations of 100 μM DAPG, 100 nM AHL, 1 mM IPTG, 12 mM Rham, and/or 200 ng/ml aTc. Alternatively, a piece of sterilized tissue paper (Kimtech) was dipped in LB medium with inducer in it, and was put on top of the hydrogel layer. The device and the tissue paper were kept at 25° C. and relative humidity of 90%. The latter method was not only applicable for cell to receive inducers from the environment (e.g., induction of $IPTG_{RCV}$/GFP by IPTG), but also more suitable for intercellular communication when dilution of signaling molecules by the environment was undesirable. Every induction/detection experiment was performed and repeated at least three times.

Cell Viability Assay

By utilizing the LIVE/DEAD BacLight kit in combination with flow cytometry, the cell viability assay was conducted for cells retrieved from devices and live/dead controls. The fluorescent LIVE/DEAD BacLight viability kit consists of two stains: the green fluorescent nucleic acid stain SYTO 9, which stains the nucleic acids of both living and dead bacteria, and the red fluorescent nucleic acid stain propidium iodide, which only stains bacteria that have damaged and leaky membranes. $Rham_{RCV}$/GFP bacterial suspensions were retrieved from the device by poking a hole from the hydrogel using metal needles after 12 h, 24 h, 48 h, and 72 h culturing. Live-cell controls (untreated) and dead-cell controls (isopropyl alcohol-treated) were set as standards. A diluted bacterial suspension and the LIVE/DEAD BacLight solution were mixed together and incubated at room temperature protected from light for 15 min. The stained cell samples were then analyzed by an LSR-Fortessa flow cytometer (BD Biosciences). For each sample at least $10^4$ events were recorded using a flow rate of 0.5 μL/s. FlowJo (TreeStar) was used to analyze the data. All events were gated by forward scatter and side scatter. In FIGS. 14A-14D, green fluorescence denotes both live and dead bacteria, and the red fluorescence denotes bacteria that have been damaged and leaky membranes. The distributions of the live and dead populations were distinguished in the cytograms.

Cell Escape Test

An intact hydrogel-elastomer living device, and a defective living device (with weak hydrogel-elastomer bonding) were tested for comparison. Also, the agar hydrogel with the same dimensions as the hydrogel-elastomer hybrid and encapsulating $Rham_{RCV}$/GFP bacteria was used as a control. The living materials, which contained $Rham_{RCV}$/GFP bacteria in different modes (i.e., twisting and stretching), were first deformed and then immersed in LB media for 24 h. To test the bacteria leakage, LB solutions surrounding the device were collected for streaking on LB agar plates after 24 h, and optical density (OD) 600 measurements by UV-Visible spectrophotometer (Thermo Scientific) after 6, 12, 20, and 24 h.

In addition, agar hydrogel with bacteria encapsulated were prepared: 1.5 wt % of agar was dissolved in water at 90° C. When the agar solution cooled down to ~40° C., the $Rham_{RCV}$/GFP bacteria was mixed with the solution. As it continued to cool down, the solution could solidify and became a gel.

GFP Expression Assay

For quantitative measurement of GFP expression, the bacteria were isolated from the device by 32 G needles and diluted to $10^7$ cells/mL. Single cell fluorescence was measured using an LSRFortessa flow cytometer with a 488-nm laser for GFP. For each sample, at least $10^4$ events were recorded using a flow rate of 0.5 μL/s. FlowJo was used to analyze the data. All events were gated by forward scatter and side scatter. Integration of cell numbers over fluorescence was calculated and normalized to the maximum fluorescence. For qualitative observation of GFP expression by the naked eye, the living devices were exposed to a benchtop UltraSlim blue light transilluminators (New England Biogroup, wavelength 470 nm). The green channel was extracted from optical images, and the exposure adjusted by setting Gamma correction to 0.2 in Adobe Photoshop CS6 (Adobe). Microscopic observation was done by the aid of a fluorescent microscope (Nikon, Eclipse LV 100ND), and all imaging conditions, such as beam power and exposure time, were maintained the same across different samples.

Preparation and Testing of Sensor Patch on Skin

The robust hybrid patches with wavy microchannels were fabricated by using hydrogel (PAAm-alginate) and silicone elastomer (SYLGARD® 184) following the previously described method. Bacterial suspension of $Rham_{RCV}$/GFP was infused to the upper two channels, and $AHL_{RCV}$/GFP to the lower two channels of the patch. Before the living patch was adhered on forearm, the skin was smeared with LB medium of 12 mM Rham and/or 100 nM AHL. Note these two inducers are non-toxic, safe to be applied on skin. The living patch was conformably mounted on the skin with the PDMS layer exposed to air, and fixed on the skin by a clear Scotch tape. To demonstrate the anti-dehydration property of the wearable living patch, a pure hydrogel device without elastomer layer was fabricated by assembling micropatterned hydrogel and flat hydrogel sheet. To compare dehydration of hydrogel-elastomer hybrids and the hydrogel device without elastomer layer, these two types of devices were conformably attached to curved surfaces of plastic beakers. The dehydration tests were carried out at room temperature with low humidity (25° C. and 50% relative humidity) for 24 h. To demonstrate the stretchability of living patch, the living skin patch was also fabricated with Ecoflex instead of PDMS in the same design and dimension. As illustrated in FIG. 13, the stretchable skin patch with induced bacteria can be stretched and relaxed to 1.8 times of its original length without failure.

Preparation and Testing of Living Chemical Detectors on Nitrile Glove Fingertip

To demonstrate the living chemical sensors at the nitrile glove fingertips, hydrogel-elastomeric glove hybrids with spiral microchannels were prepared. Thin hydrogel sheets with patterned cell chambers were first laminated on the fingertips of nitrile gloves, and then different inducible cells were encapsulated inside. Different strains of bacteria ($IPTG_{RCV}$/GFP, $AHL_{RCV}$/GFP and $Rham_{RCV}$/GFP) were injected into spiral-shaped cell chambers at different fingertips, respectively. To test the functionality of the fingertip sensor array, a cluster of cotton balls soaked in LB medium with 1 mM IPTG and 12 mM Rham was used. The glove was worn to grab the wet cotton balls, and hydrogels at the fingertips contacted the inducer-containing cotton balls. The fluorescence at the fingertips were sampled after 4 h of contact with the cotton balls using the bench-top transilluminator.

REFERENCES

1. Pardee K, et al. (2014) Paper-based synthetic gene networks. *Cell* 159(4):940-954.
2. Mimee M. Tucker A C, Voigt C A. & Lu T K (2015) Programming a human commensal bacterium, *Bacteroides* thetaiotaomicron, to sense and respond to stimuli in the murine gut microbiota. *Cell Systems* 1(1):62-71.
3. Friedland A E, et al. (2009) Synthetic gene networks that count. *Science* 324(5931):1199-1202.
4. Siuti P. Yazbek J. & Lu T K (2014) Engineering genetic circuits that compute and remember. *Nat Protoc* 9:1292-1300.
5. Chen A Y, et al. (2014) Synthesis and patterning of tunable multiscale materials with engineered cells. *Nat Mater* 13(5):515-523.
6. Florea M, et al. (2016) Engineering control of bacterial cellulose production using a genetic toolkit and a new cellulose-producing strain. *Proc Natl Acad Sci USA* 113(24):E3431-E3440.
7. Cheng A A & Lu T K (2012) Synthetic biology: an emerging engineering discipline. *Annu Rev Biomed Eng* 14:155-178.
8. Feinberg A W, et al. (2007) Muscular thin films for building actuators and powering devices. *Science* 317(5843):1366-1370.
9. Nawroth J C, et al. (2012) A tissue-engineered jellyfish with biomimetic propulsion. *Nature Biotechnol* 30(8):792-797.
10. Gerber L C, Koehler F M, Grass R N, & Stark W J (2012) Incorporation of Penicillin-Producing Fungi into Living Materials to Provide Chemically Active and Antibiotic-Releasing Surfaces. *Angew Chem Int Ed* 51(45):11293-11296.
11. Lee K Y & Mooney D J (2001) Hydrogels for tissue engineering. *Chem Rev* 101(7):1869-1880.
12. Zhao X, et al. (2011) Active scaffolds for on-demand drug and cell delivery. *Proc Natl Acad Sci USA* 108(1):67-72.
13. Seliktar D (2012) Designing cell-compatible hydrogels for biomedical applications. *Science* 336(6085):1124-1128.
14. Zhao X (2014) Multi-scale multi-mechanism design of tough hydrogels: building dissipation into stretchy networks. *Soft Matter* 10(5):672-687.
15. Yuk H. Zhang T. Parada G A. Liu X. & Zhao X (2016) Skin-inspired hydrogel-elastomer hybrids with robust interfaces and functional microstructures. *Nat Commun* 7:12028.
16. Gong J P, Katsuyama Y. Kurokawa T. & Osada Y (2003) Double-network hydrogels with extremely high mechanical strength. *Adv Mater* 15(14):1155-1158.
17. Sun J-Y, et al. (2012) Highly stretchable and tough hydrogels. *Nature* 489(7414):133-136.
18. Yuk H. Zhang T. Lin S. Parada G A. & Zhao X (2016) Tough bonding of hydrogels to diverse non-porous surfaces. *Nat Mater* 15(2):190-196.
19. Lin S, et al. (2014) Design of stiff, tough and stretchy hydrogel composites via nanoscale hybrid crosslinking and macroscale fiber reinforcement. *Soft Matter* 10(38):7519-7527.
20. Lee J N, Jiang X. Ryan D. & Whitesides G M (2004) Compatibility of mammalian cells on surfaces of poly (dimethylsiloxane). *Langmuir* 20(26):11684-11691.
21. Darnell M C, et al. (2013) Performance and biocompatibility of extremely tough alginate/polyacrylamide hydrogels. *Biomaterials* 34(33):8042-8048.
22. Robb W L (1968) Thin silicone membranes-their permeation properties and some applications. *Annals of the New York Academy of Sciences* 146(1): 119-137.
23. Huh D, et al. (2010) Reconstituting organ-level lung functions on a chip. *Science* 328(5986): 1662-1668.
24. Halldorsson S. Lucumi E. Gómez-Sjöberg R. & Fleming R M T (2015) Advantages and challenges of microfluidic cell culture in polydimethylsiloxane devices. *Biosens Bioelectron* 63:218-231.
25. Jang K-I, et al. (2014) Rugged and breathable forms of stretchable electronics with adherent composite substrates for transcutaneous monitoring. *Nat Commun* 5:4779.
26. Yuk H, et al. (2016) Hydraulic hydrogel actuators and robots optically and sonically camouflaged in water. *Nat Commun* In Press.
27. Liao I C. Moutos F T. Estes B T, Zhao X. & Guilak F (2013) Composite three-dimensional woven scaffolds with interpenetrating network hydrogels to create functional synthetic articular cartilage. *Adv Funct Mater* 23(47):5833-5839.
28. Dilanji G E, Langebrake J B, De Leenheer P. & Hagen S J (2012) Quorum activation at a distance: spatiotemporal patterns of gene regulation from diffusion of an autoinducer signal. *J Am Chem Soc* 134(12):5618-5626.
29. Lin S, et al. (2015) Stretchable Hydrogel Electronics and Devices. *Adv Mater* 28(22):4497-4502.
30. Leveau J H & Lindow S E (2001) Predictive and interpretive simulation of green fluorescent protein expression in reporter bacteria. *J Bacteriol* 183(23):6752-6762.
31. Alon U (2006) *An introduction to systems biology: design principles of biological circuits* (CRC press).
32. Kuhlman T. Zhang Z, Saier M H, & Hwa T (2007) Combinatorial transcriptional control of the lactose operon of *Escherichia coli*. *Proc Natl Acad Sci USA* 104(14):6043-6048.
33. Socolofsky S A & Jirka G H (2002) Environmental fluid mechanics part I: mass transfer and diffusion. *Class notes*: pp 32-34.
34. Cubitt A B, et al. (1995) Understanding, improving and using green fluorescent proteins. *Trends Biochem Sci* 20(11):448-455.
35. Belkin S (2003) Microbial whole-cell sensing systems of environmental pollutants. *Curr Opin Microbiol* 6(3):206-212.

ADDITIONAL REFERENCES

1. J. Singh, P. Abhilash, H. Singh, R. Singh, D. Singh, Genetically engineered bacteria: an emerging tool for environmental remediation and future research perspectives. *Gene*. 480, 1-9 (2011).
2. P. P. Peralta-Yahya. F. Zhang, S. B. del Cardayre, J. D. Keasling. Microbial engineering for the production of advanced biofuels. *Nature*. 488, 320-328 (2012).
3. J. Way, J. Collins, J. Keasling. P. Silver, Integrating Biological Redesign: Where Synthetic Biology Came From and Where It Needs to Go. *Cell*. 157, 151-161 (2014).

4. C. Wozniak. M. Gwendolyn. J. Gagliardi, M. Segal. K. Matthews, *Regulation of Genetically Engineered Microorganisms Under {FIFRA,} {FFDCA} and {TSCA}* (2012).
5. G. V. Dana. T. Kuiken. D. Rejeski, A. a. Snow, Synthetic biology: Four steps to avoid a synthetic-biology disaster. *Nature.* 483, 29-29 (2012).
6. M. M. Epstein. T. Vermeire, Scientific Opinion on Risk Assessment of Synthetic Biology. *Trends Biotechnol.* 34, 601-603 (2016).
7. K. Hagen, Science Policy and Concomitant Research in Synthetic Biology—Some Critical Thoughts. *Nanoethics.* 10, 201-213 (2016).
8. J. J. C. Clement T Y Chan, Jeong Wook Lee, D Ewen Cameron. Caleb J Bashor, "Deadman" and "passcode" microbial kill switches for bacterial containment. *Nat. Chem. Biol.* 12, 82-85 (2015).
9. M. J. Lajoie et al., Probing the limits of genetic recoding in essential genes. *Science (80-.).* 342, 361-363 (2013).
10. M. J. Lajoie et al., Genomically recoded organisms expand biological functions. *Science (80-.).* 342, 357-360 (2013).
11. A. Rovner et al., Recoded organisms engineered to depend on synthetic amino acids. *Nature.* 518, 89-93 (2015).
12. L. T. Bereza-Malcolm. G. lay Mann. A. E. Franks. Environmental sensing of heavy metals through whole cell microbial biosensors: a synthetic biology approach. *ACS Synth. Biol.* 4, 535-546 (2014).
13. D. Seliktar. Designing cell-compatible hydrogels for biomedical applications. *Science (80-.).* 336, 1124-1128 (2012).
14. M. Choi et al., Light-guiding hydrogels for cell-based sensing and optogenetic synthesis in vivo. *Nat. Photonics.* 7, 987-994 (2013).
15. A. C. Anselmo, K. J. McHugh, J. Webster, R. Langer, A. Jaklenec, Layer-by-Layer Encapsulation of Probiotics for Delivery to the Microbiome. *Adv. Mater.* (2016). doi: 10.1002/adma.201603270.
16. K. Lee, D. Mooney, Alginate: properties and biomedical applications. *Prog. Polym. Sci.* 37, 106-126 (2012).
17. C. Kearney, D. Mooney, Macroscale delivery systems for molecular and cellular payloads. *Nat Mater.* 12, 1004-1017 (2013).
18. K. Y. Lee, D. J. Mooney, Alginate: properties and biomedical applications. *Prog. Polym. Sci.* 37, 106-126 (2012).
19. A. J. Vegas et al., Supplemental Information—Combinatorial hydrogel library enables identification of materials that mitigate the foreign body response in primates. *Nat. Biotechnol.* 34, 345-352 (2016).
20. T. Billiet, M. Vandenhaute, J. Schelfhout, S. Van Vlierberghe, P. Dubruel, A review of trends and limitations in hydrogel-rapid prototyping for tissue engineering. *Biomaterials.* 33, 6020-6041 (2012).
21. F. Farzadfard, T. K. Lu, Genomically encoded analog memory with precise in vivo DNA writing in living cell populations. *Science (80-.).* 346, 1256272-1256272 (2014).
22. A. J. Rovner et al., Recoded organisms engineered to depend on synthetic amino acids. *Nature.* 518, 89-93 (2015).
23. J.-Y. Sun et al., Highly stretchable and tough hydrogels (2012). doi:10.1038/nature11409.
24. B. Trappmann et al., Extracellular-matrix tethering regulates stem-cell fate. *Nat. Mater.* 11, 642-649 (2012).
25. D. Valade, L. K. Wong, Y. Jeon. Z. Jia, M. J. Monteiro, Polyacrylamide hydrogel membranes with controlled pore sizes. *J. Polym. Sci. Part A Polym. Chem.* 51, 129-138 (2013).
26. C. A. Gordon. N. A. Hodges, C. Marriott, Antibiotic interaction and diffusion through alginate and exopolysaccharide of cystic fibrosis-derived *Pseudomonas aeruginosa*. *J. Antimicrob. Chemother.* 22, 667-674 (1988).
27. A. Tamsir, J. J. Tabor, C. A. Voigt, Robust multicellular computing using genetically encoded NOR gates and chemical/wires/'. *Nature.* 469, 212-215 (2011).
28. S. Basu, Y. Gerchman, C. H. Collins, F. H. Arnold, R. Weiss, A synthetic multicellular system for programmed pattern formation. *Nature.* 434, 1130-1134 (2005).
29. P. Szafranski et al., A new approach for containment of microorganisms: dual control of streptavidin expression by antisense RNA and the T7 transcription system. *Proc. Natl. Acad. Sci. U.S.A.* 94, 1059-63 (1997).
30. W. Kong et al., Regulated programmed lysis of recombinant *Salmonella* in host tissues to release protective antigens and confer biological containment. *Proc. Natl. Acad. Sci. U.S.A.* 105, 9361-6 (2008).
31. L. Steidler et al., Biological containment of genetically modified *Lactococcus lactis* for intestinal delivery of human interleukin 10. *Nat Biotechnol.* 21, 785-789 (2003).
32. K. R. Brocklehurst et al., ZntR is a Zn (II)-responsive MerR-like transcriptional regulator of zntA in *Escherichia coli*. *Mol. Microbiol.* 31, 893-902 (1999).
33. "310 CMR 30.000" (2015).
34. O. Wright. G.-B. Stan. T. Ellis, Building-in biosafety for synthetic biology. *Microbiology.* 159, 1221-1235 (2013).
35. C. Knierim, C. L. Greenblatt, S. Agarwal, A. Greiner, Blocked bacteria escape by ATRP grafting of a PMMA shell on PVA microparticles. *Macromol. Biosci.* 14, 537-545 (2014).
36. A. De Las Heras, C. A. Carrero, V. De Lorenzo, Stable implantation of orthogonal sensor circuits in Gram-negative bacteria for environmental release. *Environ. Microbiol.* 10, 3305-3316 (2008).
37. X. Liu et al., Stretchable living materials and devices with hydrogel—elastomer hybrids hosting programmed cells. *Proc. Natl. Acad. Sci.* 114, 2200-2205 (2017).

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A hydrogel-elastomer composition encapsulating a population of genetically-engineered cells that comprise a promoter operably linked to a nucleic acid encoding a product of interest, wherein the hydrogel is infused with cell nutrients, and wherein the elastomer is microporous.

2. The composition of claim 1, wherein the hydrogel is comprised of polyacrylamide (PAAm)-alginate.

3. The composition of claim 2, wherein the PAAm is covalently crosslinked PAAm and the alginate is ionically crosslinked alginate.

4. The composition of claim 1, wherein the elastomer is air-permeable.

5. The composition of claim 1, wherein the elastomer is comprised of silicone.

6. The composition of claim 5, wherein the silicone is polydimethylsiloxane (PDMS) or platinum-catalyzed silicone.

7. The composition of claim 1, wherein the promoter is an inducible promoter.

8. The composition claim 1, wherein the genetically-engineered cells are genetically-engineered bacterial cells.

9. A wearable device comprising the hydrogel-elastomer composition of claim 1.

10. The wearable device of claim 9, wherein the wearable device is a skin patch or a biosensing glove.

11. The composition of claim 1, wherein the cells remain viable for at least 12 hours.

12. A method of producing the composition of claim 1, the method comprising:
(a) contacting a hydrogel-elastomer composition with a solution containing cell nutrients to produce a nutrient-infused hydrogel-elastomer composition; and
(b) introducing a population of genetically-engineered cells into the nutrient-infused hydrogel-elastomer composition to produce genetically-engineered cells encapsulated by the nutrient-infused hydrogel, wherein the genetically-engineered cells comprise a promoter operably linked to a nucleic acid encoding a product of interest.

13. A hydrogel-alginate capsule comprising a hydrogel shell and an alginate core containing a population of genetically-engineered cells that comprise a promoter operably linked to a nucleic acid encoding a product of interest, and wherein the hydrogel shell and the alginate core are different types of hydrogels.

14. A composition comprising:
(a) an environmental sample comprising at least one contaminant; and
(b) the hydrogel-alginate capsule of claim 13, wherein the promoter is an inducible promoter that is modulated by the at least one contaminant.

15. The composition of claim 14, wherein the genetically-engineered cells are auxotrophic for at least one nutrient.

16. The composition of claim 15, wherein the at least one nutrient is an amino acid.

17. A method of producing the hydrogel-alginate capsule of claim 13, the method comprising:
(a) combining a culture of genetically-engineered cells with alginate to produce droplets;
(b) crosslinking the droplets with calcium ions to form spheres containing the genetically-engineered cells; and
(c) encapsulating the spheres with a hydrogel to form a capsule, wherein the genetically-engineered cells comprise a promoter operably linked to a nucleic acid encoding a product of interest, and wherein the hydrogel shell and the alginate core are different types of hydrogels.

18. A system comprising:
(a) a first population of hydrogel-alginate capsules comprising (i) a hydrogel shell and (ii) an alginate core containing a population of genetically-engineered cells that comprise a first inducible promoter operably linked to a nucleic acid encoding a first product of interest, and wherein the hydrogel shell and the alginate core are different types of hydrogels; and
(b) a second population of hydrogel-alginate capsules comprising (i) a hydrogel shell and (ii) an alginate core containing a population of genetically-engineered cells that comprise a second inducible promoter operably linked to a nucleic acid encoding a second product of interest, wherein activity of the second inducible promoter is modulated by the first product of interest, and wherein the hydrogel shell and the alginate core are different types of hydrogels.

* * * * *